(12) United States Patent
Biolchini, Jr.

(10) Patent No.: US 11,439,422 B2
(45) Date of Patent: Sep. 13, 2022

(54) AMBIDEXTROUS LOCKING CLAMP SYSTEM

(71) Applicant: Robert F. Biolchini, Jr., Jackson, WY (US)

(72) Inventor: Robert F. Biolchini, Jr., Jackson, WY (US)

( * ) Notice: Subject to any disclaimer, the term of this patent is extended or adjusted under 35 U.S.C. 154(b) by 83 days.

(21) Appl. No.: 16/353,010

(22) Filed: Mar. 14, 2019

(65) Prior Publication Data

US 2019/0209191 A1    Jul. 11, 2019

Related U.S. Application Data

(63) Continuation-in-part of application No. 15/070,272, filed on Mar. 15, 2016, now Pat. No. 10,327,792, which is a continuation-in-part of application No. 13/272,676, filed on Oct. 13, 2011, now Pat. No. 9,427,245, which is a continuation-in-part of application No. 11/733,280, filed on Apr. 10, 2007, now Pat. No. 8,070,771, which is a continuation-in-part of application No. 10/909,623, filed on Aug. 2, 2004, now Pat. No. 7,758,609.

(51) Int. Cl.
*A61B 17/28*      (2006.01)
*A61B 17/122*     (2006.01)
*A61B 17/00*      (2006.01)
*A61B 17/3201*    (2006.01)

(52) U.S. Cl.
CPC ........ *A61B 17/2833* (2013.01); *A61B 17/122* (2013.01); *A61B 17/3201* (2013.01); *A61B 2017/0042* (2013.01); *A61B 2017/00446* (2013.01); *A61B 2017/00477* (2013.01); *A61B 2017/2808* (2013.01); *A61B 2017/2837* (2013.01)

(58) Field of Classification Search
CPC .............. A61B 17/2833; A61B 17/122; A61B 2017/00477; A61B 2017/00446; A61B 2017/2837; A61B 2017/2808; A61B 2017/0042
See application file for complete search history.

(56) References Cited

U.S. PATENT DOCUMENTS

| | | | |
|---|---|---|---|
| 2,253,132 A | 5/1940 | Malson | |
| 3,157,075 A | 11/1964 | Filia | |
| 3,417,752 A | 12/1968 | Butler | |

(Continued)

*Primary Examiner* — Richard G Louis
(74) *Attorney, Agent, or Firm* — David Guerra

(57) ABSTRACT

An ambidextrous locking clamp system for providing a user the ability to use the right or left hand to engage and disengage a ratcheting means on the clamp. The clamp includes hingedly connected first and second elongated members each with a finger engaging member, a working head, and a latching member featuring ratcheting teeth. The teeth are engaged by moving the finger engaging members toward each other in an engaging motion, and are disengaged by sliding them in a disengaging motion perpendicular to the engaging motion with opposing force applied to the finger engaging members. One of the elongated members includes a planar portion that is rotatably received in a slot defined in a female portion of the other elongated member. The planar portion can include a wedge that contacts a side of the female portion that defines the slot when the clamp is in a closed position.

18 Claims, 34 Drawing Sheets

(56) References Cited

U.S. PATENT DOCUMENTS

| | | | |
|---|---|---|---|
| D218,792 S | | 9/1970 | Blomberg |
| 3,654,930 A | | 4/1972 | Hobbs, II |
| 3,823,719 A | | 7/1974 | Cummings |
| 3,873,016 A | | 3/1975 | Fishbein |
| 3,913,586 A | | 10/1975 | Baumgarten |
| 3,978,584 A | | 9/1976 | Mayer |
| 4,452,246 A | | 6/1984 | Bader et al. |
| 4,823,792 A | | 4/1989 | Dulebohn et al. |
| 5,176,702 A | | 1/1993 | Bales |
| 5,514,147 A | * | 5/1996 | Hoskin ............. A61B 17/2812 606/208 |
| 5,626,608 A | | 5/1997 | Cuny |
| 6,187,003 B1 | * | 2/2001 | Buysse ............. A61B 17/2816 30/342 |
| 6,223,440 B1 | | 5/2001 | Rashman |
| 6,397,478 B1 | | 6/2002 | Bornancini |
| 7,727,256 B2 | | 6/2010 | McGregor |
| 8,210,845 B1 | * | 7/2012 | Ingels ..................... A61C 7/04 433/4 |
| 2004/0106947 A1 | | 6/2004 | Propp |
| 2010/0064862 A1 | | 3/2010 | Fournier |
| 2012/0203272 A1 | * | 8/2012 | Wohl ..................... A61B 17/26 606/205 |
| 2014/0088639 A1 | * | 3/2014 | Bartels ............... A61B 17/2816 606/207 |
| 2018/0000536 A1 | * | 1/2018 | Becker .................. A61B 17/29 |
| 2019/0336156 A1 | * | 11/2019 | Hammerland, III ........................ A61B 18/1442 |

\* cited by examiner

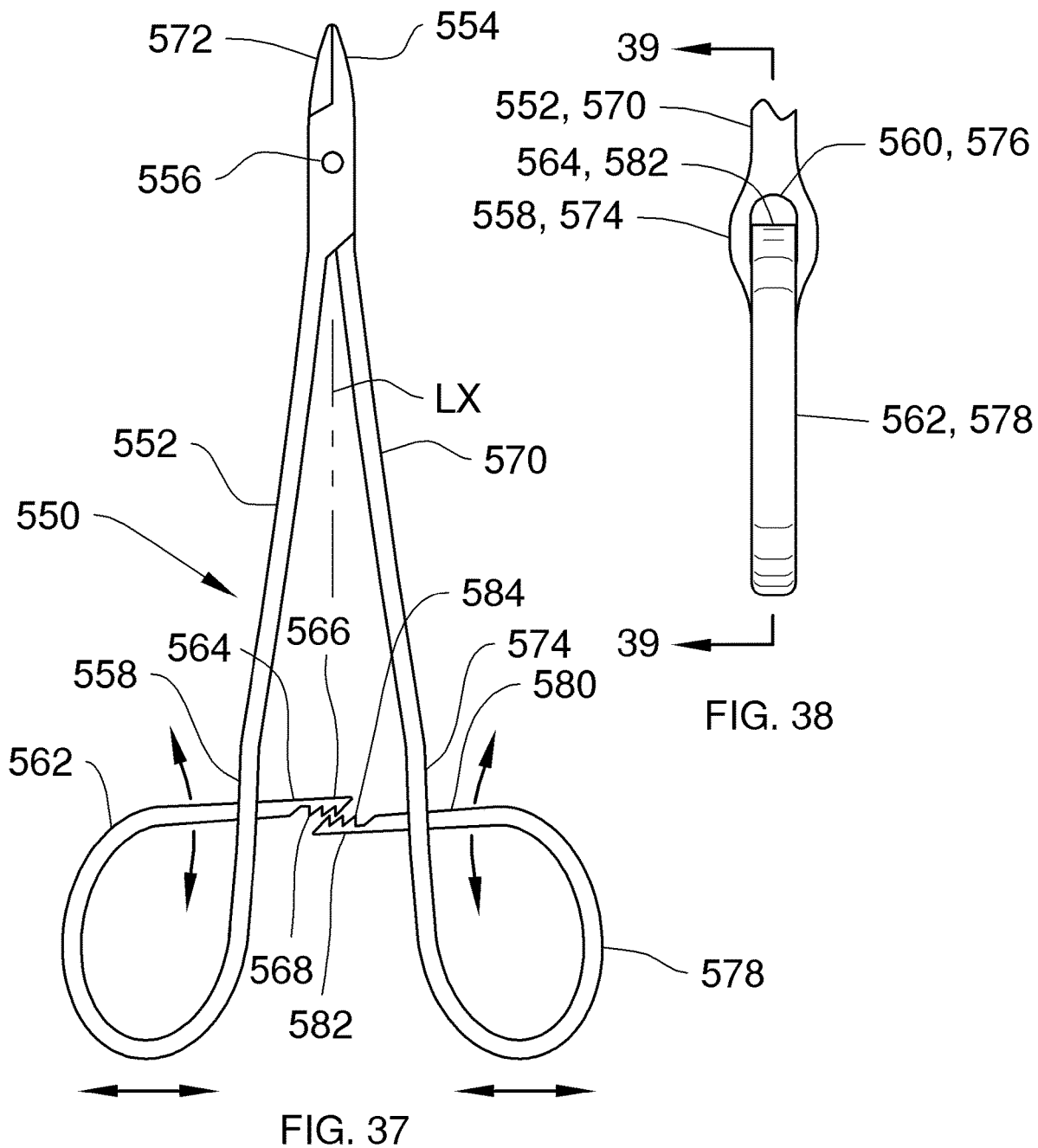

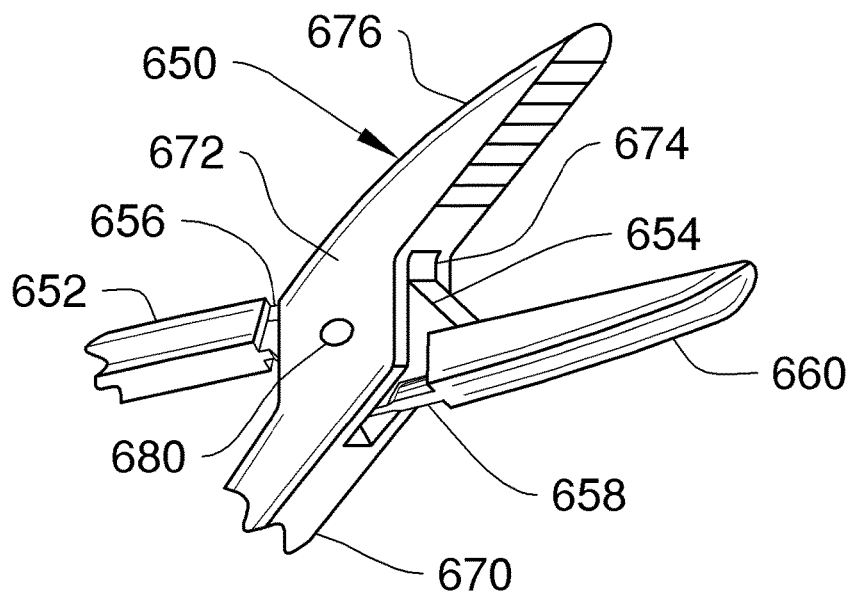
FIG. 43
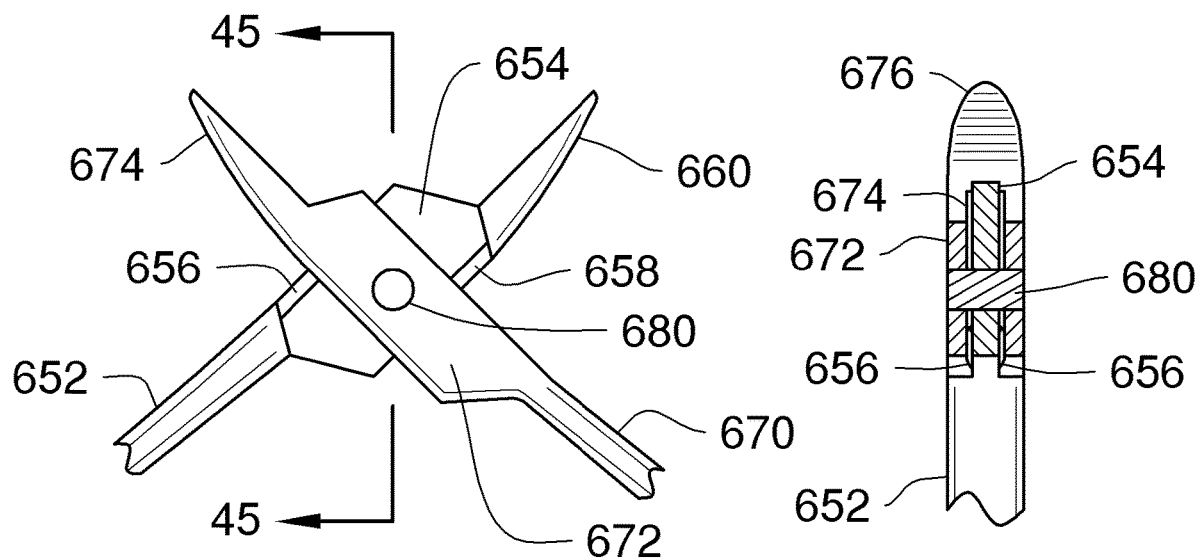
FIG. 44
FIG. 45

AMBIDEXTROUS LOCKING CLAMP SYSTEM

CROSS REFERENCE TO RELATED APPLICATION

This application is a continuation-in-part under 35 U.S.C. § 120 based upon co-pending U.S. patent application Ser. No. 15/070,272 filed on Mar. 15, 2016, which is a continuation-in-part application of U.S. patent application Ser. No. 13/272,676 filed on Oct. 13, 2011 now U.S. Pat. No. 9,427,245 issued on Aug. 30, 2016, which is a continuation-in-part application of U.S. patent application Ser. No. 11/733,280 filed on Apr. 10, 2007 now U.S. Pat. No. 8,070,771 issued on Dec. 6, 2011, which is a continuation-in-part application of U.S. application Ser. No. 10/909,623 filed on Aug. 2, 2004 now U.S. Pat. No. 7,758,609 issued on Jul. 20, 2010. All of which are incorporated herein by reference in their entirety.

BACKGROUND

Technical Field

The present technology relates to an ambidextrous locking clamp system for use in connection with clamping instruments, such as surgical clamps, forceps, or hemostats. The ambidextrous locking clamp system has particular utility in connection with manipulating a hand tool to engage latching members by moving flexible members toward each other which, and to disengage the latching members by sliding the latching members in a motion perpendicular to the engaging motion thereby flexing the flexible members away from each other when an opposing force is applied to the flexible members. The opposing force is produced by pushing with a thumb of an operating hand of a user on one of the flexible members and pulling with fingers of the operating hand on the other flexible member thereby slidably separating the latching members.

Background Description

Ambidextrous locking clamps, forceps or hemostats are desirable for allowing a right or left-handed user to use a single hand operated clamp, forceps or hemostat device. These hand operated devices have been manufactured in the past for either a right hand or left hand user. This manufacturing process has some disadvantages in that the manufacturer would have to make a decision as to how many right handed and left handed devices to fabricate. In most cases, the decision is made to manufacture more right-handed devices than left handed devices. Therefore, it is well known that it is very difficult for a left-handed user to operate a right-handed device.

Hand operated locking clamps, forceps and hemostats are known in the art. These devices include a pair of elongated members joined by a hinge. The hinge is usually a hinge pin extending through both elongated members. One end of the elongated members features a working head, usually a griping jaw or cutting edges. The other end of the elongated members feature a finger engaging loop, with a set of ratchet teeth extending out therefrom towards the ratchet teeth of the finger loop of the second elongated member. The ratchet teeth are orientated so that they engage each other when the finger loop ends are brought together. These devices are mainly used in the medical industry for a wide variety of uses, but they are also used in the fly fishing, model building, and electrical industries.

During operation of a standard right handed hand operated device, the user inserts his or her thumb into one loop, the middle finger in the opposite loop, and the index finger would rest on the top of the middle finger loop for support and control of the device. To engage the working head the user squeezes the thumb and middle finger together guided by the index finger. The device is locked in the close position by further squeezing the loops together until the ratchet teeth members engage each other. To release, the thumb pushes away from the palm of the hand and the middle finger pulls toward the palm of the hand. This motion makes the ratchet teeth members flex away from each other and disengage.

The difficulty lies when a left-handed user tries to operate a right-handed device. It is difficult for a left-handed user to pull with the thumb and push with the middle finger. This is not a natural hand motion.

While the above-described devices fulfill their respective, particular objectives and requirements, the aforementioned patents do not describe an ambidextrous hand operated device that allows the use of the device by a right or left handed user through the engaging of latching members by moving flexible members toward each other which, and the disengaging of the latching members by sliding the latching members in a motion perpendicular to the engaging motion thereby flexing the flexible members away from each other when an opposing force is applied to the flexible members. Wherein, the opposing force is produced by pushing with a thumb of an operating hand of a user on one of the flexible members and pulling with fingers of the operating hand on the other flexible member thereby slidably separating the latching members.

Therefore, a need exists for a new and improved ambidextrous locking clamp system that can be used for manipulating objects with a tool having removable and interchangeable components. In this regard, the present technology substantially fulfills this need. In this respect, the ambidextrous locking clamp system according to the present technology substantially departs from the conventional concepts and designs of the prior art, and in doing so provides an apparatus primarily developed for the purpose of manipulating a hand tool to engage latching members by moving flexible members toward each other which, and to disengage the latching members by sliding the latching members in a motion perpendicular to the engaging motion thereby flexing the flexible members away from each other when an opposing force is applied to the flexible members. The opposing force is produced by pushing with a thumb of an operating hand of a user on one of the flexible members and pulling with fingers of the operating hand on the other flexible member thereby slidably separating the latching members.

BRIEF SUMMARY OF THE PRESENT TECHNOLOGY

In view of the foregoing disadvantages inherent in the known types of hand operated locking devices, the present technology provides an improved ambidextrous locking clamp system, and overcomes the above-mentioned disadvantages and drawbacks of the prior art. As such, the general purpose of the present technology, which will be described subsequently in greater detail, is to provide a new and improved ambidextrous locking clamp system and method which has all the advantages of the prior art mentioned heretofore and many novel features that result in a ambidextrous locking clamp system which is not anticipated, rendered obvious, suggested, or even implied by the prior art, either alone or in any combination thereof.

According to one aspect of the present technology, the present technology essentially includes an ambidextrous locking clamp system for allowing a right hand or left hand user to operate said clamp. The system can include a first member and a second member pivotably connected with each other. The first member can include at least one first elongated body, at least one first finger engaging member, and at least one first latching member. The first elongated body can include a planar portion, and at least one first working head located at an end of the first elongated body. The first latching member can include first member ratcheting teeth. The second member can include at least one second elongated body, at least one second finger engaging member, and at least one second latching member. The second elongated body can include a female portion defining a slot, and at least one second working head located at an end of the second elongated body. The slot can be configured to receive the planar portion of the first member. The second latching member can include at least one second member ratcheting teeth. The first and second members being in a pivotable relationship about a pivot point so that the first and second working heads move toward each other when the first and second finger engaging member are moved toward each other.

According to an aspect of the present technology, the present technology essentially includes an ambidextrous locking clamp system. The system can include a first member and a second member pivotably connected with each other. The first member can include at least one first elongated body, at least one first finger engaging member, and at least one first latching member. The first elongated body can include a planar portion, and at least one first working head located at an end of the first elongated body. The first latching member can include first member ratcheting teeth. The second member can include at least one second elongated body, at least one second finger engaging member, and at least one second latching member. The second elongated body can include a female portion defining a slot, and at least one second working head located at an end of the second elongated body. The slot can be configured to receive the planar portion of the first member. The second latching member can include second member ratcheting teeth. The first and second members being pivotably connected about a pivot point so that the first and second working heads move toward each other when the first and second finger engaging member are moved toward each other. The first and second member ratcheting teeth can be orientated to be engageable with each other by an engaging motion when the first and second finger engaging members are moved toward each other.

According to yet another aspect of the present technology, the present technology can include a method of using an ambidextrous locking clamp system. The method can include the steps of operating a first finger engaging member of a first member and a second finger engaging member of a second member by a user to move the first and second finger engaging members toward each other about a pivot point in an engaging motion. The pivot point can be configured to pivotably connect the first and second members to each other. Rotating a planar portion of the first member and a female portion of the second member about the pivot point during the engaging motion. The planar portion can be receivable in a slot defined in the female portion. Engaging ratcheting teeth of first and second members with each other by the engaging motion until the ratcheting teeth of the first and second members overlap one another in succession to a user desired tension when a working head of the first member and the second member are in a closed position. Disengaging the ratcheting teeth of the first and second members by a disengaging motion perpendicular to the engaging motion until the ratcheting teeth are slidably disengaged. The disengaging motion can be produced by moving the first and second members in opposite directions when an opposing force is applied to the first and second finger engaging members by pushing on at least one of the first and second finger engaging members and pulling on the other of the first and second finger engaging members thereby slidably separating the ratcheting teeth of the first and second members out of engagement In some embodiments of the present technology, operating the first finger engaging member of the first member can be accomplished by utilizing at least a thumb or a finger of an operating hand of the user, while operating the second finger engaging member of the second member by at least a thumb or a finger of the operating hand of the user that is not used in operating the first finger engaging member.

In some embodiments of the present technology, the disengaging motion can be produced by moving the first and second members in opposite directions when an opposing force is applied to the first and second finger engaging members by pushing with the thumb of the operating hand on at least one of the first and second finger engaging members and pulling with the finger of the operating hand on the other of the first and second finger engaging members.

In some embodiments of the present technology, the planar portion can include at least one wedge configured to contact a side of said female portion that defines the slot when the first and second working heads are in a closed position.

In some embodiments of the present technology, the wedge can extend from the planar portion so that an exterior edge of the wedge is flush with an edge of the planar portion.

In some embodiments of the present technology, the wedge can include an exterior side and an interior tapered side. The wedge can be configured so that the interior tapered side enters the slot prior to the exterior side during the engaging motion.

In some embodiments of the present technology, the can be a pair of wedges each extending from opposite sides of the planar portion away from each other.

In some embodiments of the present technology, the wedge can be adjacent the first elongated body, with the pivot point being located between the wedge and the working head of the first member.

Some embodiments of the present technology, the planar portion can include at least one secondary wedge configured to contact a side of the female portion that defines the slot when the first and second working heads are in a closed position.

In some embodiments of the present technology, the secondary wedge can include an exterior side and an interior tapered side. The secondary wedge can be configured so that the interior tapered side of the secondary wedge enters the slot prior to the exterior side of the secondary wedge during the engaging motion.

In some embodiments of the present technology, the secondary wedge can be a pair of secondary wedges each extending from opposite sides of the planar portion away from each other.

In some embodiments of the present technology, the secondary wedge can be adjacent the working head of the first member, with the pivot point being located between the wedge and the secondary wedge.

In some embodiments of the present technology, the wedge and the secondary wedge can be located on opposite sides of a longitudinal axis of the first member.

Some embodiments of the present technology can include the first latching member received through a first member opening defined through the first elongated member, and the second latching member received through a second member opening defined through the second elongated member.

In some embodiments of the present technology, the first member opening can be a recess defined by a bent portion of the first elongated body, and the second member opening can be a recess defined by a bent portion of the second elongated body.

In some embodiments of the present technology, the first member opening can be a bore defined through the first elongated body, and the second member opening can be a bore defined through the second elongated body.

In some embodiments of the present technology, the first and second member ratcheting teeth can have a configuration for disengaging with each other by sliding the first and second member ratcheting teeth apart by a disengaging motion perpendicular to the engaging motion resulting in moving the first and second latching members away from each other when an opposing force is applied to the first and second finger engaging members.

There has thus been outlined, rather broadly, the more important features of the technology in order that the detailed description thereof that follows may be better understood and in order that the present contribution to the art may be better appreciated.

The technology may also include a variety of latching members, such as, but not limited to, rigid latching members, flexible latching members, flexible armed latching members, and ratcheting heads. There are, of course, additional features of the technology that will be described hereinafter and which will form the subject matter of the claims attached.

Numerous embodiments, features and advantages of the present technology will be readily apparent to those of ordinary skill in the art upon a reading of the following detailed description of presently preferred, but nonetheless illustrative, embodiments of the present technology when taken in conjunction with the accompanying drawings. In this respect, before explaining the current embodiment of the technology in detail, it is to be understood that the technology is not limited in its application to the details of construction and to the arrangements of the components set forth in the following description or illustrated in the drawings. The technology is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present technology. It is important, therefore, that the claims be regarded as including such equivalent constructions insofar as they do not depart from the spirit and scope of the present technology.

It is therefore an embodiment of the present technology to provide a new and improved ambidextrous locking clamp system that has all of the advantages of the prior art locking clamps and none of the disadvantages.

It is another embodiment of the present technology to provide a new and improved ambidextrous locking clamp system that may be easily and efficiently manufactured and marketed.

An even further embodiment of the present technology is to provide a new and improved ambidextrous locking clamp system that has a low cost of manufacturing with regard to both materials and labor, and which accordingly is then susceptible of low prices of sale to the consuming public, thereby making such ambidextrous locking clamp system economically available to the buying public.

Still another embodiment of the present technology is to provide a new ambidextrous locking clamp system that provides in the apparatuses and methods of the prior art some of the advantages thereof, while simultaneously overcoming some of the disadvantages normally associated therewith.

Lastly, it is an object of the present technology to provide a new and improved method of using the ambidextrous locking clamp system by engaging the first and second member ratcheting teeth with each other by an engaging motion provided by the operating hand of a user until the ratcheting teeth overlap one another in succession to a user desired tension. The engaging motion is produced by moving the first and second finger engaging members toward each other. The ratcheting teeth are disengaged by a disengaging motion perpendicular to the engaging motion resulting in moving the first and second latching members away from each other when an opposing force. The disengaging motion is produced by move the first and second members in opposite directions when an opposing force is applied to the first and second finger engaging members by pushing with a thumb of the operating hand of the user on at least one of the first and second finger engaging members and pulling with at least one finger of the operating hand on the other of the first and second finger engaging members thereby slidably separating the ratcheting teeth out of engagement.

These together with other embodiments of the technology, along with the various features of novelty that characterize the technology, are pointed out with particularity in the claims annexed to and forming a part of this disclosure. For a better understanding of the technology, its operating advantages and the specific embodiments attained by its uses, reference should be had to the accompanying drawings and descriptive matter in which there are illustrated preferred embodiments of the technology.

BRIEF DESCRIPTION OF THE DRAWINGS

The technology will be better understood and embodiments other than those set forth above will become apparent when consideration is given to the following detailed description thereof. Such description makes reference to the annexed drawings wherein:

FIG. 37 is a front plane view of an alternate embodiment of the present technology.

FIG. 38 is a side plane view of the alternate embodiment in FIG. 37.

FIG. 43 is a perspective view of an alternate embodiment working head section of the present technology.

FIG. 44 is a front plane view of the alternate embodiment in FIG. 43 with the working head in an open configuration.

FIG. 45 is a cross-sectional view of the embodiment in FIG. 44 taken along cross-section line 45-45.

The same reference numerals refer to the same parts throughout the various FIGS.

DETAILED DESCRIPTION OF THE PRESENT TECHNOLOGY

Figure 1:
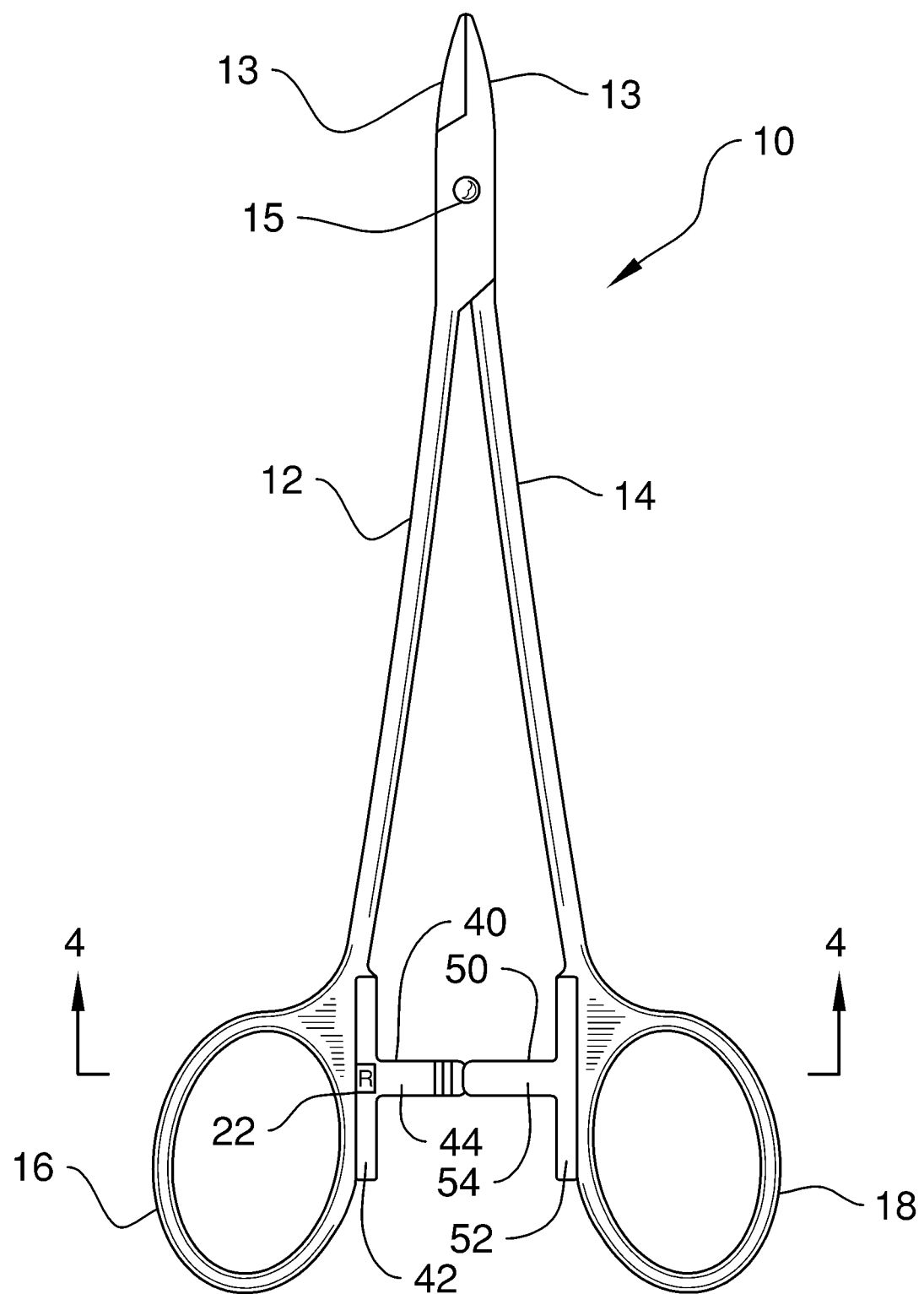
FIG. 1 is a front plane view of the ambidextrous locking clamp system constructed in accordance with the principles of the present technology.

Referring now to the drawings and particularly to FIGS. 1-48, a first embodiment of the ambidextrous locking clamp system of the present technology is shown and generally designated by the reference numeral 10.

In FIG. 1, a new and improved ambidextrous locking clamp system 10 of the present technology for allowing the use of a hand operated device by a right or left handed user is illustrated and will be described. More particularly, the ambidextrous locking clamp system 10 has a first elongated member 12 and a second elongated member 14 each having a working head 13, wherein the working heads can be, but not limited to, a gripping jaw or a cutting edge. The second elongated member 14 is connected to the first elongated member 12 via a hinge 15. The first and second elongated members 12, 14 each has a corresponding finger engaging member 16, 18 located opposite of their respective working heads 13, wherein each finger engaging member has an indicator 22, 32 for identifying a first and second side of the ambidextrous locking clamp system. Additionally, a first latching member 40 is removably attached to the finger engaging members 16, 18 and a second latching member 50 is removably attached to the finger engaging members 16, 18. The first and second elongated members 12, 14 can be made from any suitable material having reflex memory.

Figure 2:
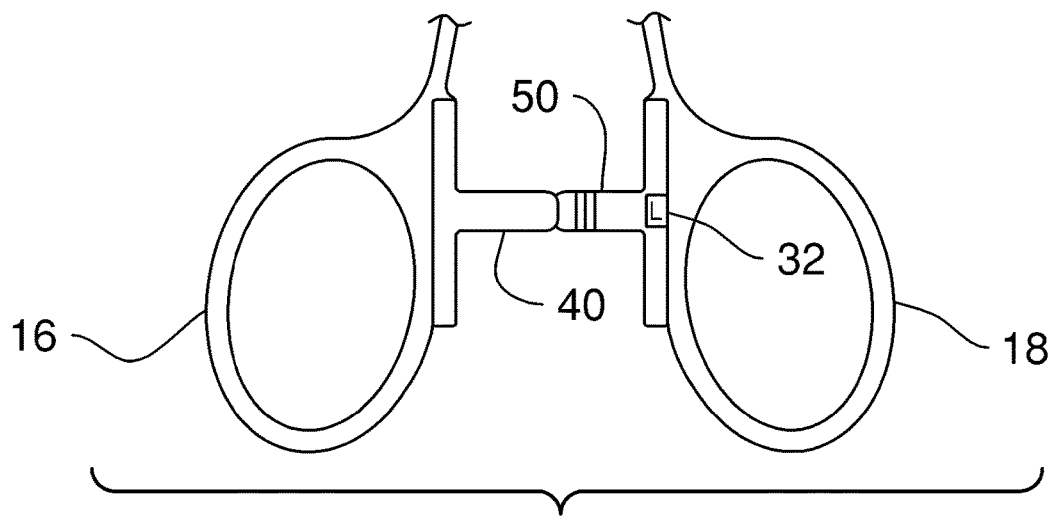
FIG. 2 is an enlarged front plane view of the ambidextrous locking clamp system in an alternate configuration of the present technology.

The indicators 22, 32 will have a marking or indicia thereon, such as but limited to an "L" and "R" to indicate the configuration of the ambidextrous locking clamp 10. Indicator 22 is located on a protrusion 20 extending out from the first finger engaging member 16, and indicator 32 is located on a protrusion 30 extending out from the second finger engaging member 18. The indicators 22, 32 are intended to separately and independently identify the first and second elongated members 12, 14 of the ambidextrous locking clamp system 10 respectively attached thereon, so a user can distinguish between the left and right, as best illustrated in FIGS. 1 and 2.

Figure 3:
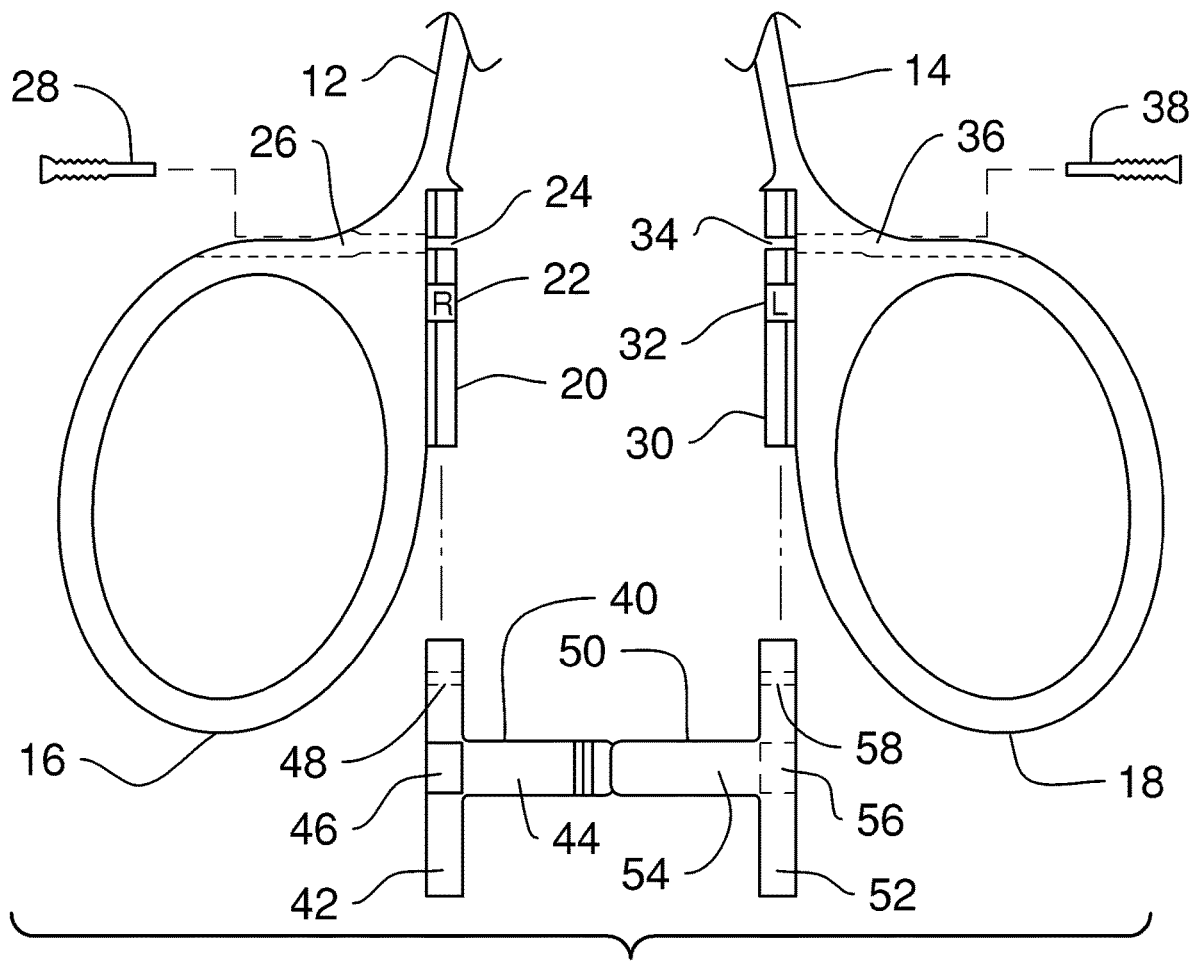
FIG. 3 is an exploded front plane view of the ambidextrous locking clamp system of the present technology.
Figure 5:
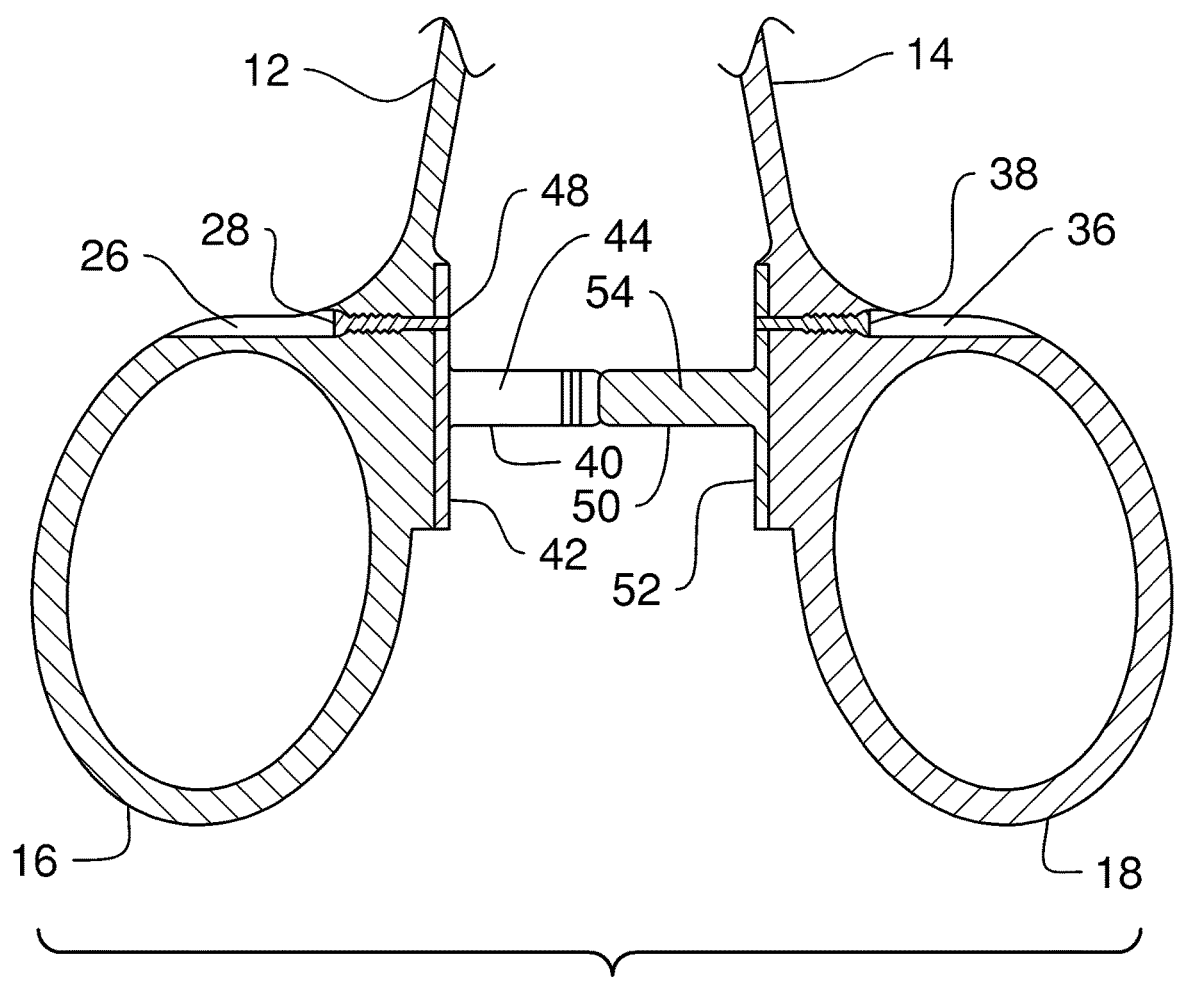
FIG. 5 is a cross-sectional view of the embodiment in FIG. 4 taken along cross-section line 5-5.

The first and second latching members 40, 50 each have an elongated base 42, 52, a ratcheting head 44, 54 extending out from their respective elongated base, an opening 46, 56 for viewing the indicator 22, 32 therebelow, and an aperture 48, 58 adapted and configured to receive a threaded retaining pin 28, 38. The ratcheting heads 44, 54 are substantially perpendicular to their respective elongated bases 42, 52, thereby forming a generally T-shaped configuration. The retaining pins 28, 38 are securely retained within a bore 26, 36 defined through the finger engaging members 16, 18, and also extend through the apertures 48, 58 thereby prevent the latching members 40, 50 from being removed from their respective protrusions 20, 30. The bores 26, 36 can be partially or completely threaded so as to threadably receive the retaining pins 28, 38, as best illustrated in FIGS. 3 and 5. The retaining pins 28, 38 can each have a non-threaded tip configured to be received through the apertures 48, 58 of the latching members 40, 50. The ratcheting heads 44, 54 feature a plurality of teeth thereon, which are adapted to join and lock together when engaged by squeezing the finger engaging members 16, 18 together. The teeth are able to disengage when pulled apart by the flexing of the first and second elongated members 12, 14 when an opposing force is applied to the finger engaging members 16, 18.

Figure 4:
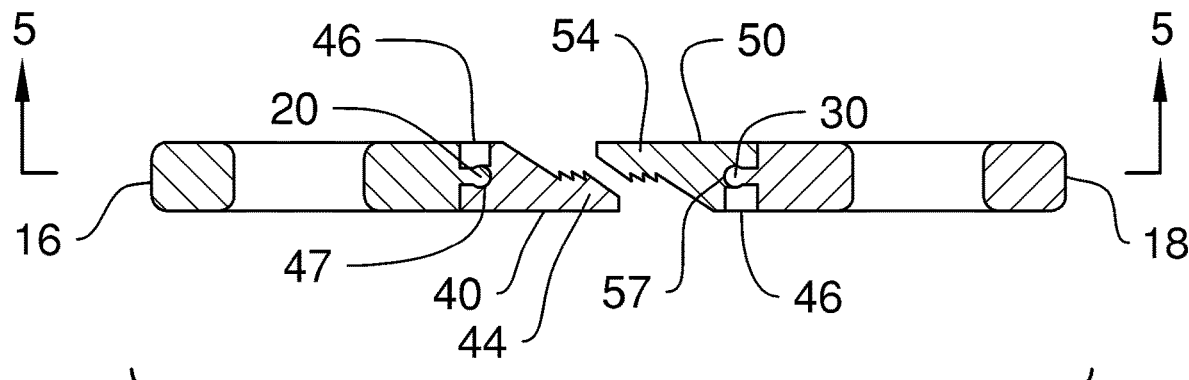
FIG. 4 is a cross-sectional view of the embodiment in FIG. 4 taken along cross-section line 4-4.

The protrusion 20 features a notch 24 aligned with the bore 26. The bore 26 and the notch 24 are adapted and configured to receive the retaining pin 28, 38 therethrough. The retaining pin 28 is threaded and has a non-threaded tip, wherein the tip is adapted to be received through the notch 24. The protrusion 20 is adapted to slidably receive latching members 40, 50. The protrusion 30 features a notch 34 aligned with the bore 36. The bore 36 and the notch 34 are adapted and configured to receive the retaining pin 28, 38 therethrough. The retaining pin 38 is threaded and has a non-threaded tip, wherein the tip is adapted to be received through the notch 34. The protrusion 30 is adapted to slidably receive latching members 40, 50. FIG. 3 is an exploded view best illustrating the above configuration. It can be appreciated that retaining pins 28, 38 are identical and interchangeable The elongated base 42, 52 of the first and second latching members 40, 50 each have a channel 47, 57 running the length of the elongated base. The channels 47, 57 are adapted and configured to slide on and be retained by the protrusions 20, 30 extending out from the finger engaging members 16, 18. The configuration of the channels 47, 57 and the protrusions 20, 30 allow the first and second latching members 40, 50 to slide over the protrusion, but at the same time not allowing the latching members to be pulled off the protrusions in a direction perpendicular to the sliding motion. FIGS. 4 and 5 best illustrate one possible example of the channel and protrusion configuration.

The first and second latching members 40, 50 are symmetrical so that they may be removed, inverted and then replaced, thereby changing the orientation of the latching members and allowing a right or left handed user to operate the device 10. Furthermore, other configurations of the first and second latching members 40, 50 maybe used in place of the above described latching members.

Figure 6:
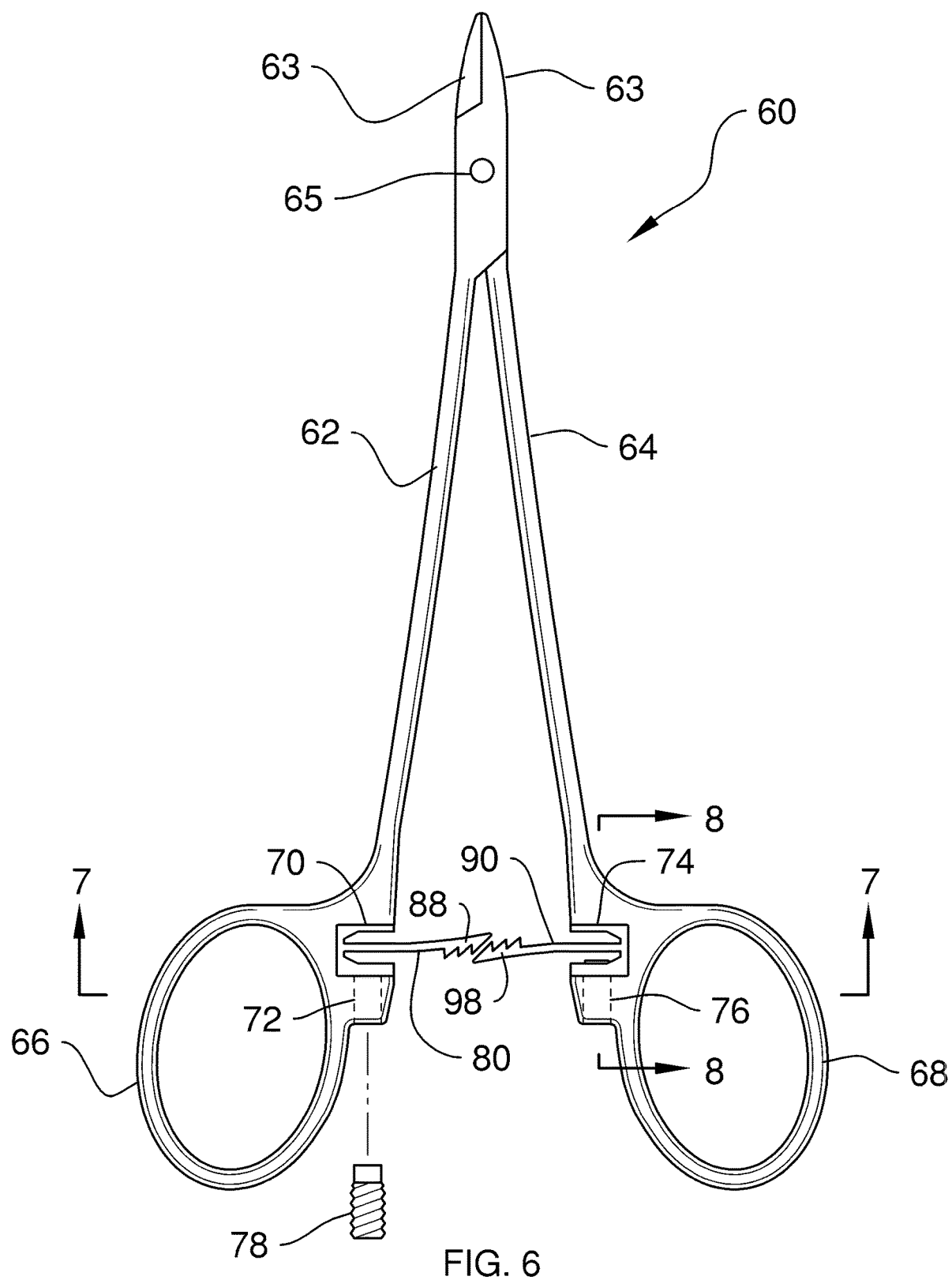
FIG. 6 is a front plane view of a second alternate embodiment of the ambidextrous locking clamp system of the present technology.

Referring now to FIG. 6, a second alternate embodiment of the ambidextrous locking clamp system of the present technology is shown and generally designated by the reference numeral 60. More particularly, the ambidextrous locking clamp system 60 has a first elongated member 62 and a second elongated member 64 each having a working head 63, wherein the working heads can be, but not limited to, a gripping jaw or a cutting edge. The second elongated member 64 is connected to the first elongate member 62 via a hinge 65. The first and second elongated members 62, 64 each have a corresponding finger engaging member 66, 68 located opposite of their respective working heads 63. A first latching member 80 and a second latching member 90 are interchangeably and slidably received in a notch 70 located in the first finger engaging member 66, and in a notch 74 located in the second finger engaging member 68. The notches 70, 74 are orientated so as to face each other. Additionally, a retaining pin 78 is used to secure the latching members 80, 90 in their respective notches 70, 74, through a threaded bore 72 located adjacent the notch 70 and a threaded bore 76 located adjacent the notch 74. The threaded bores 72, 76 are substantially perpendicular with their respective adjacent notches 70, 74. The threaded bores 72, 76 are in communication with their respective notches 70, 74.

Figure 7:
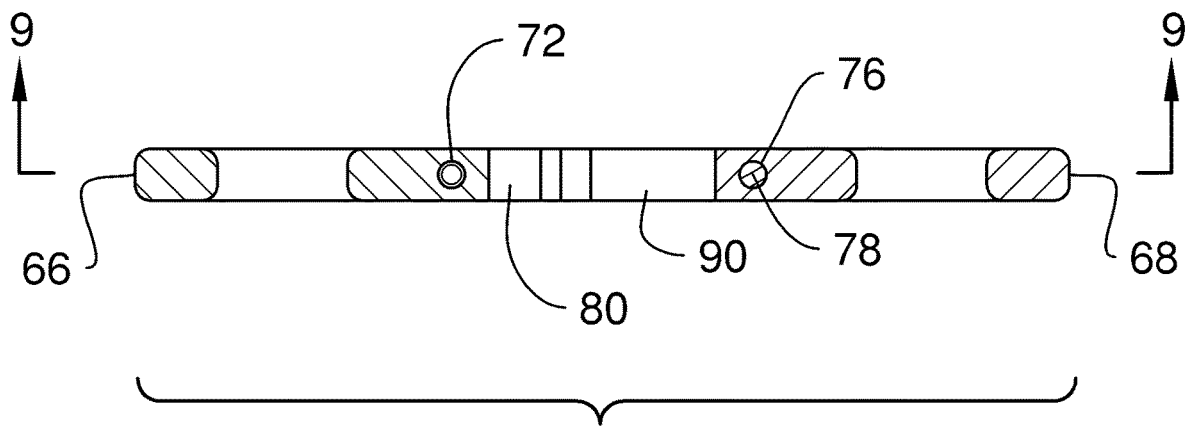
FIG. 7 is an enlarged cross-sectional view of the embodiment in FIG. 6 taken along cross-section line 7-7.

FIG. 7 illustrates the bore 72 without the retaining pin, while bore 76 has the retaining pin 78 therein.

Figure 8:
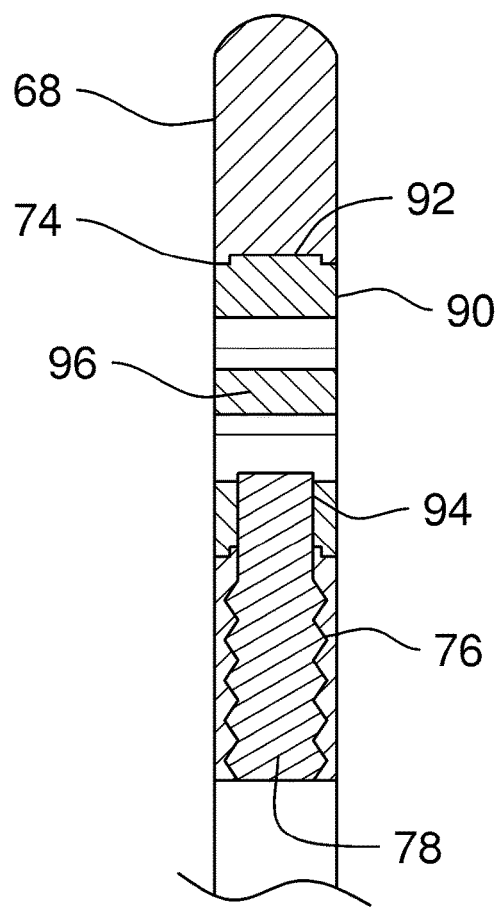
FIG. 8 is an enlarged cross-sectional view of the embodiment in FIG. 6 taken along cross-section line 8-8.

It should be understood that only finger engaging member 68 is shown in FIG. 8 and described herewith, and that latching members 80, 90 can be used with either finger engaging members 66, 68. The latching member 90 features a detent 92 on a first side of the latching member that corresponds to a top side of the notch 74. The detent 92 protrudes into the corresponding top side of the notch 74, allowing the first and second latching members 80, 90 to slide in the notch 74, but at the same time not allowing the latching members to be pulled out of the notch 74 in a direction perpendicular to the sliding motion. FIG. 8 also illustrates the retaining pin 78 threadably retained in the threaded bore 76. The retaining pin 78 has a non-threaded tip which is received within an aperture 94 located through a second side of the latching member 90 opposite the detent 92. The retaining pin 78 secures the latching member 90 in the notch 74, preventing the latching member from being removed from the slot. The second side of the latch member 90 is configured to receive a detent protruding from a bottom side of the notch 74.

Figure 9:
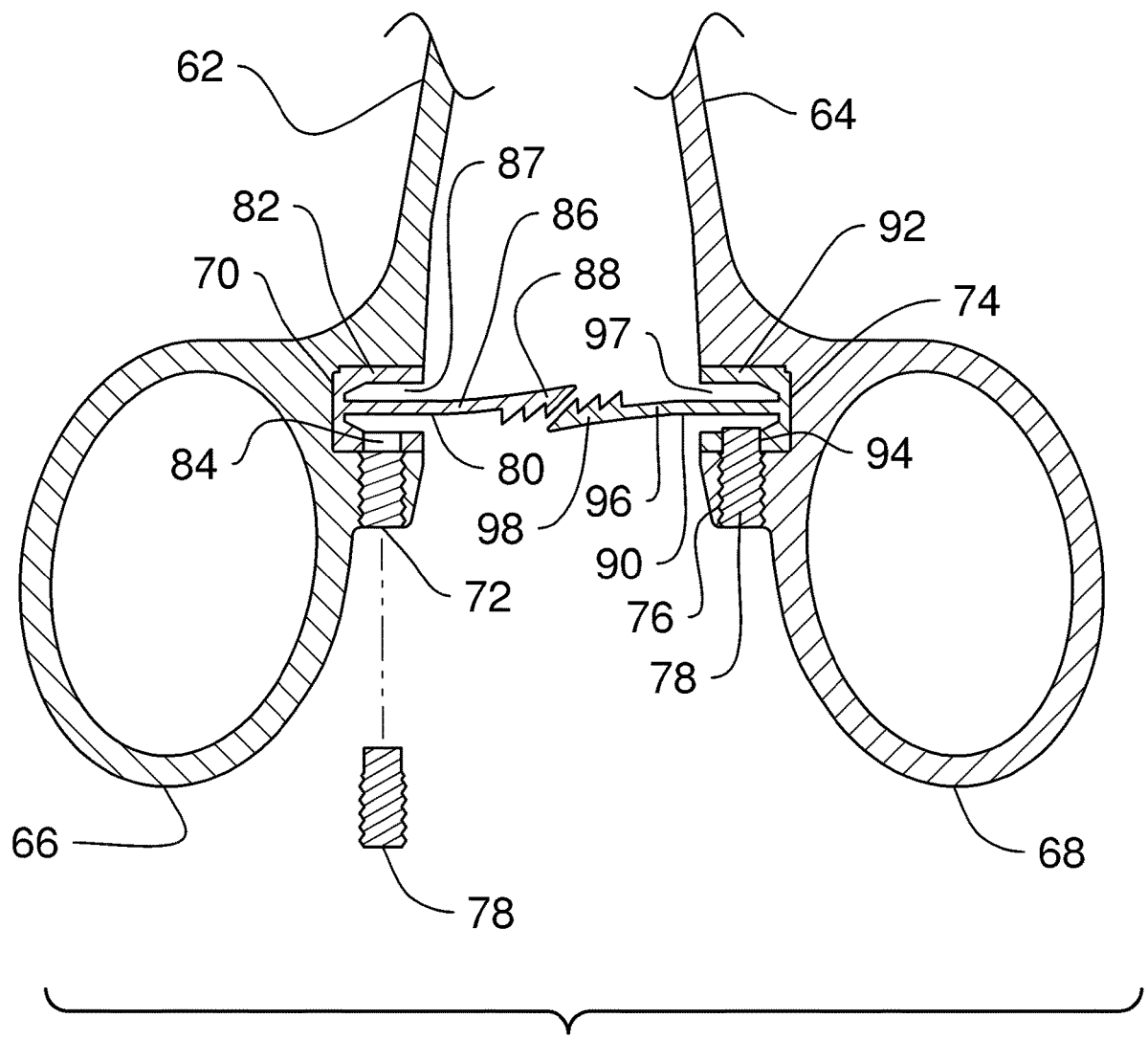
FIG. 9 is an enlarged cross-sectional view of of the embodiment in FIG. 7 taken along cross-section line 9-9.

FIG. 9 best illustrates one possible configuration of the first and second latching members 80, 90 in relation to their respective finger engaging members 66, 68. The first latching member 80 has an elongated flexible arm 86 with a ratcheting head 88 featuring a plurality of ratcheting teeth thereon, a detent 82, and an aperture 84. The detent 82 protrudes into a corresponding top side of notch 70, 74, as described above. The aperture 84 is located on a second side opposite the detent 82 and is aligned with the threaded bore 72, 76 when positioned in its respective notch 70, 74. The aperture 84 is adapted to receive the tip of the retaining pin 78 therethrough or therein when the retaining pin is threaded in the bore 72, 76. The flexible arm 86 is positioned between the detent 82 and the aperture 84 sides of the latching member 80 so as to extend through a first latching member notch 87 defined in the first latching member 80 between the detent 82 and the aperture 84 sides.

The second latching member 90 has an elongated flexible arm 96 with a ratcheting head 98 featuring a plurality of teeth thereon, the detent 92, and the aperture 94. The detent 92 protrudes into a corresponding top side of notch 70, 74, as described above. The aperture 94 is located opposite the detent 92 and is aligned with the threaded bore 72, 76 when positioned in its respective notch 70, 74. The aperture 94 is adapted to receive the tip of the retaining pin 78 therethrough or therein when the retaining pin is threaded in the bore 72, 76. The flexible arm 96 is positioned between the detent 92 and the aperture 94 sides of the latching member 90 so as to extend through a second latching member notch 97 defined in the second latching member 90 between the detent 92 and the aperture 94 sides. The ratcheting heads 88, 98 are adapted to join and lock together when engaged by squeezing the finger engaging members 66, 68 together. The teeth are able to disengage when pulled apart by flexing the first and second elongated members 62, 64 when an opposing perpendicular force in either direction is applied to the finger engaging members 66, 68 by pushing with the thumb and pulling with the fingers of the operating hand thereby separating the parallel engaged teeth.

It can be appreciated that retaining pins 78 are identical and interchangeable, and that the first and second latching members 80, 90 are interchangeable with notches 70, 74. It can also be appreciated that the ambidextrous locking clamp system 60 can be used with either the left or right hand with identical methods of separating and disengaging the teeth of ratcheting heads 88, 98.

The first and second latching members 80, 90 are symmetrical so that they may be removed and interchanged with each other, and then replaced, thereby changing the orientation of the latching members of device 60.

Figure 10:
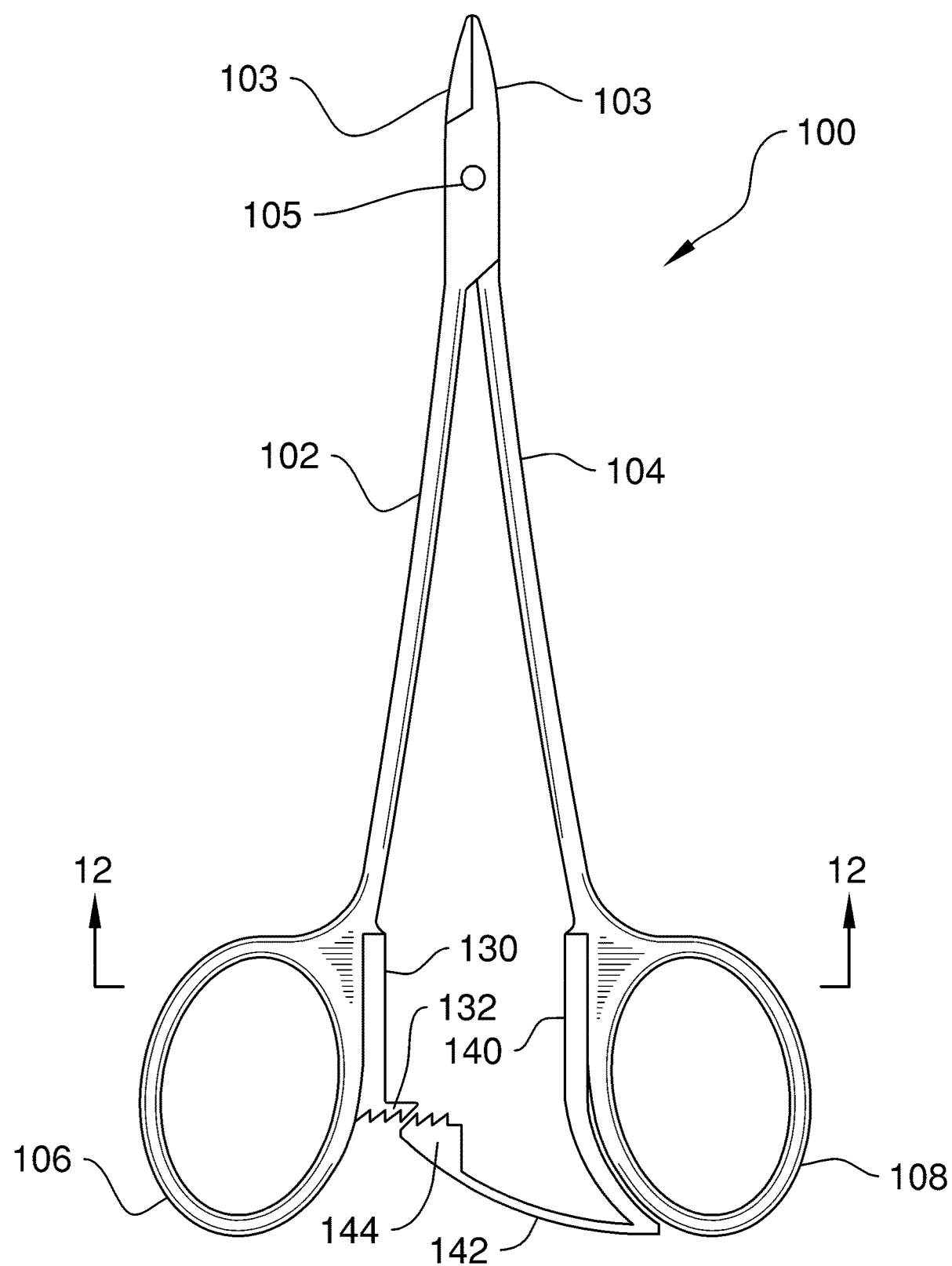
FIG. 10 is a front plane view of a third alternate embodiment of the ambidextrous locking clamp system of the present technology.

Referring now to FIG. 10, a third alternate embodiment of the ambidextrous locking clamp system of the present technology is shown and generally designated by the reference numeral 100. More particularly, the ambidextrous locking clamp system 100 has a first elongated member 102 and a second elongated member 104 each having a working head 103, wherein the working heads can be, but not limited to, a gripping jaw or a cutting edge. The second elongated member 104 is connected to the first elongate member 102 via a hinge 105. The first and second elongated members 102, 104 have a corresponding finger engaging member 106, 108 located opposite of the working heads 103, wherein each finger engaging member can slidably receive a first latching member 130 or a second latching member 140. The first latching member 130 has a ratcheting head 132 featuring ratcheting teeth thereon, and the second latching member 140 has a flexible arm 142 extending out therefrom, and a ratcheting head 144 located at the free end of the flexible arm 142. The ratcheting head 144 features ratcheting teeth thereon adapted to engage with the ratcheting teeth of the ratcheting head 132.

Figure 11:
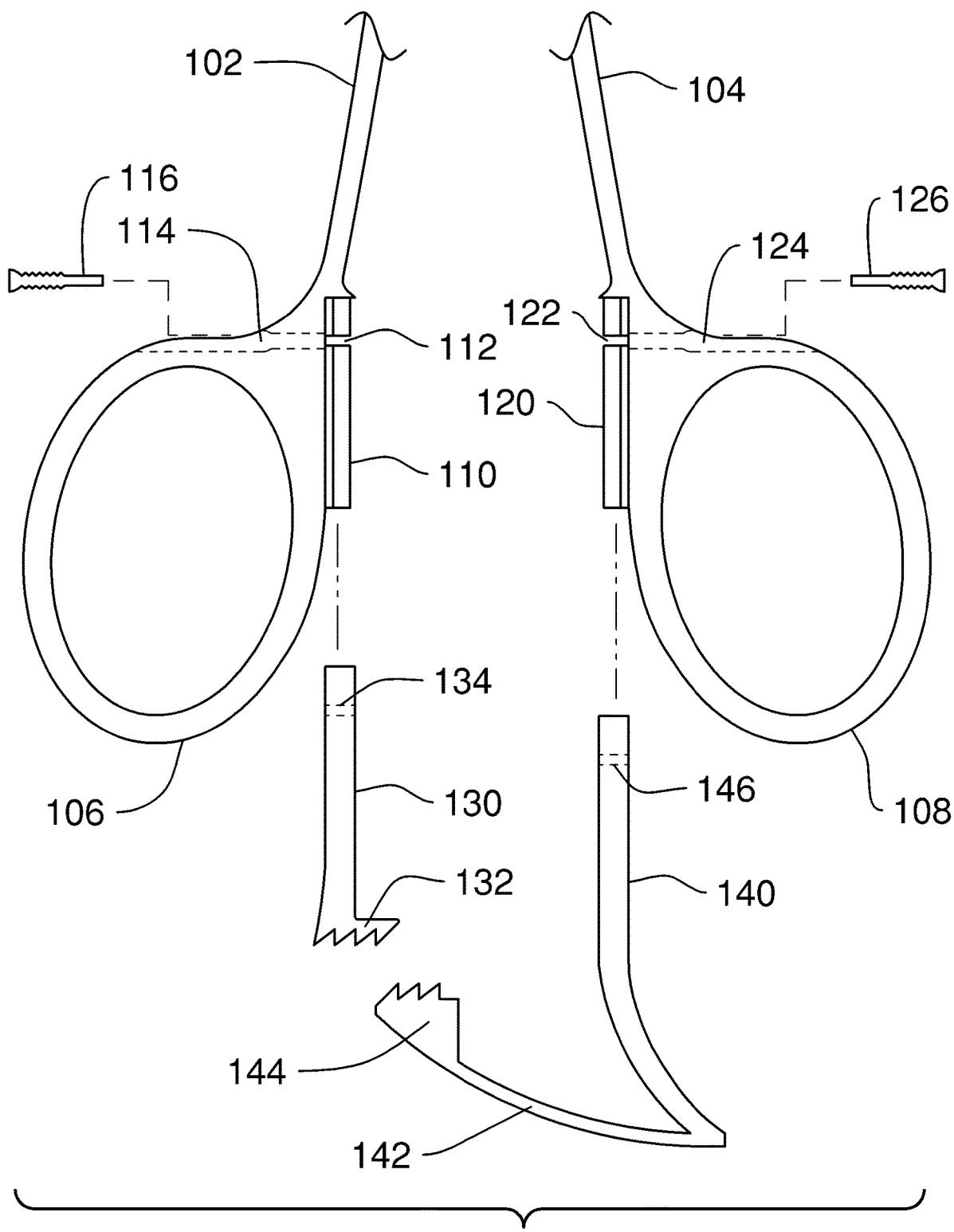
FIG. 11 is an exploded front plane view of the embodiment in FIG. 10.

The finger engaging member 106 has a threaded bore 114, and a protrusion 110 extending out from the finger engaging member 106 perpendicular to the threaded bore 114. The protrusion 110 features a notch 112 aligned with the bore 114. The bore 114 and the notch 112 are adapted and configured to receive a retaining pin 116 therethrough. The retaining pin 116 is threaded and has a non-threaded tip, wherein the tip is adapted to be received through the notch 112. The protrusion 110 is adapted to slidably receive latching members 130, 140. The finger engaging member 108 has a threaded bore 124, and a protrusion 120 extending out from the finger engaging member 108 perpendicular to the threaded bore 124. The protrusion 120 features a notch 122 aligned with the bore 124. The bore 124 and the notch 122 are adapted and configured to receive a retaining pin 126 therethrough. The retaining pin 126 is threaded and has a non-threaded tip, wherein the tip is adapted to be received through the notch 122. The protrusion 120 is adapted to slidably receive latching members 130, 140. It can be appreciated that retaining pins 116, 126 are identical and interchangeable. FIG. 11 is an exploded view best illustrating the above configuration.

Figure 12:
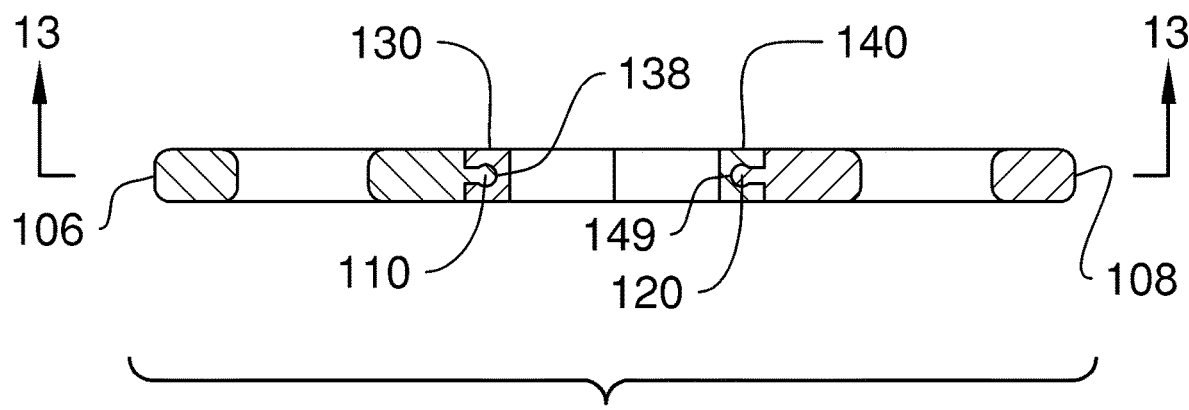
FIG. 12 is an enlarged cross-sectional view of the embodiment in FIG. 10 taken along cross-section line 12-12.

The latching members 130, 140 each have a channel 138, 149 running the length of their respective latching members. The channels 138, 149 are adapted and configured to slide on and be retained by the protrusions 110, 120 extending out from their respective finger engaging members 106, 108. The configuration of the channels 138, 149 and the protrusions 110, 120 allow the latching members 130, 140 to slide over the protrusion, but at the same time not allowing the latching members to be pulled off the protrusions in a direction perpendicular to the sliding motion. FIG. 12 best illustrates one possible example of the channel and protrusion configuration.

Figure 13:
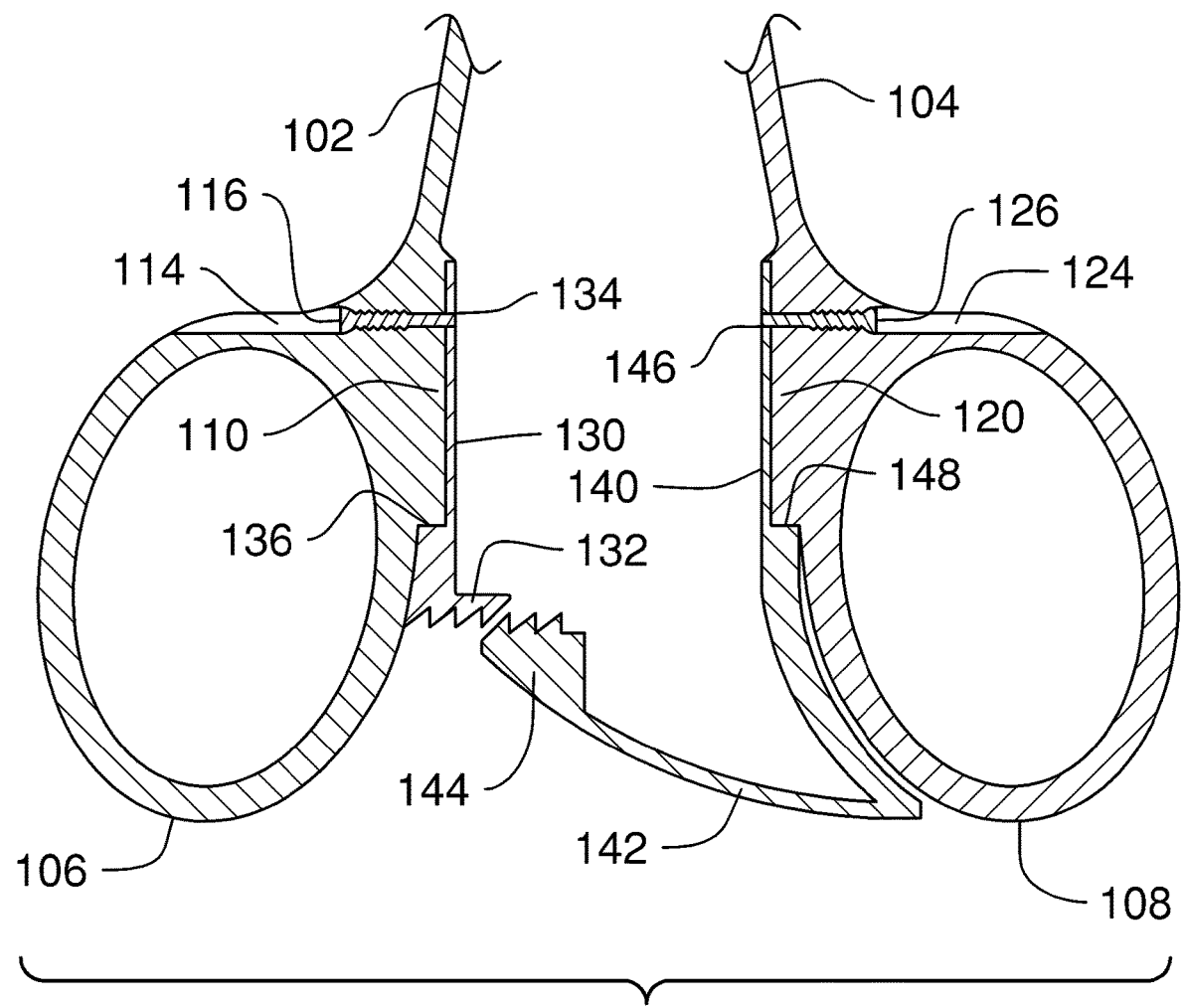
FIG. 13 is an enlarged cross-sectional view of the embodiment in FIG. 12 taken along cross-section line 13-13.

FIG. 13 best illustrates one possible configuration of the first and second latching members 130, 140 in relation to their respective finger engaging members 106, 108. The first latching member 130 has the ratcheting head 132 featuring a plurality of ratcheting teeth thereon, a stop 136, and an aperture 134. The stop 136 is perpendicular to the longitudinal axis of the latching member 130 and it is adapted to abut against a free end of it respective protrusion 110, 120. The aperture 134 is located opposite the stop 136 and is aligned with the threaded bore 114, 124 and the notch 112, 122 when positioned on its respective protrusion 110, 120. The aperture 134 is adapted to receive the tip of the retaining pin 116, 126 therethrough or therein when the retaining pin is threaded in the bore 114, 124, through notch 112, 122, and through aperture 134. The second latching member 140 has the flexible arm 142, the ratcheting head 144 featuring a plurality of ratcheting teeth thereon, a stop 148, and an aperture 146. The stop 148 is perpendicular to the longitudinal axis of the latching member 140 and it is adapted to abut against a free end of it respective protrusion 110, 120. The aperture 146 is located opposite the stop 148 and is aligned with the threaded bore 114, 124 and the notch 112, 122 when positioned on its respective protrusion 110, 120. The aperture 146 is adapted to receive the tip of the retaining pin 116, 126 therethrough or therein when the retaining pin is threaded in the bore 114, 124, and through notch 112, 122 and aperture 146. The flexible arm 142 extends out from a section of the latching member 140 extending past the ratcheting head 132 of the first latching member 130, when both latching members 130, 140 are attached to their respective protrusions 110, 120. The flexible arm 142 has a generally arcuate shape curving upwardly toward the ratcheting head 132 of the first latching member 130. This extension of the second latching member 140 has a shape that corresponds to the shape of the finger engaging member 106, 108. The ratcheting head 144 is attached to the free end of the flexible arm 142, thereby allowing the ratcheting head 144 to free travel with the flexing of the flexible arm 142. The ratcheting heads 132, 144 are adapted to join and lock together when engaged by squeezing the finger engaging members 106, 108 together. The teeth are able to disengage when pulled apart by flexing the first and second elongated members 102, 104 when an opposing perpendicular force is applied to the finger engaging members 106, 108 by pushing with the thumb and pulling with the fingers of the operating hand thereby separating the parallel engaged teeth.

It can be appreciated that retaining pins 116, 126 are identical and interchangeable, and that the channels 138, 149 of first and second latching members 130, 140 are identical interchangeable with protrusions 110, 120. It can also be appreciated that the ambidextrous locking clamp system 100 can be used with either the left or right hand with identical methods of separating and disengaging the teeth of ratcheting heads 132, 144.

The channels 138, 149, apertures 134, 146, and stop 136, 148 of the first and second latching members 130, 140 are symmetrical so that they may be removed, inverted and then replaced, thereby changing the orientation of the latching members of device 100. Furthermore, other configurations of the first and second latching members 130, 140 may be used in place of the above described latching members.

Figure 14:
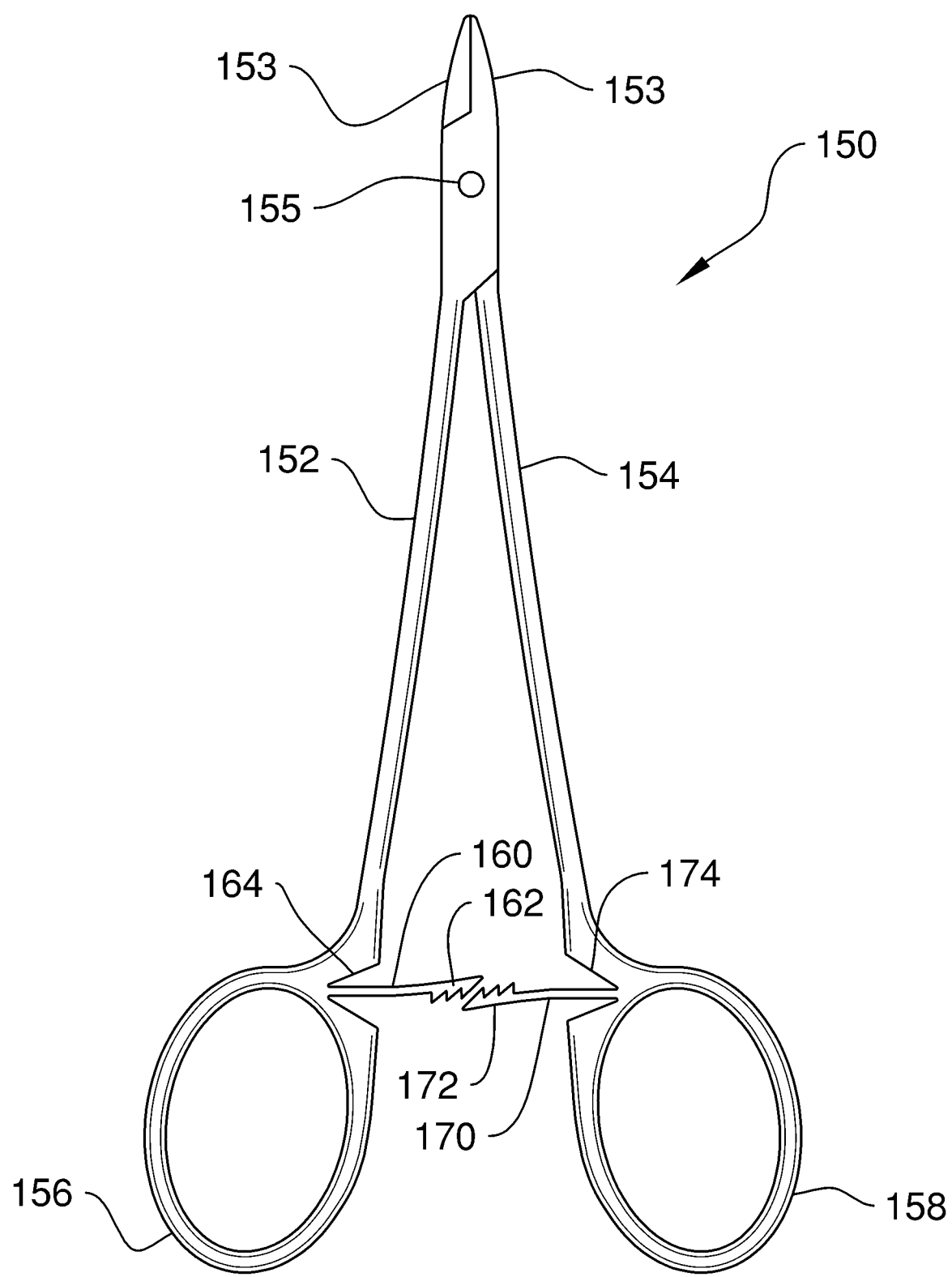
FIG. 14 is a front plane view of a fourth alternate embodiment of the present technology.

Referring now to FIG. 14, a fourth alternate embodiment of the ambidextrous locking clamp system of the present technology is shown and generally designated by the reference numeral 150. More particularly, the ambidextrous locking clamp system 150 has a first elongated member 152 and a second elongated member 154 each having a working head 153, wherein the working heads can be, but not limited to, a gripping jaw or a cutting edge. The second elongated member 154 is connected to the first elongate member 152 via a hinge 155. The first and second elongated members 152, 154 each have a corresponding finger engaging member 156, 158 located opposite of their respective working heads 153. The first finger engaging member 156 has a latching member 160 extending out from a notch 164, and a ratcheting head 162 located at the free end of the latching member 160. The ratcheting head 162 features ratcheting teeth thereon. The second finger engaging member 158 has a latching member 170 extending out from a notch 174, and a ratcheting head 172 located at the free end of the latching member 170. The ratcheting head 172 features ratcheting teeth thereon adapted to engage with the ratcheting teeth of the ratcheting head 162 when the first and second finger engaging members 156, 158 are squeezed together.

Figure 15:
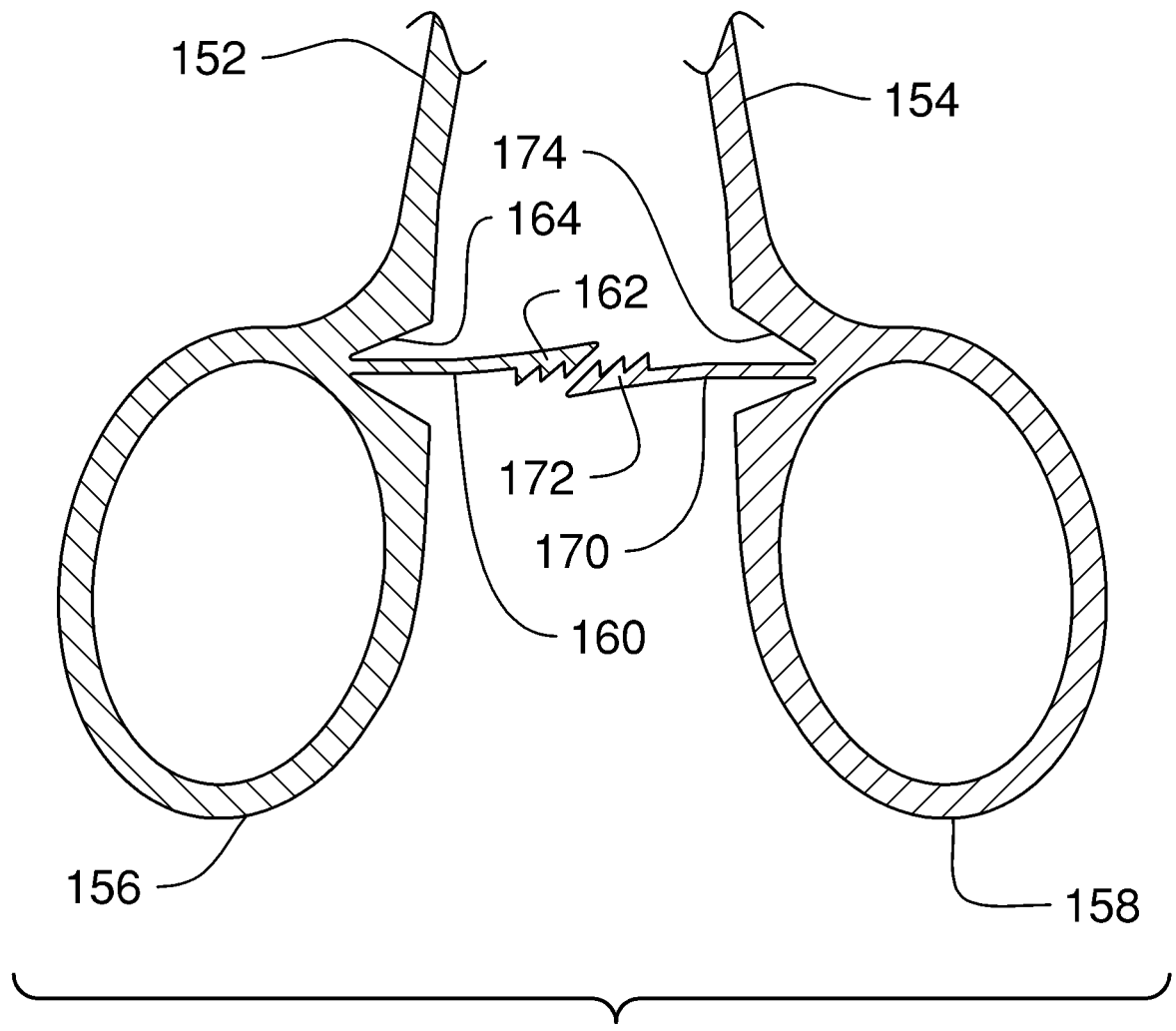
FIG. 15 is an enlarged cross-sectional view of the embodiment in FIG. 14.

As illustrated in FIG. 15, the first and second finger engaging members 156, 158, the latching members 160, 170, and the notches 164, 174 are symmetrical and mirror images of each other. The latching member 160 of the first finger engaging member 156 is a flexible arm that extends out from the notch 164 toward the second finger engaging member 158. The notch 164 can have any geometric shape, but preferably a V-shape with the latching member 160 extending out from the central interior of the V-shaped notch. The latching member 170 of the second finger engaging member 158 is a flexible arm that extends out from the notch 174 toward the first finger engaging member 156. The notch 174 can have any geometric shape, but preferably a V-shape with the latching member 170 extending out from the central interior of the V-shaped notch.

The ratcheting heads 162, 172 are adapted to join and lock together when engaged by squeezing the finger engaging members 156, 158 together. The teeth are able to disengage when pulled apart by flexing the first and second elongated members 152, 154 when an opposing force is applied to the finger engaging members 156, 158 in a perpendicular movement in either direction by pushing with the thumb and pulling with the fingers of the operating hand thereby separating the parallel engaged teeth.

It can be appreciated that the ambidextrous locking clamp system 150 can be used with either the left or right hand with identical methods of separating and disengaging the teeth of ratcheting heads 162, 172 and/or with the flexing of the elongated members in a perpendicular movement in either direction.

Figure 16:
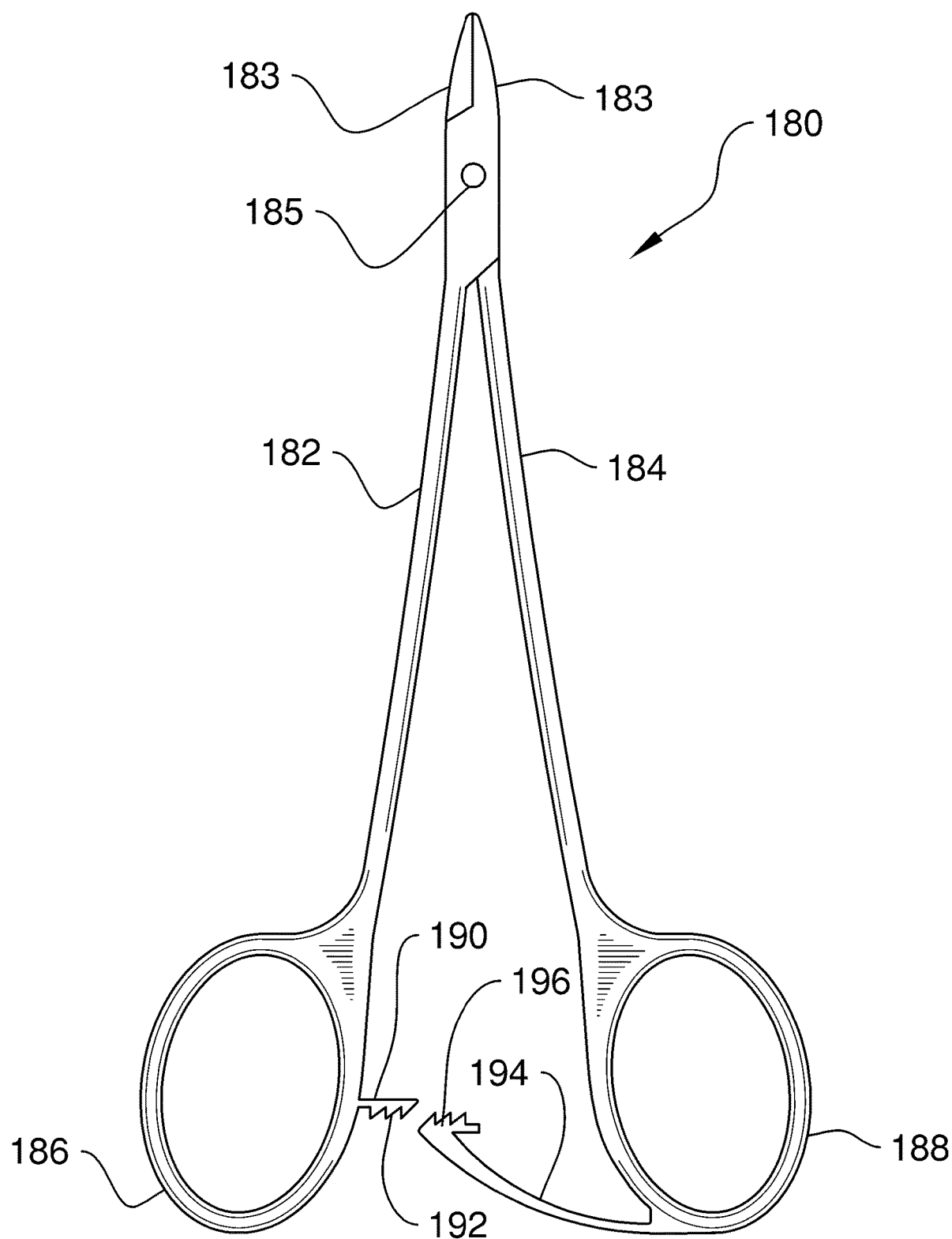
FIG. 16 is a front plane view of a fifth alternate embodiment of the present technology.

Referring now to FIG. 16, a fifth alternate embodiment of the ambidextrous locking clamp system of the present technology is shown and generally designated by the reference numeral 180. More particularly, the ambidextrous locking clamp system 180 has a first elongated member 182 and a second elongated member 184 each having a working head 183, wherein the working heads can be, but not limited to, a gripping jaw or a cutting edge. The second elongated member 184 is connected to the first elongate member 182 via a hinge 185. The first and second elongated members 182, 184 each have a corresponding finger engaging member 186, 188 located opposite of their respective working heads 183. The first finger engaging member 186 has a latching member 190 extending out therefrom, and a ratcheting head 192 located at the free end of the latching member 190. The ratcheting head 192 features ratcheting teeth thereon. The second finger engaging member 188 has a latching member 194 extending out therefrom, and a ratcheting head 196 located at the free end of the latching member 194. The ratcheting head 196 features ratcheting teeth thereon adapted to engage with the ratcheting teeth of the ratcheting head 192 when the first and second finger engaging members 186, 188 are squeezed together.

Figure 17:
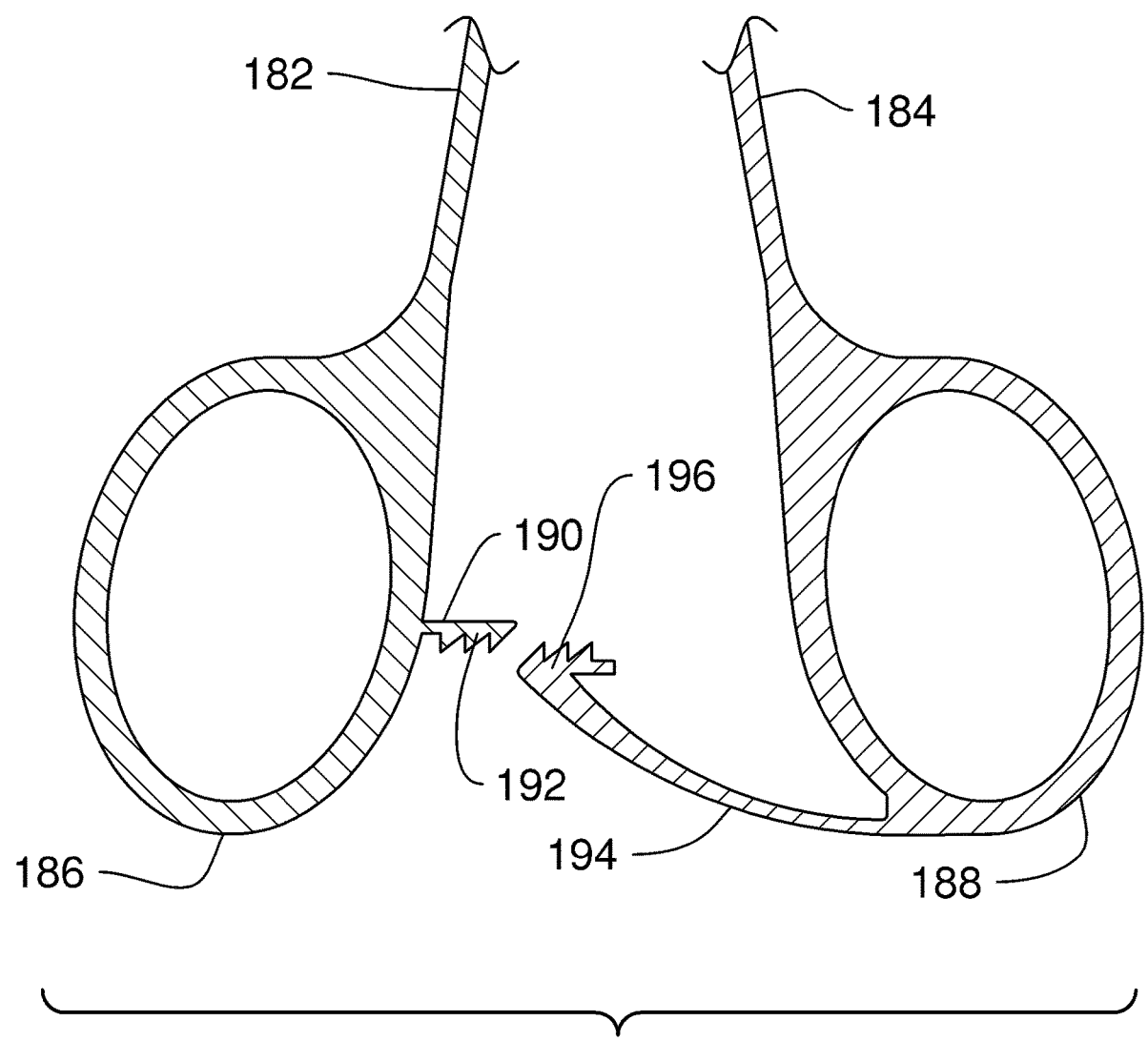
FIG. 17 is an enlarged cross-sectional view of the embodiment in FIG. 16.

As illustrated in FIG. 17, the latching member 190 of the first finger engaging member 186 extends out from the interior of the first finger engaging member toward the second finger engaging member 188. The latching member 194 of the second finger engaging member 188 is a flexible arm that extends outwardly and upwardly from the bottom of the second finger engaging member 188 and below the latching member 190 toward the first finger engaging member 186. The ratcheting head 196 is located on the free end of the flexible arm latching member 194. The flexible arm latching member 194 tapers with the thickest part being attached to the ratcheting head and the thinnest part being attached to the bottom of the second finger engaging member 188, and has a generally arcuate shape. Thereby allowing the latching member 194 to have a more degree of flexibility at its second finger engaging member attachment point, and increasing the travel length of ratcheting head 196.

The ratcheting heads 192, 196 are adapted to join and lock together when engaged by squeezing the finger engaging members 186, 188 together. The teeth are able to disengage when pulled apart by flexing the first and second elongated members 182, 184 when an opposing force is applied to the finger engaging members 186, 188 by pushing with the thumb and pulling with the fingers of the operating hand thereby separating the parallel engaged teeth.

It can be appreciated that the ambidextrous locking clamp system 180 can be used with either the left or right hand with identical methods of separating and disengaging the teeth of ratcheting heads 192, 196.

Figure 18:
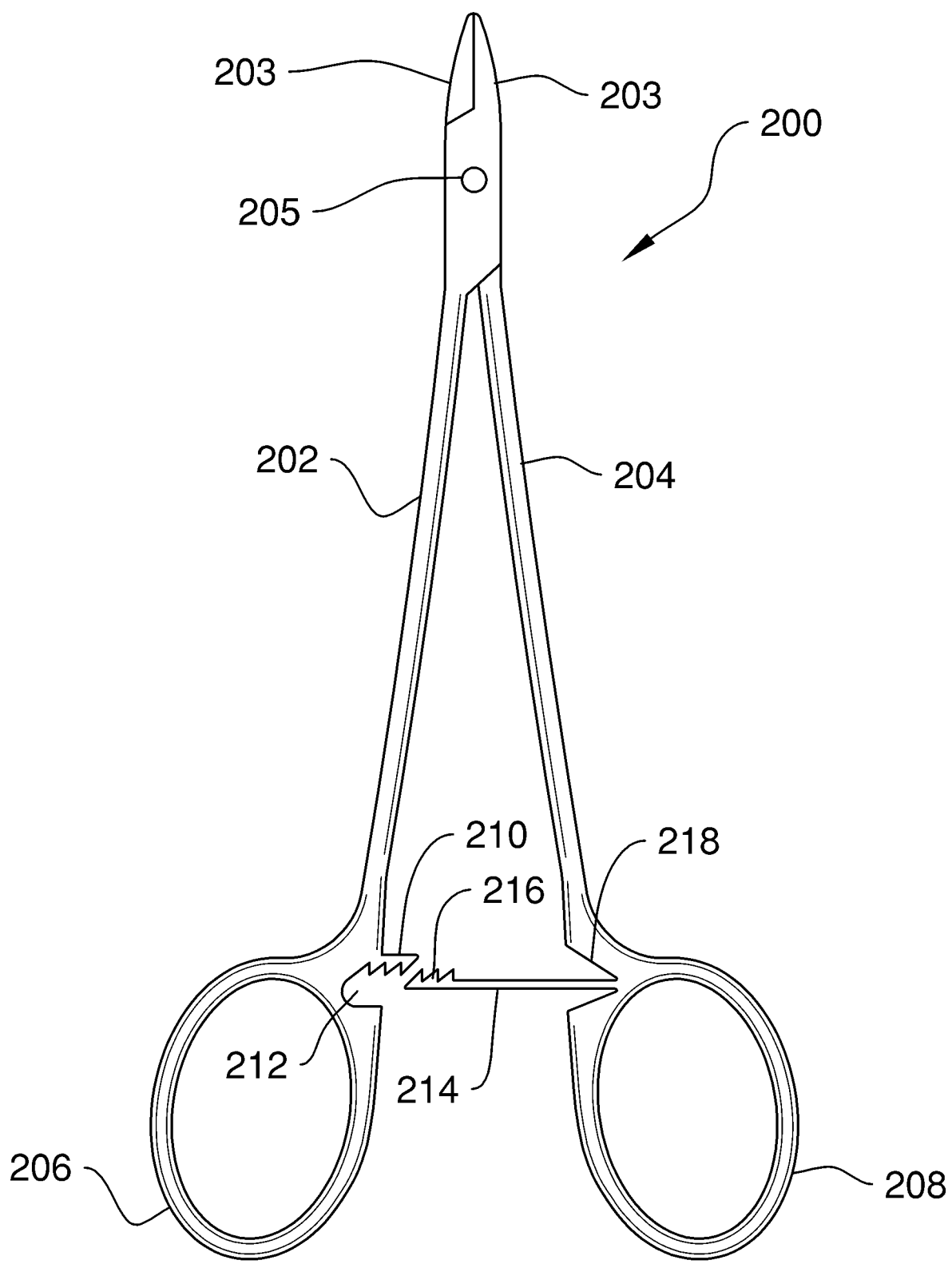
FIG. 18 is a front plane view of a sixth alternate embodiment of the present technology.

Referring now to FIG. 18, a sixth alternate embodiment of the ambidextrous locking clamp system of the present technology is shown and generally designated by the reference numeral 200. More particularly, the ambidextrous locking clamp system 200 has a first elongated member 202 and a second elongated member 204 each having a working head 203, wherein the working heads can be, but not limited to, a gripping jaw or a cutting edge. The second elongated member 204 is connected to the first elongate member 202 via a hinge 205. The first and second elongated members 202, 204 each have a corresponding finger engaging member 206, 208 located opposite of their respective working heads 203. The first finger engaging member 206 has a latching member 210 extending out therefrom, and a notch 212 adjacent the latching member 210. The latching member 210 features ratcheting teeth thereon. The second finger engaging member 208 has a latching member 214 extending out from a notch 218, and a ratcheting head 216 located at the free end of the latching member 214. The ratcheting head 216 features ratcheting teeth thereon adapted to engage with the ratcheting teeth of the latching member 210 when the first and second finger engaging members 206, 208 are squeezed together.

Figure 19:
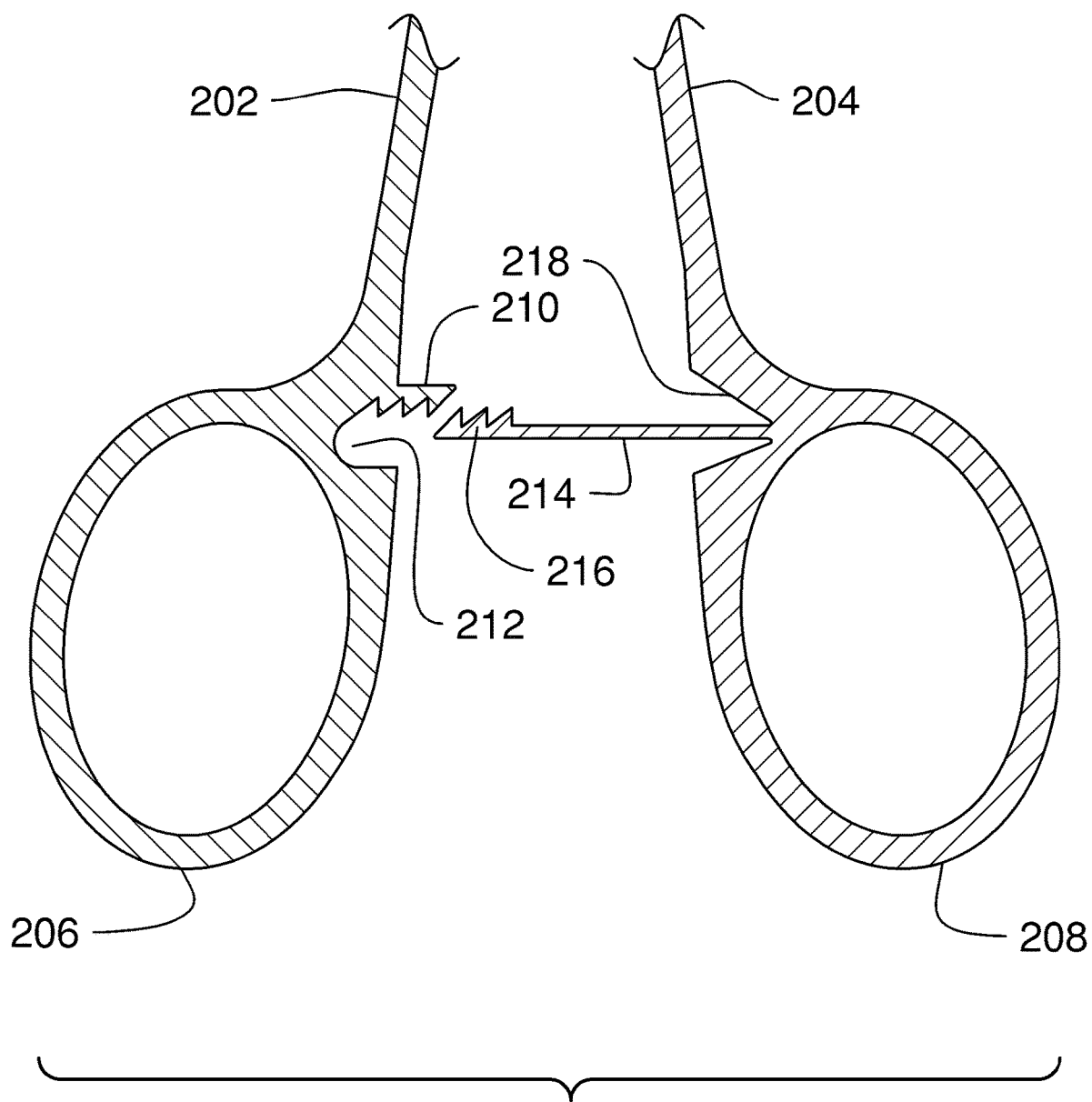
FIG. 19 is an enlarged cross-sectional view of the embodiment in 18.

As illustrated in FIG. 19, the latching member 210 of the first finger engaging member 206 extends out from the first finger engaging member toward the second finger engaging member 208. The notch 212 can have any geometric shape, but preferably a U-shape with the latching member 210 being positioned directly above or below and adjacent to the U-shaped notch. The notch 212 being configured to receive the ratcheting head 216 of the latching member 214 of the second finger engaging member 208, and allowing for the ratcheting head 216 to disengage from the first latching member 210. The latching member 214 of the second finger engaging member 208 is a flexible arm that extends out from the notch 218 toward the first finger engaging member 206. The notch 218 can have any geometric shape, but preferably a V-shape with the latching member 214 extending out from the central interior of the V-shaped notch.

The ratcheting head 216 and the ratcheting teeth of the latching member 210 are adapted to join and lock together when engaged by squeezing the finger engaging members 206, 208 together. The teeth are able to disengage when pulled apart by flexing the first and second elongated members 202, 204 when an opposing force is applied to the finger engaging members 206, 208 by pushing with the thumb and pulling with the fingers of the operating hand thereby separating the parallel engaged teeth.

It can be appreciated that the ambidextrous locking clamp system 200 can be used with either the left or right hand with identical methods of separating and disengaging the teeth of the first latching member 210 and ratcheting head 216.

Figure 20:
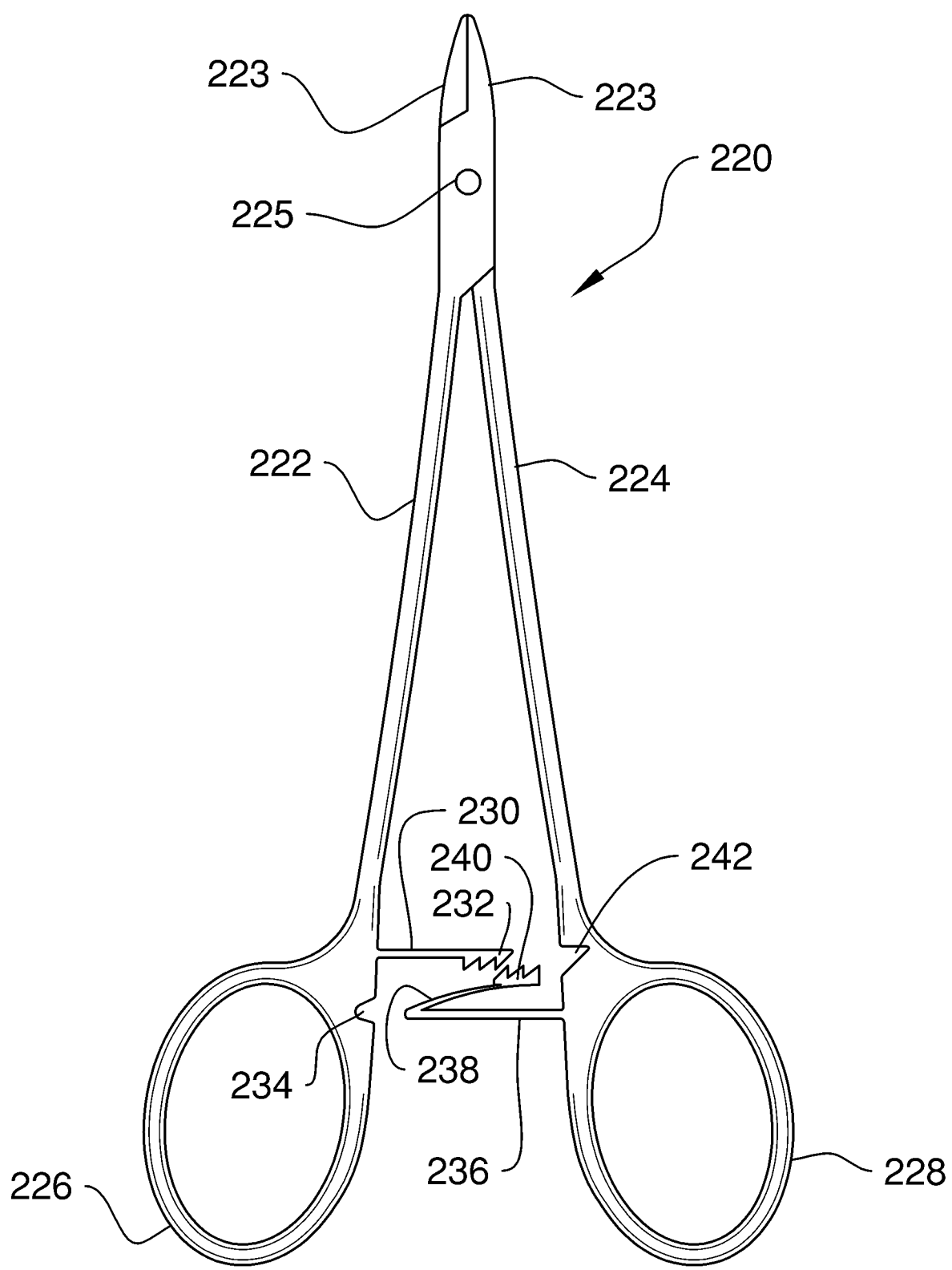
FIG. 20 is a front plane view of a seventh alternate embodiment of the present technology.

Referring now to FIG. 20, a seventh alternate embodiment of the ambidextrous locking clamp system of the present technology is shown and generally designated by the reference numeral 220. More particularly, the ambidextrous locking clamp system 220 has a first elongated member 222 and a second elongated member 224 each having a working head 223, wherein the working heads can be, but not limited to, a gripping jaw or a cutting edge. The second elongated member 224 is connected to the first elongate member 222 via a hinge 225. The first and second elongated members 222, 224 each have a corresponding finger engaging member 226, 228 located opposite of their respective working heads 223. The first finger engaging member 226 has a latching member 230 extending out therefrom, a ratcheting head 232 located at the free end of the latching member 230, and a notch 234. The ratcheting head 232 features ratcheting teeth thereon. The second finger engaging member 228 has a latching member 236 extending out therefrom, a flexible arm 238, a ratcheting head 240, and a notch 242. The ratcheting head 240 features ratcheting teeth thereon adapted to engage with the ratcheting teeth of the ratcheting head 232 when the first and second finger engaging members 226, 228 are squeezed together.

Figure 21:
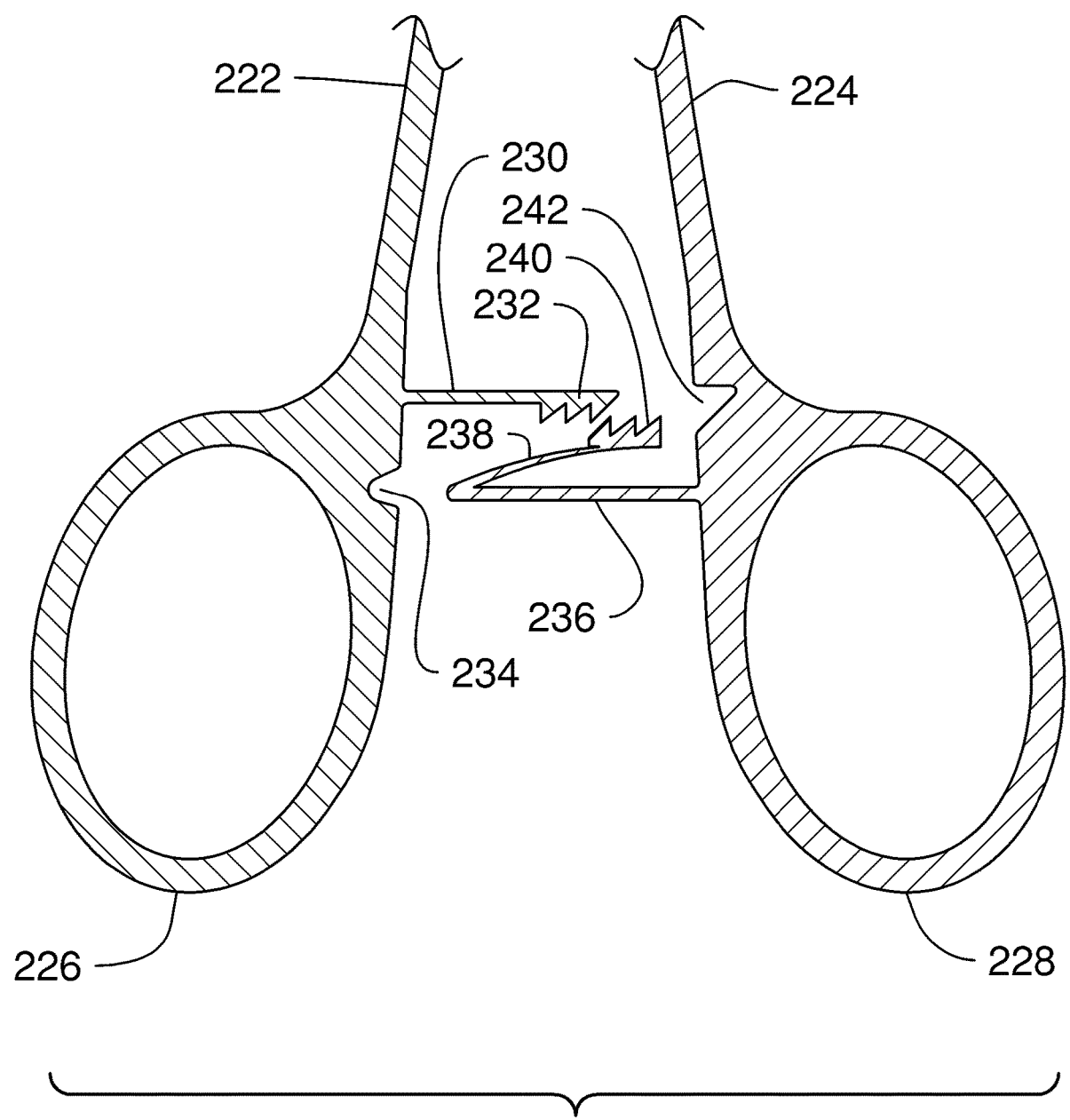
FIG. 21 is an enlarged cross-sectional view of the embodiment in FIG. 20.

As illustrated in FIG. 21, the latching member 230 of the first finger engaging member 226 extends out from the first finger engaging member toward the second finger engaging member 228. The notch 234 can have any geometric shape, but preferably a U-shape aligned with the latching member 236. The latching member 230 is positioned above or below the notch 234. The notch 234 is configured to receive the flexible arm 238 and the latching member 236 attachment point. The flexible arm 238 is attached to the free end of the latching member 236, and the ratcheting head 240 is attached to the free end of the flexible arm 238. The latching member 236 of the second finger engaging member 228 extends out from the second finger engaging member 228 toward the notch 234 of the first finger engaging member 226. The flexible arm 238 extends inwardly and upwardly from the free end of the latching member 236, and has an arcuate shape. The flexible arm 238 allows for the free travel of the ratcheting head 240. The notch 242 is positioned above or below the latching member 236 and is aligned with the latching member 230, and is adapted and configured to receive the ratcheting head 232 of the latching member 230. The notch 242 can have any geometric shape, but preferably a shape that corresponds to the shape of the ratcheting head 232 of the latching member 230.

The ratcheting teeth of the ratcheting head 232 and the ratcheting teeth of the ratcheting head 240 are adapted to join and lock together when engaged by squeezing the finger engaging members 226, 228 together. The teeth are able to disengage when pulled apart by flexing the first and second elongated members 222, 224 when an opposing force is applied to the finger engaging members 226, 228 by pushing with the thumb and pulling with the fingers of the operating hand thereby separating the parallel engaged teeth.

It can be appreciated that the ambidextrous locking clamp system 220 can be used with either the left or right hand with identical methods of separating and disengaging the teeth of ratcheting heads 232, 240.

Figure 22:
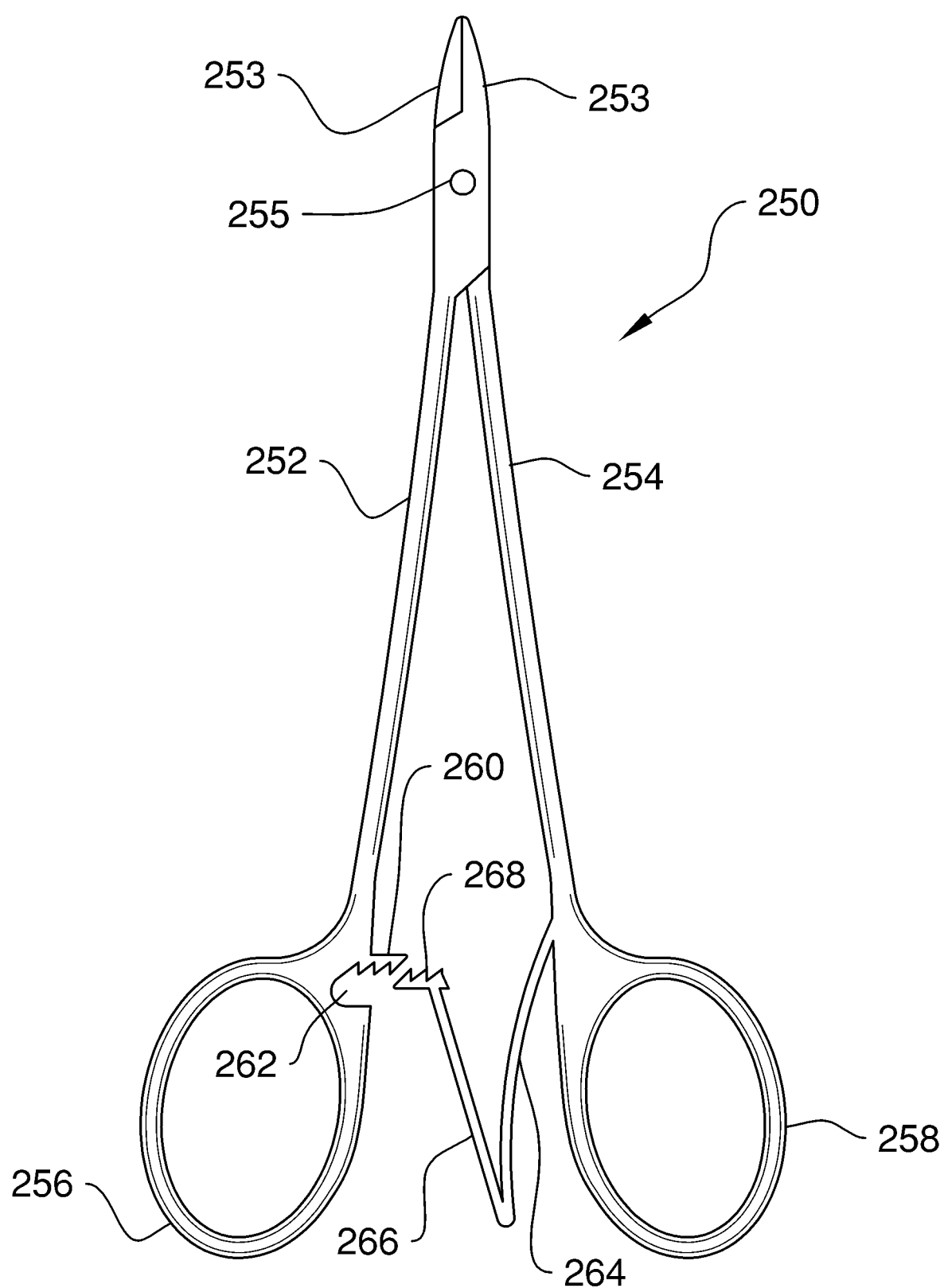
FIG. 22 is a front plane view of an eighth alternate embodiment of the present technology.

Referring now to FIG. 22, an eighth alternate embodiment of the ambidextrous locking clamp system of the present technology is shown and generally designated by the reference numeral 250. More particularly, the ambidextrous locking clamp system 250 has a first elongated member 252 and a second elongated member 254 each having a working head 253, wherein the working heads can be, but not limited to, a gripping jaw or a cutting edge. The second elongated member 254 is connected to the first elongate member 252 via a hinge 255. The first and second elongated members 252, 254 each have a corresponding finger engaging member 256, 258 located opposite of their respective working heads 253. The first finger engaging member 256 has a latching member 260 extending out therefrom, and a notch 262 adjacent the latching member 260. The latching member 260 features ratcheting teeth thereon. The second finger engaging member 258 has a latching member 264 extending out therefrom, an arm 266, and a ratcheting head 268. The ratcheting head 268 features ratcheting teeth thereon adapted to engage with the ratcheting teeth of the latching member 260 when the first and second finger engaging members 256, 258 are squeezed together.

Figure 23:
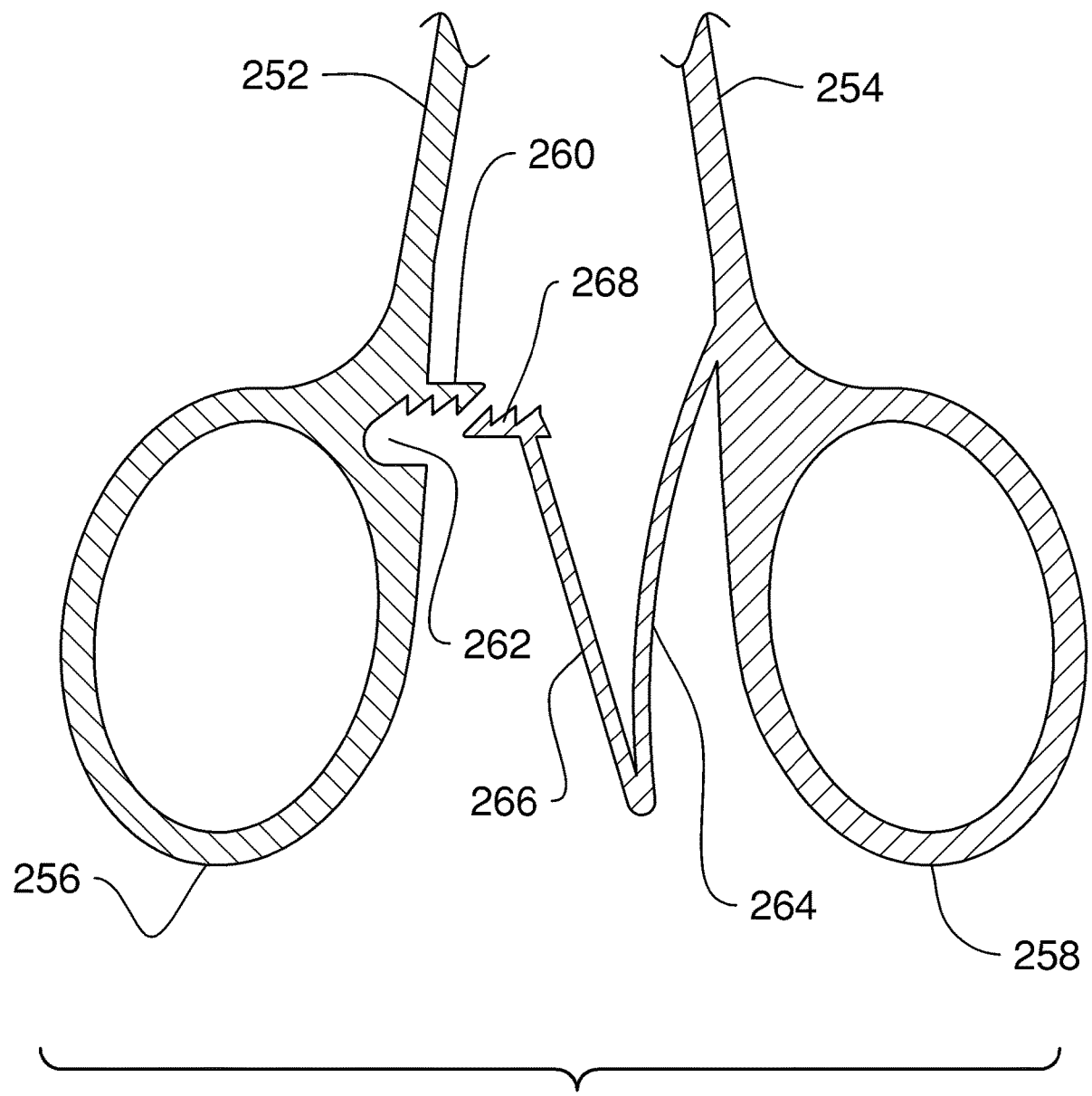
FIG. 23 is an enlarged cross-sectional view of the embodiment in FIG. 22.

As illustrated in FIG. 23, the latching member 260 of the first finger engaging member 256 extends out from the first finger engaging member toward the second finger engaging member 258. The notch 262 can have any geometric shape, but preferably a U-shape with the latching member 260 being positioned directly above or below and adjacent to the U-shaped notch. The notch 262 is aligned with the ratcheting head 268 of the latching member 264, allowing the ratcheting head 268 to disengage from the ratcheting head 260, while received therein. The latching member 264 of the second finger engaging member 258 extends out from the second finger engaging member toward the first finger engaging member 256. The arm 266 is attached to the free end of the latching member 264, and the ratcheting head 268 is attached to the free end of the arm 266. The latching member 264 and the arm 266 are flexible allowing for the free travel of the ratcheting head 268, with respect to the second finger engaging member 258. The latching member 264 extends outwardly and downwardly from the interior of the second finger engaging member 258, and has a generally arcuate shape. The arm 266 extends outwardly and upwardly from the free end of the latching member 264.

The ratcheting teeth of the latching member 260 and the ratcheting teeth of the ratcheting head 268 are adapted to join and lock together when engaged by squeezing the finger engaging members 256, 258 together. The teeth are able to disengage when pulled apart by flexing the first and second elongated members 252, 254 when an opposing force is applied to the finger engaging members 256, 258 by pushing with the thumb and pulling with the fingers of the operating hand thereby separating the parallel engaged teeth.

It can be appreciated that the ambidextrous locking clamp system 250 can be used with either the left or right hand with identical methods of separating and disengaging the teeth of the first latching member 260 and the ratcheting head 268.

Figure 24:
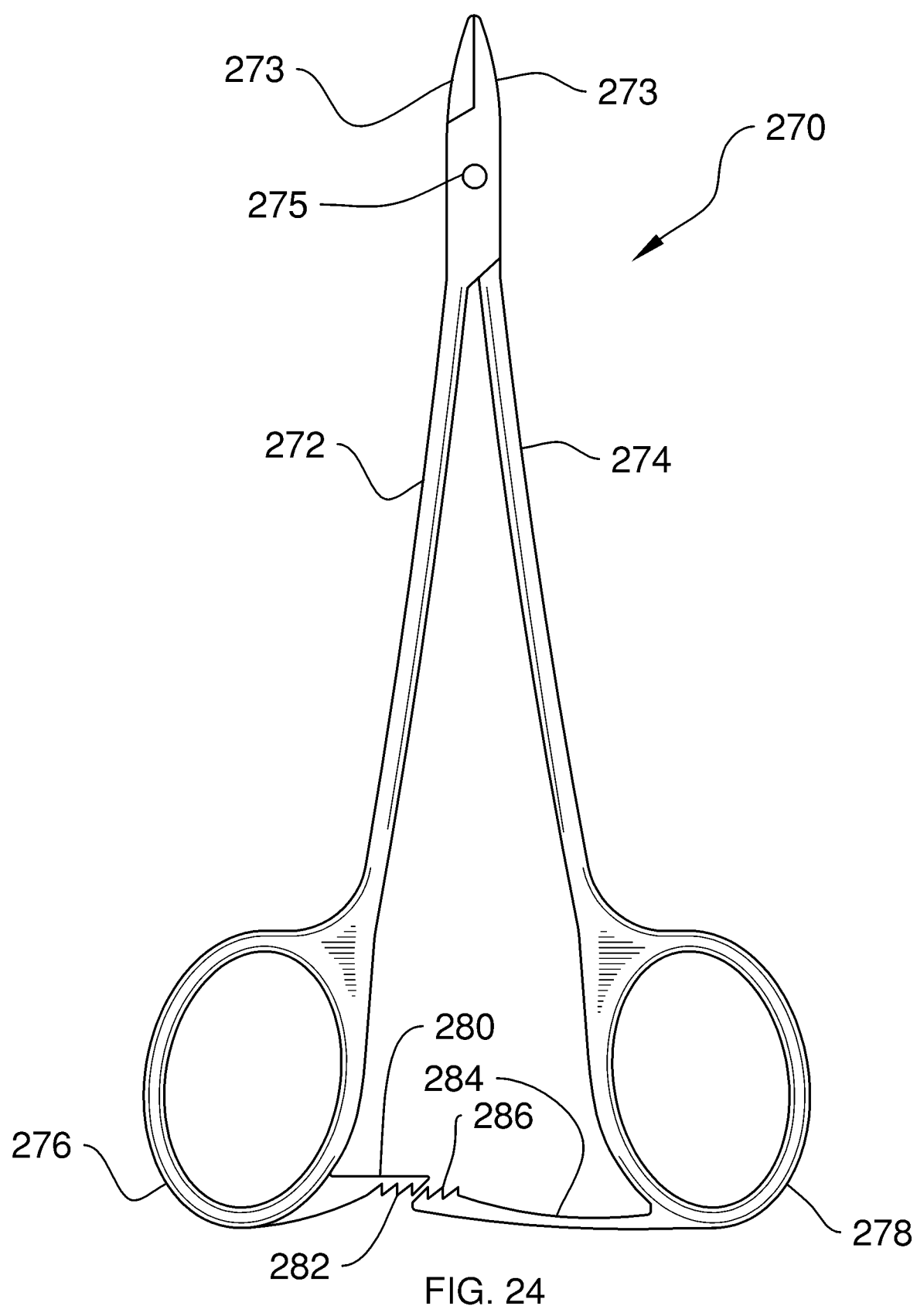
FIG. 24 is a front plane view of a ninth alternate embodiment of the present technology.

Referring now to FIG. 24, a ninth alternate embodiment of the ambidextrous locking clamp system of the present technology is shown and generally designated by the reference numeral 270. More particularly, the ambidextrous locking clamp system 270 has a first elongated member 272 and a second elongated member 274 each having a working head 273, wherein the working heads can be, but not limited to, a gripping jaw or a cutting edge. The second elongated member 274 is connected to the first elongate member 272 via a hinge 275. The first and second elongated members 272, 274 each have a corresponding finger engaging member 276, 278 located opposite of their respective working heads 273. The first finger engaging member 272 has a latching member 280 extending out therefrom, and a ratcheting head 282. The ratcheting head 282 features ratcheting teeth thereon. The second finger engaging member 278 has a latching member 284 extending out therefrom, and a ratcheting head 286. The ratcheting head 286 features ratcheting teeth thereon adapted to engage with the ratcheting teeth of the ratcheting head 282 when the first and second finger engaging members 276, 278 are squeezed together.

Figure 25:
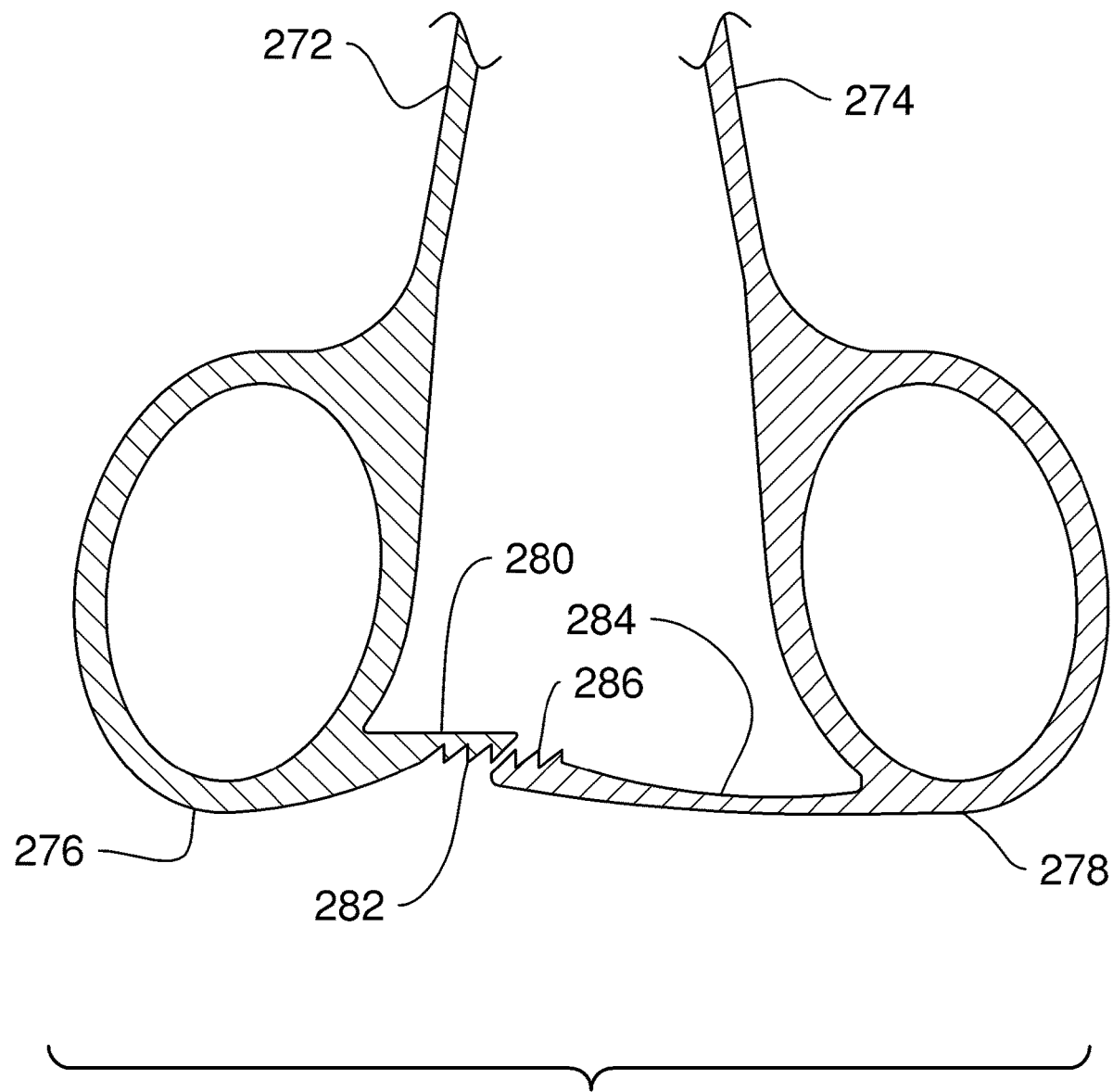
FIG. 25 is an enlarged cross-sectional view of the embodiment in FIG. 25.

As illustrated in FIG. 25, the latching member 280 of the first finger engaging member 276 extends out from the bottom of the first finger engaging member toward the second finger engaging member 278. The latching member 284 of the second finger engaging member 278 extends out from the bottom of the second finger engaging member toward the first finger engaging member 276. The bottom side of the latching member 280 has a generally arcuate shape featuring an upwardly curve so as not to interfere with the movement of ratcheting head 286 of the latching member 284 when engaging or disengaging from ratcheting head 282. The latching member 280 is thicker at its attachment point to the first finger engaging member 276 than at its attachment point to the ratcheting head 282. The latching member 284 is a flexible arm, and the ratcheting head 286 is attached to the free end of the flexible arm latching member 284. The flexible arm latching member 284 allows for the free travel of the ratcheting head 286, with respect to the second finger engaging member 278.

The ratcheting teeth of the ratcheting head 282 of latching member 280 and the ratcheting teeth of the ratcheting head 286 are adapted to join and lock together when engaged by squeezing the finger engaging members 276, 278 together. The teeth are able to disengage when pulled apart by flexing the first and second elongated members 272, 274 when an opposing force is applied to the finger engaging members 276, 278 by pushing with the thumb and pulling with the fingers of the operating hand thereby separating the parallel engaged teeth.

It can be appreciated that the ambidextrous locking clamp system 270 can be used with either the left or right hand with identical methods of separating and disengaging the teeth of ratcheting heads 282, 286.

Figure 26:
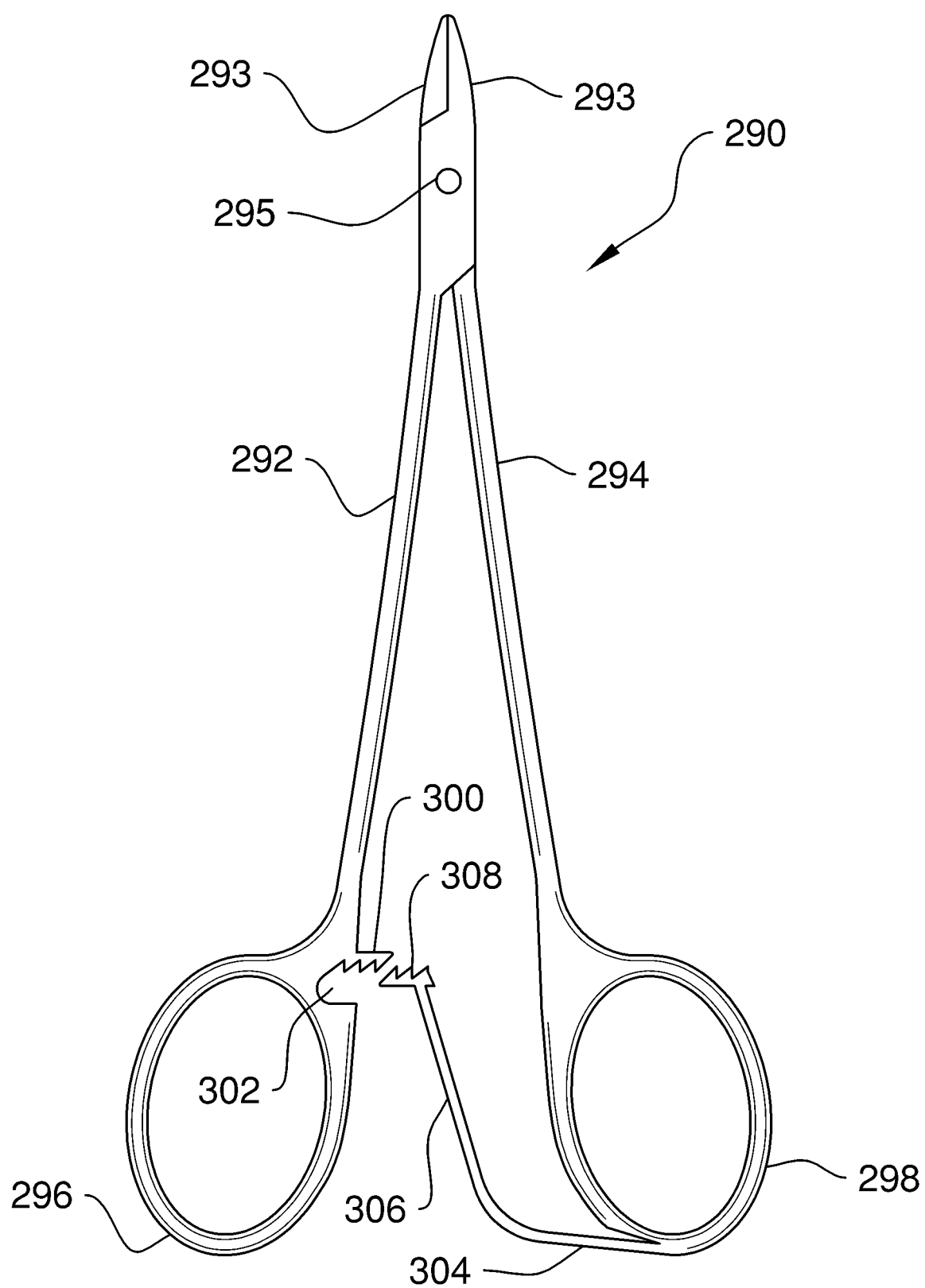
FIG. 26 is a front plane view of a tenth alternate embodiment of the present technology.

Referring now to FIG. 26, a tenth alternate embodiment of the ambidextrous locking clamp system of the present technology is shown and generally designated by the reference numeral 290. More particularly, the ambidextrous locking clamp system 290 has a first elongated member 292 and a second elongated member 294 each having a working head 293, wherein the working heads can be, but not limited to, a gripping jaw or a cutting edge. The second elongated member 294 is connected to the first elongate member 292 via a hinge 295. The first and second elongated members 292, 294 each have a corresponding finger engaging member 296, 298 located opposite of their respective working heads 293. The first finger engaging member 296 has a latching member 300 extending out therefrom, and a notch 302 adjacent the latching member 300. The latching member 300 features ratcheting teeth thereon. The second finger engaging member 298 has a latching member 304 extending out therefrom, an arm 306, and a ratcheting head 308. The ratcheting head 308 features ratcheting teeth thereon adapted to engage with the ratcheting teeth of the latching member 300 when the first and second finger engaging members 296, 298 are squeezed together.

Figure 27:
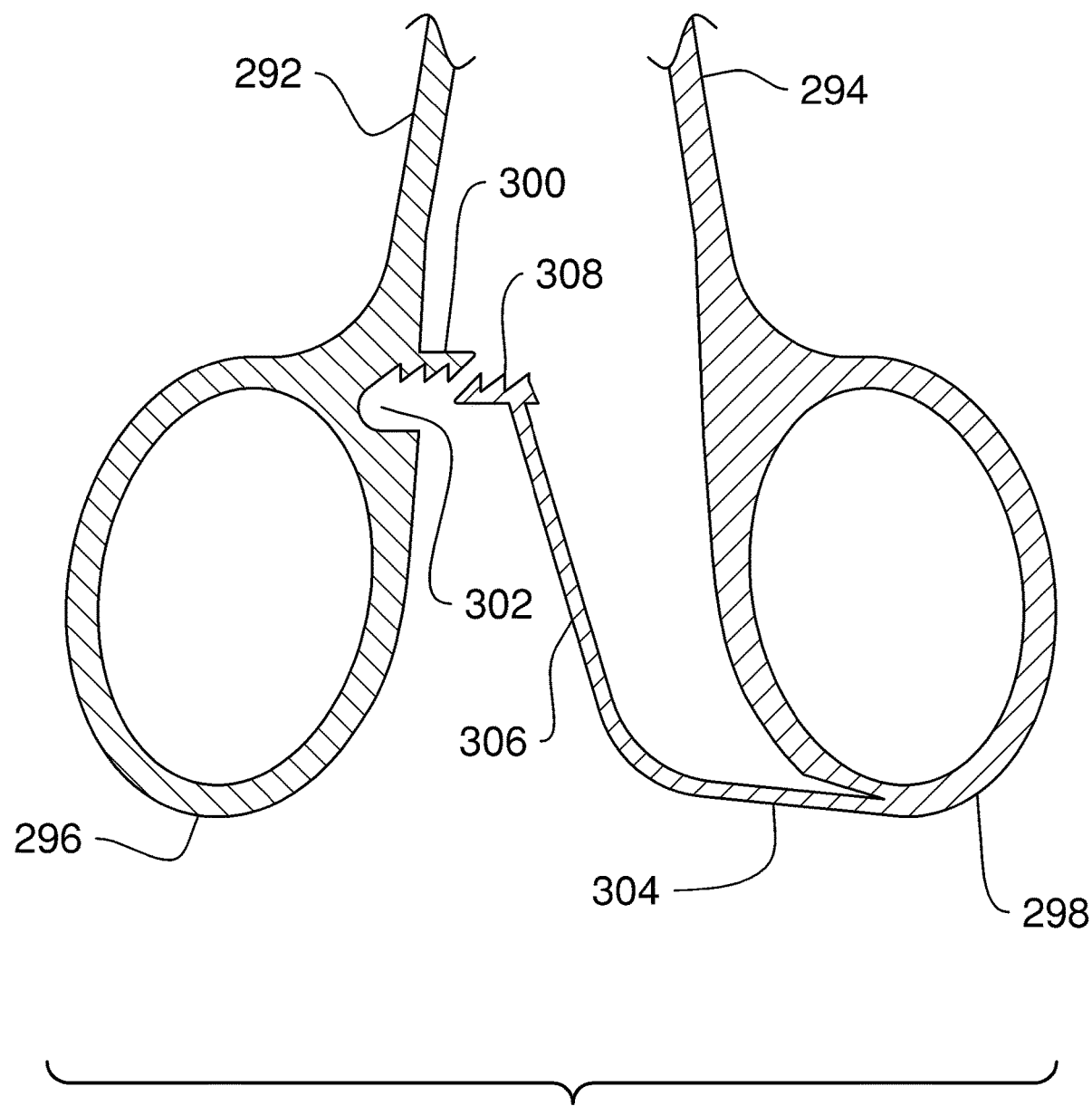
FIG. 27 is an enlarged cross-sectional view of the embodiment in FIG. 26.

As illustrated in FIG. 27, the latching member 300 of the first finger engaging member 296 extends out from the first finger engaging member toward the second finger engaging member 298. The notch 302 can have any geometric shape, but preferably a U-shape with the latching member 300 being positioned directly above or below and adjacent to the U-shaped notch. The notch 302 is located so as to be aligned with the ratcheting head 308 of the latching member 304. The notch 302 is configured to receive the ratcheting head 308 of the latching member 304, and to allow the ratcheting head 308 to engage and disengage from latching member 300. The latching member 304 of the second finger engaging member 298 extends out from the bottom of the second finger engaging member toward the first finger engaging member 296. The arm 306 is attached to the free end of the latching member 304 with an arcuate connection, and the ratcheting head 308 is attached to the free end of the arm 306. The latching member 304 and the arm 306 are flexible allowing for the free travel of the ratcheting head 308, with respect to the second finger engaging member 298. The latching member 304 extends outwardly and upwardly from the interior of the second finger engaging member 298, while the arm 306 extends outwardly and upwardly from the free end of the latching member 306.

The ratcheting teeth of the latching member 300 and the ratcheting teeth of the ratcheting head 308 are adapted to join and lock together when engaged by squeezing the finger engaging members 296, 298 together. The teeth are able to disengage when pulled apart by flexing the first and second elongated members 292, 294 when an opposing force is applied to the finger engaging members 296, 298 by pushing with the thumb and pulling with the fingers of the operating hand thereby separating the parallel engaged teeth.

It can be appreciated that the ambidextrous locking clamp system 290 can be used with either the left or right hand with identical methods of separating and disengaging the teeth of the first latching member 300 and the ratcheting head 308.

The latching members 80, 90, 130, 140, 160, 170, 190, 194, 210, 214, 230, 236, 260, 264, 280, 284, 300, 304 can have indicators thereon and can be adapted to be universally used in many orientations.

Figure 28:
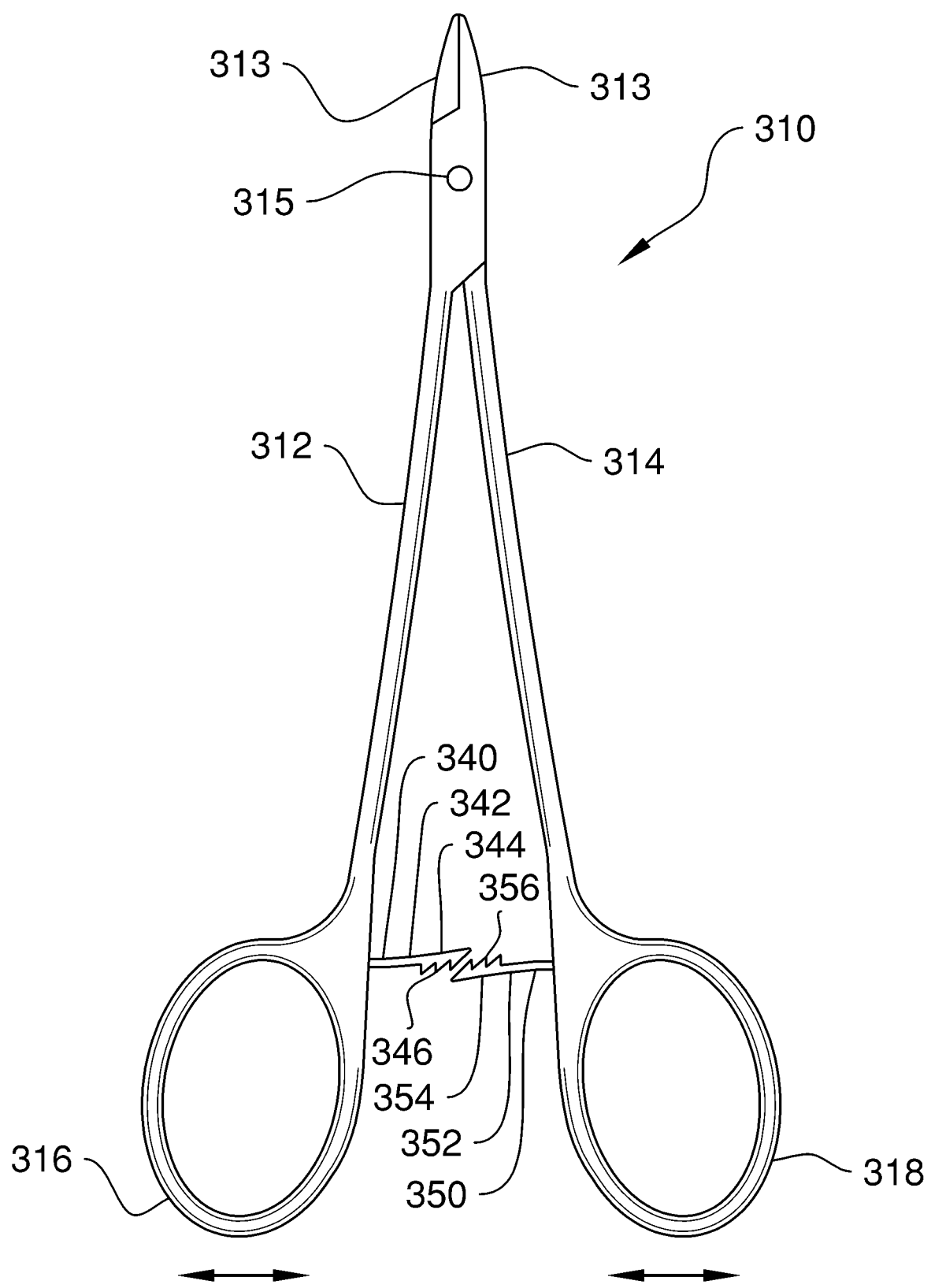
FIG. 28 is a front plane view of the ambidextrous locking clamp system constructed in accordance with the principles of the present technology.

In FIG. 28, a new and improved ambidextrous locking clamp system 310 of the present technology for allowing the use of a hand operated device by a right or left handed user is illustrated and will be described. More particularly, the ambidextrous locking clamp system 310 has a first elongated member 312 and a second elongated member 314 each having a working head 313, wherein the working heads can be, but not limited to, a gripping jaw or a cutting edge. The second elongated member 314 is connected to the first elongated member 312 via a hinge 315. The first elongated member 312 has a first finger engaging member 316 located opposite the working head 313 with the hinge 315 located between the working head 313 and the first finger engaging member 316, and a first latching member 340 extending away from the first elongate member 312 or the first finger engaging member 316. The second elongated member 314 has a second finger engaging member 318 located opposite the working head 313 with the hinge 315 located between the working head 313 and the second finger engaging member 318, and a second latching member 350 extending away from the second elongate member 314 or the second finger engaging member 318. The first and second latching members 340, 350 are oriented toward each other so as to releasably engage with each other. The first and second elongated members 312, 314 can be made from any suitable material having reflex memory.

Figure 29:
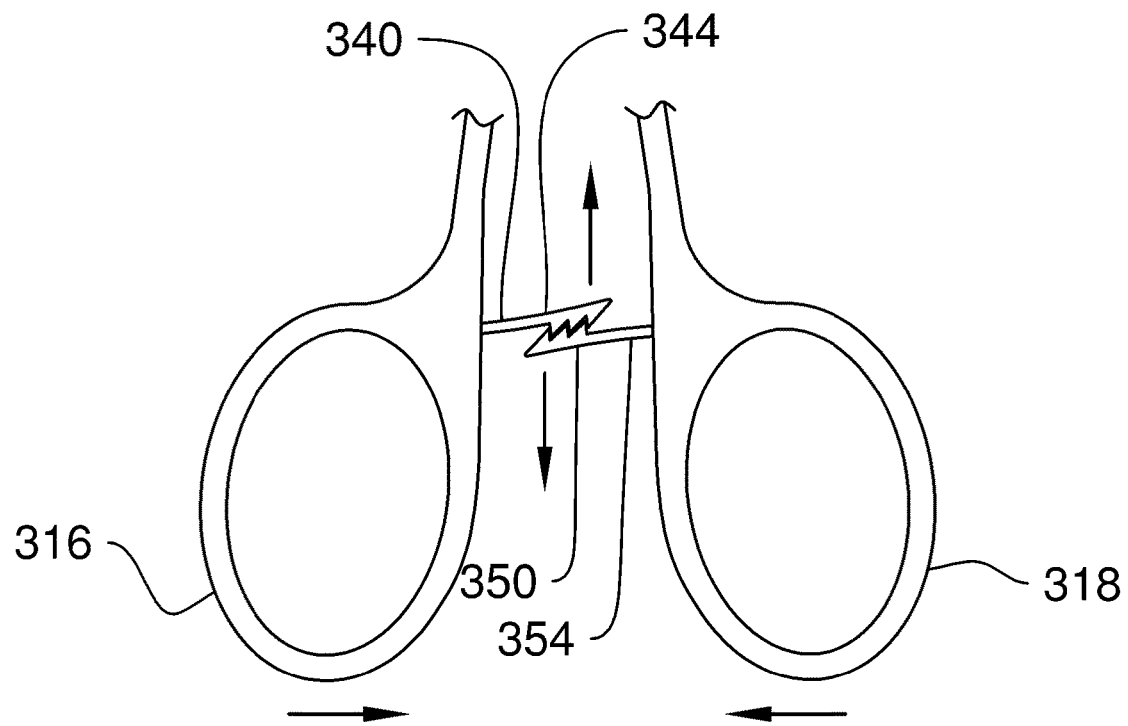
FIG. 29 is an enlarged front plane view of the ratcheting teeth in an engaging configuration of the present technology.

The first and second latching members 340, 350 each have a flexible arm 342, 352, a ratcheting head 344, 354 located at a free end of the flexible arm 342, 352 respectively. The first ratcheting head 344 has a plurality of ratcheting teeth 346 oriented toward or away from the working head 313. The second ratcheting head 354 has a plurality of ratcheting teeth 356 oriented in a direction opposite the first ratcheting head 344 to join and lock together when engaged by squeezing the finger engaging members 316, 318 together, as best illustrated in FIG. 29.

It can be appreciated that to operate the working heads 313 a right or left handed user would insert a thumb in either the first or second finger engaging member 316, 318, and at least one finger in the free finger engaging member opposite the one receiving the thumb. The user would then provide an engaging motion until the ratcheting teeth 346, 356 overlap one another in succession until desire tension or working head force is achieved. The engaging motion is produced by moving the finger engaging members 316, 318 of the first and second members 312, 314 toward each other so as to flex the flexible arms 342, 352 away from each other, thereby interlocking the ratcheting teeth 346, 356 together and locking the ambidextrous locking clamp system 310.

Figure 30:
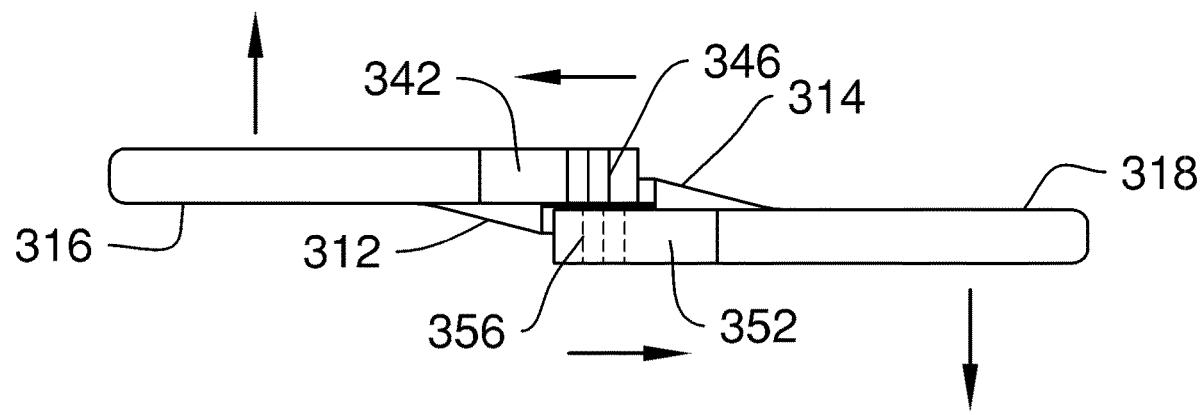
FIG. 30 is an enlarged bottom elevational view of the ratcheting teeth in a disengaging configuration of the present technology.

As best illustrated in FIG. 30, to disengage the ratcheting teeth 346, 356 and release tension or working head force, the user would produce a disengaging motion that is perpendicular to the engaging motion until the ratcheting teeth are slidably disengaged from each other. The disengaging motion is produced by flexing the first and second elongated members 312, 314 in opposite directions by applying an opposing force to the first and second finger engaging members 316, 318 by pushing with the thumb of the operating hand of the user on one of the finger engaging members and pulling with the inserted finger on the other finger engaging member thereby slidably separating the ratcheting teeth. The first and second finger engaging members 316, 318 can then be pulled apart to unlock the ambidextrous locking clamp system 310 or re-engage the ratcheting teeth in a different position to change the tension.

Figure 31:
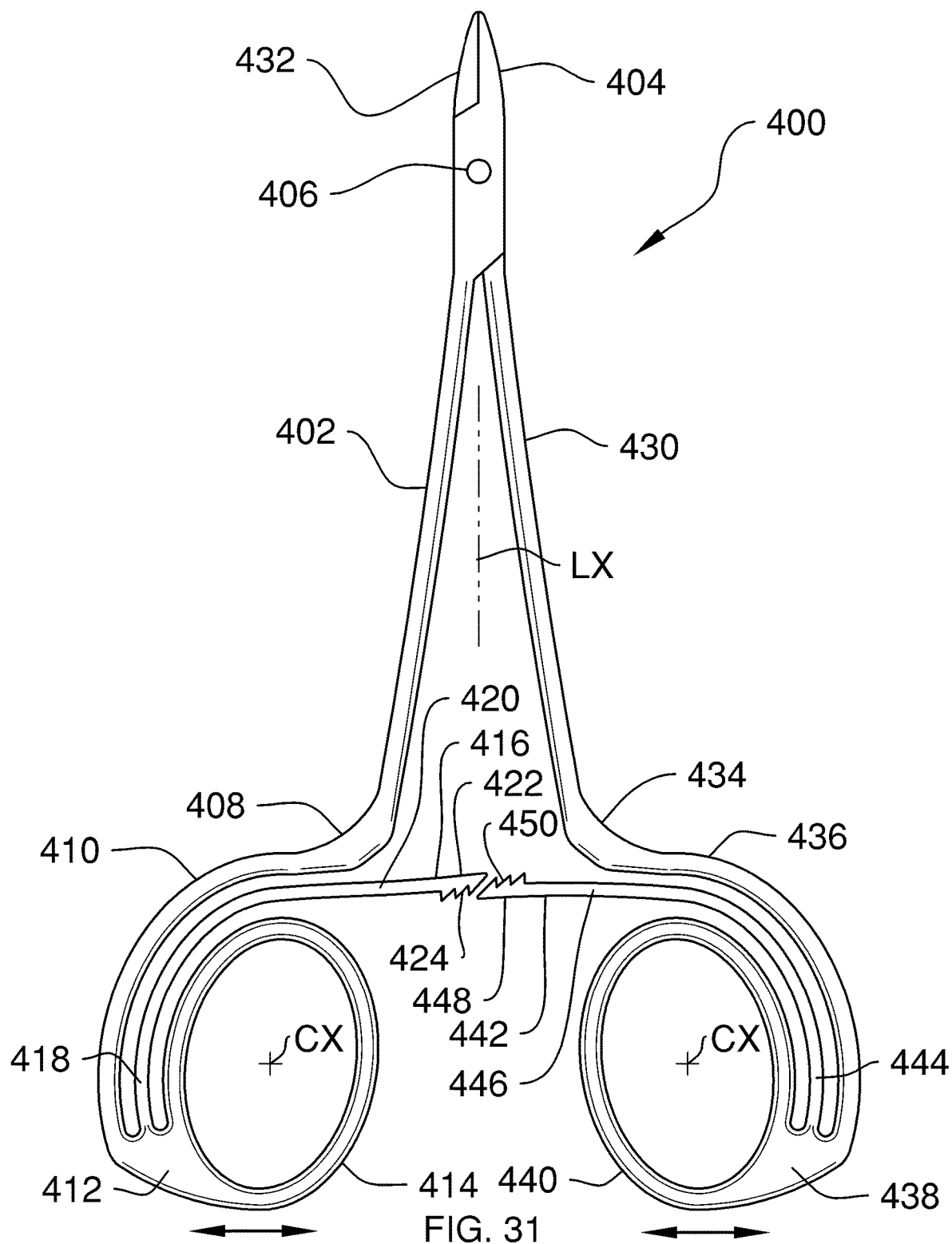
FIG. 31 is a front plane view of an eleventh alternate embodiment of the present technology.

In FIG. 31, a new and improved ambidextrous locking clamp system 400 of the present technology for allowing the use of a hand operated device by a right or left handed user is illustrated and will be described. More particularly, the ambidextrous locking clamp system 400 has a first elongated member 402 and a second elongated member 430 each having a working head 404, 432, respectively, wherein the working heads can be, but not limited to, a gripping jaw or a cutting edge. The second elongated member 430 is connected to the first elongated member 402 via a hinge 406. The first and second elongated members 402, 430 each have a corresponding finger engaging member 414, 440 located opposite of their respective working heads 404, 432. When assembled, the ambidextrous locking clamp system 400 defines a longitudinal axis LX that passes through the hinge 406.

The first elongated member 402 includes a first finger engaging member arm 410, a first finger engaging member 414, and a first latching member 416. The first finger engaging member arm 410 transitions from an end of the first elongated member 402 by way of a first member transitioning section 408. The first member transitioning section 408 is thicker than the first elongated member 402 and first finger engaging member arm 410. The first member transitioning section 408 extends away from the longitudinal axis LX to be exterior of the first elongated member 402.

The first finger engaging member arm 410 has an arcuate or curved profile that extends from the first member transitioning section 408 in a direction away from the longitudinal axis LX to be exterior of the first member transitioning section 408 and opposite the working head 404.

The first finger engaging member 414 is located opposite the working head 404 with the hinge 406 located between the working head 404 and the first finger engaging member 414. The first finger engaging member 414 transitions from an end of the first finger engaging member arm 410 by way of a first member finger transitioning section 412. The first member finger transitioning section 412 is thicker than the first finger engaging member arm 410 and the first finger engaging member 414. The first member finger transitioning section 412 extends toward the longitudinal axis LX to be interior of the first finger engaging member arm 410. Consequently, the first finger engaging member 414 is interior of the first finger engaging member arm 410 toward the longitudinal axis LX.

The first finger engaging member 414 defines a substantially circular or oval opening having a central axis CX and a configuration capable of receiving at least one finger or digit of a user. The first finger engaging member 414 has a portion thereof in a spaced or offset relationship from the first finger engaging member arm 410 to define a space therebetween. The portion of the first finger engaging member 414 that is offset from the first finger engaging member arm 410 has an arcuate or curved profile that corresponds with that of the first finger engaging member arm 410.

Figure 32:
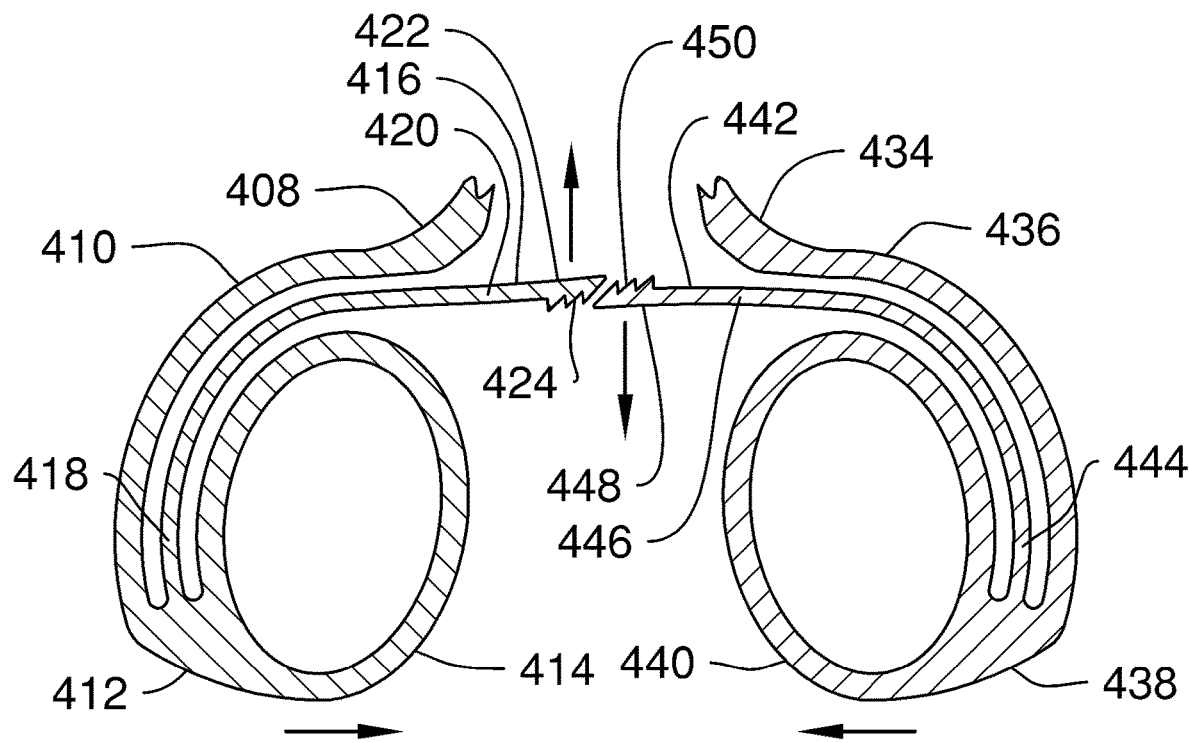
FIG. 32 is an enlarged cross-sectional view of the embodiment in FIG. 31.

As illustrated in FIG. 32, the first latching member 416 has a first arm section 418, a second arm section 420, and a ratcheting head 422. The first arm section 418 extends away from the first member finger transitioning section 412 in the space between the first finger engaging member arm 410 and the first finger engaging member 414. The first arm section 418 has an arcuate or curved profile that corresponds with that of the first finger engaging member arm 410 and the portion of the first finger engaging member 414 that is offset from the first finger engaging member arm 410. Consequently, the first arm section 418 defines a gap between the first finger engaging member arm 410 and the portion of the first finger engaging member 414 that is offset from the first finger engaging member arm 410.

The second arm section 420 extends away from the first arm section 418 toward the longitudinal axis LX. The ratcheting head 422 is located at a free end of the second arm section 420. The ratcheting head 422 features ratcheting teeth 424 extending in a direction aligned with the longitudinal axis LX.

The second elongated member 430 is similar in structure to and a mirror of the first elongated member 402. The second elongated member 430 includes a second finger engaging member arm 436, a second finger engaging member 440, and a second latching member 442. The second finger engaging member arm 436 transitions from an end of the second elongated member 430 by way of a second member transitioning section 434. The second member transitioning section 434 is thicker than the second elongated member 430 and the second finger engaging member arm 436. The second member transitioning section 434 extends away from the longitudinal axis LX to be exterior of the second elongated member 430.

The second finger engaging member arm 436 has an arcuate or curved profile that extends from the second member transitioning section 434 in a direction away from the longitudinal axis LX to be exterior of the second member transitioning section 434 and opposite the working head 432.

The second finger engaging member 440 is located opposite the working head 432 with the hinge 406 located between the working head 432 and the second finger engaging member 440. The second finger engaging member 440 transitions from an end of the second finger engaging member arm 436 by way of a second member finger transitioning section 438. The second member finger transitioning section 438 is thicker than the second finger engaging member arm 436 and the second finger engaging member 440. The second member finger transitioning section 438 extends toward the longitudinal axis LX to be interior of the second finger engaging member arm 436. Consequently, the second finger engaging member 440 is interior of the second finger engaging member arm 436 toward the longitudinal axis LX.

The second finger engaging member 440 defines a substantially circular or oval opening having a central axis CX and a configuration capable of receiving at least one finger or digit of the user. The second finger engaging member 440 has a portion thereof in a spaced or offset relationship from the second finger engaging member arm 436 to define a space therebetween. The portion of the second finger engaging member 440 that is offset from the second finger engaging member arm 436 has an arcuate or curved profile that corresponds with that of the second finger engaging member arm 436.

As illustrated in FIG. 32, the second latching member 442 has a first arm section 444, a second arm section 446, and a ratcheting head 448. The first arm section 444 extends away from the second member finger transitioning section 438 in the space between the second finger engaging member arm 436 and the second finger engaging member 440. The first arm section 444 has an arcuate or curved profile that corresponds with that of the second finger engaging member arm 436 and the portion of the second finger engaging member 440 that is offset from the second finger engaging member arm 436. Consequently, the first arm section 444 defines a gap between the second finger engaging member arm 436 and the portion of the second finger engaging member 440 that is offset from the second finger engaging member arm 436.

The second arm section 446 extends away from the first arm section 444 toward the longitudinal axis LX. The ratcheting head 448 is located at a free end of the second arm section 446. The ratcheting head 448 features ratcheting teeth 450 extending in a direction aligned with the longitudinal axis LX.

The first and second elongated members 402, 430, the first and second finger engaging member arms 410, 436, the first arm sections 418, 444 of the first and second latching members 416, 442 and/or the second arm sections 420, 446 of the first and second latching members 416, 442 can be made from any suitable material having reflex memory.

Figure 33:
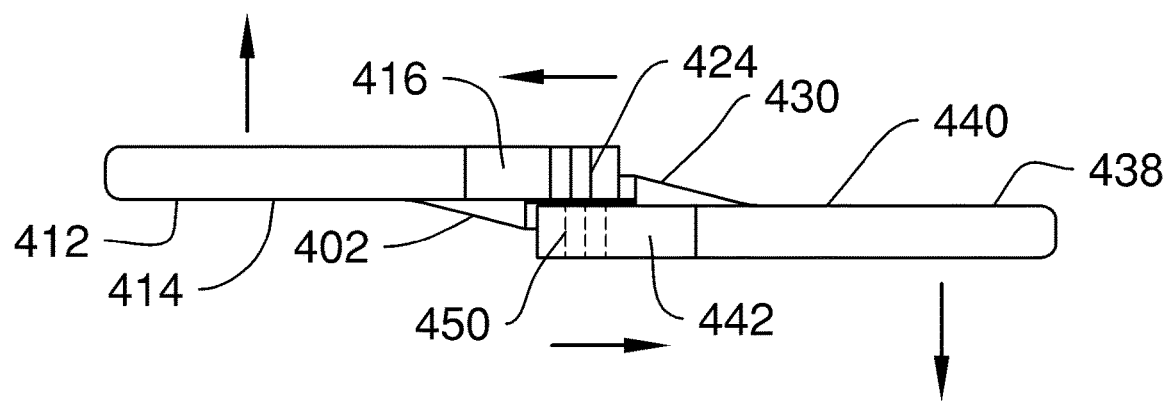
FIG. 33 is an enlarged bottom elevational view of the ratcheting teeth in a disengaging configuration of the embodiment in FIG. 31.

As illustrated in FIG. 33, the ratcheting teeth 424, 450 of the first and second latching members 416, 442 are adapted to join and lock together when engaged by squeezing the first and second finger engaging members 414, 440 together. It can be appreciated that to operate the working heads 404, 432 a right or left handed user would insert a thumb in either the first or second finger engaging member 414, 440, and insert at least one finger in the free finger engaging member opposite the one receiving the thumb. The user would then provide an engaging motion until the ratcheting teeth 424, 450 overlap one another in succession until desire tension or working head force is achieved. The engaging motion is produced by moving the first and second finger engaging members 414, 440 of the first and second elongated members 402, 430 toward each other so that the ratcheting heads 422, 448 move toward each other, thereby interlocking the ratcheting teeth 424, 450 together and locking the ambidextrous locking clamp system 400.

Figure 34:
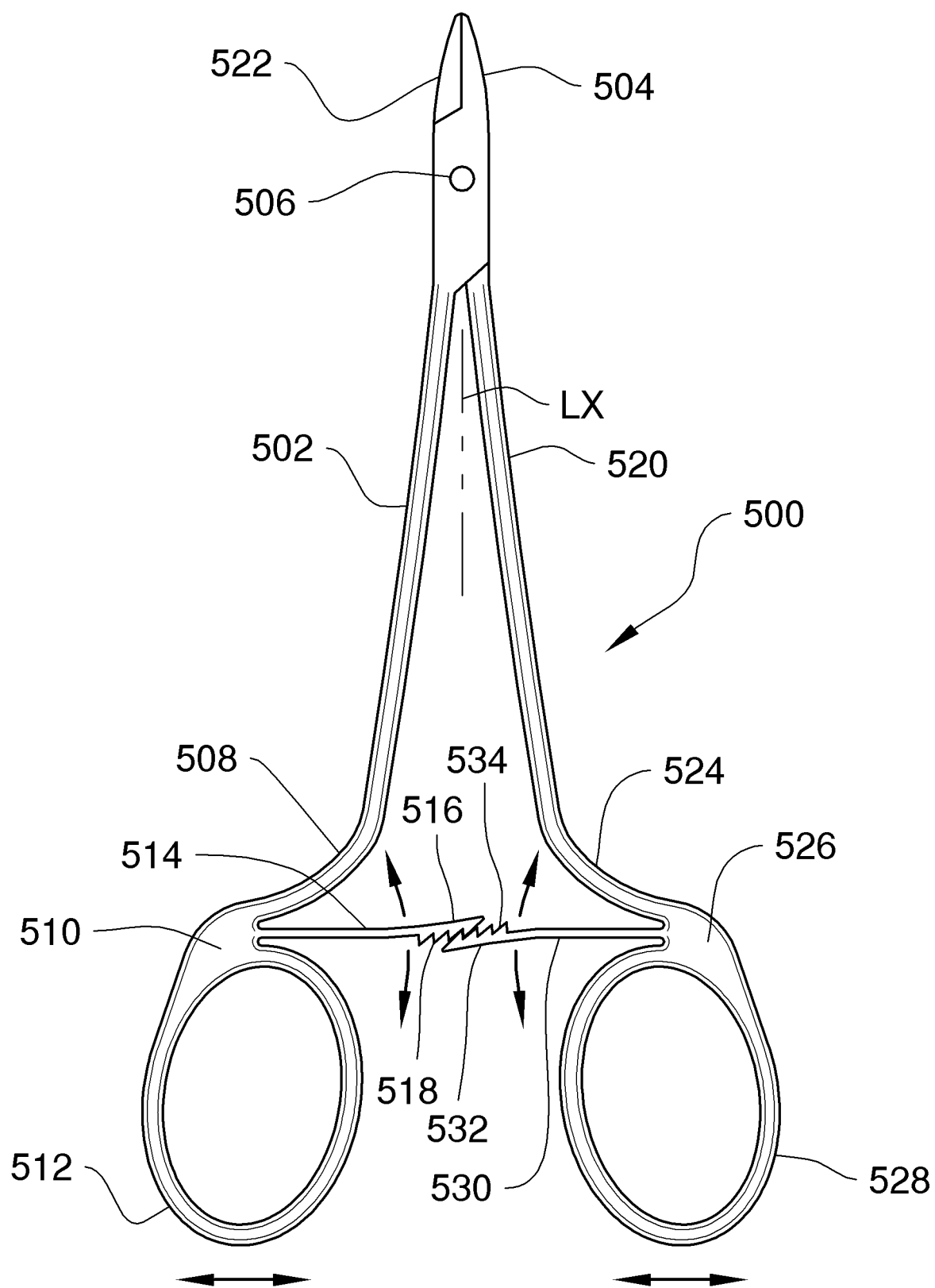
FIG. 34 is a front plane view of an alternate embodiment of the present technology.

Referring to FIG. 34, the present technology can include a new and improved ambidextrous locking clamp system 500 for allowing the use of a hand operated device by a right or left handed user. More particularly, the ambidextrous locking clamp system 500 has a first elongated member 502 and a second elongated member 520 each having a working head 504, 522, respectively, wherein the working heads can be, but not limited to, a gripping jaw or a cutting edge. The first and second elongated members 502, 520 can be rotatably connected to each other via a hinge 506. The first and second elongated members 502, 520 each have a corresponding finger engaging member 512, 528 located opposite of their respective working heads 504, 522. When assembled, the ambidextrous locking clamp system 500 defines a longitudinal axis LX that passes through the hinge 506.

The first elongated member 502 includes a first transitioning section 508, a first shoulder section 510, and a first latching member 514. The first transitioning section 508 can be curve outwardly and away from the first elongated member 502. The first shoulder section 510 transitions from an end of the first transitioning section 508.

The first finger engaging member 512 is located opposite the working head 504 with the hinge 506 located between the working head 504 and the first finger engaging member 512. The first finger engaging member 512 transitions from a side of the first shoulder section 510 opposite the first transitioning section 508. A section of the first finger engaging member 512 adjacent to its connection or transition from the first shoulder section 510 is spaced apart from the first transitioning section 508 to define a space between a convex or outer side of the curved first transitioning section 508 and a convex or outer side of a section of the curved first finger engaging member 512. The first finger engaging member 512 defines a substantially circular or oval opening having a configuration capable of receiving at least one finger or digit of a user.

The first latching member 514 can include a first arm extending away from the first shoulder section 510 in the space between the first transitioning section 508 and the first finger engaging member 512.

The first latching member 514 extends toward the longitudinal axis LX when the locking clamp system 500 is in a closed configuration. A ratcheting head 516 is located at a free end of the first latching member 514. The ratcheting head 516 can feature a tapered or pointed free end, and includes ratcheting teeth 518 extending in a direction aligned with the longitudinal axis LX when the locking clamp system 500 is in the closed configuration. A lateral width or profile of the ratcheting teeth 518 is substantially perpendicular to the longitudinal axis LX when the locking clamp system 500 is in the closed configuration.

The second elongated member 520 is similar in structure to and a mirror of the first elongated member 502, except for an orientation of the ratcheting teeth. The second elongated member 520 includes a second transitioning section 524, a second shoulder section 526, and a second latching member 530. The second transitioning section 524 can be curve outwardly and away from the second elongated member 520. The second shoulder section 526 transitions from an end of the second transitioning section 524.

Figure 35:
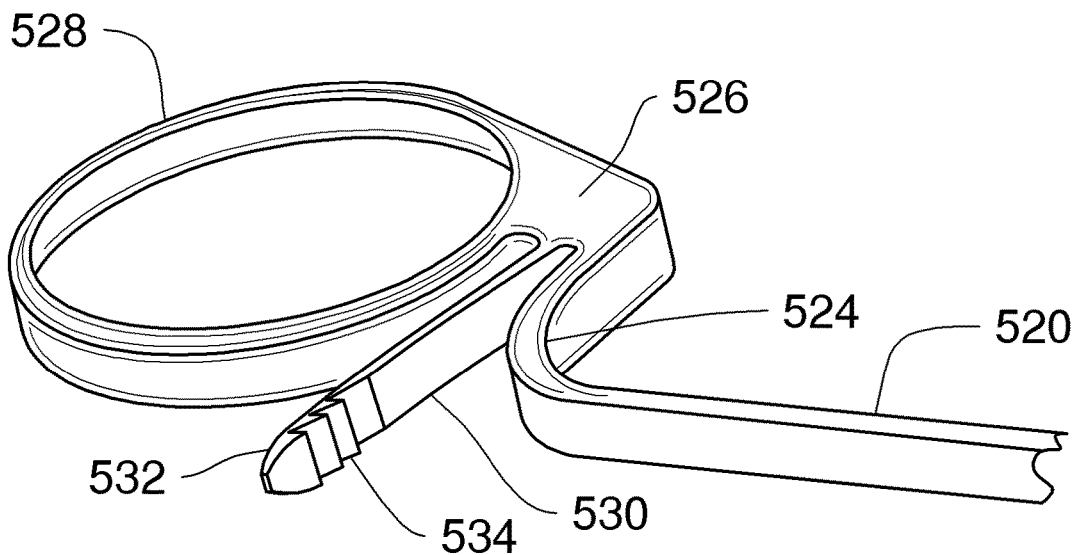
FIG. 35 is a perspective view of the second finger engaging member and latching member of the embodiment in FIG. 34.
Figure 36:
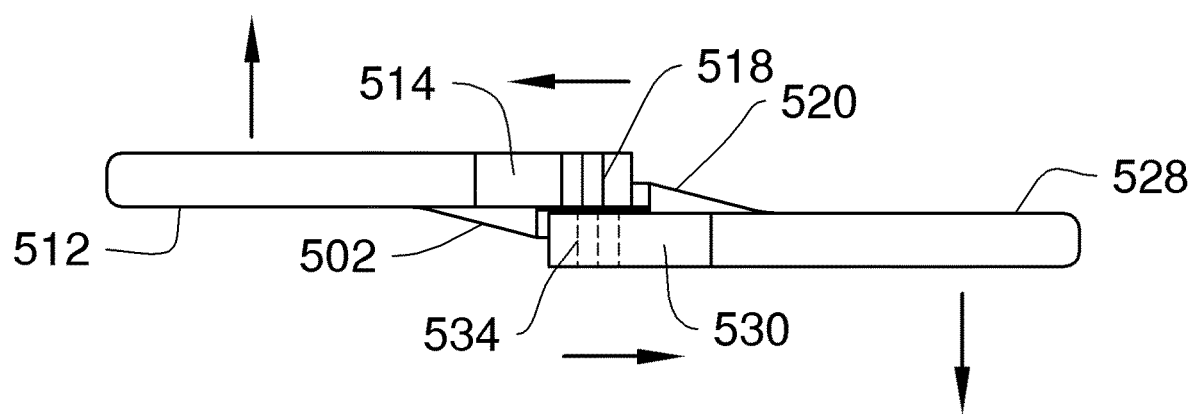
FIG. 36 is an enlarged bottom elevational view of the ratcheting teeth in a disengaging configuration of the embodiment in FIG. 34.

As best illustrated in FIG. 35, the second finger engaging member 528 is located opposite the working head 522 with the hinge 506 located between the working head 522 and the second finger engaging member 528. The second finger engaging member 528 transitions from a side of the second shoulder section 526 opposite the second transitioning section 524. A section of the second finger engaging member 528 adjacent to its connection or transition from the second shoulder section 526 is spaced apart from the second transitioning section 524 to define a space between a convex or outer side of the curved second transitioning section 524 and a convex or outer side of a section of the curved second finger engaging member 528. The second finger engaging member 528 defines a substantially circular or oval opening having a configuration capable of receiving at least one finger or digit of a user.

The second latching member 530 extends toward the longitudinal axis LX when the locking clamp system 500 is in a closed configuration. A ratcheting head 532 is located at a free end of the second latching member 530. The ratcheting head 532 can feature a tapered or pointed free end, and includes ratcheting teeth 534 extending in a direction aligned with the longitudinal axis LX when the locking clamp system 500 is in the closed configuration. A lateral width or profile of the ratcheting teeth 534 is substantially perpendicular to the longitudinal axis LX and facing the ratcheting teeth 548 of the first latching member 514 when the locking clamp system 500 is in the closed configuration.

The first and second transitioning sections 508, 524, and/or the first and second latching members 514, 530 can be made from any suitable material having reflex memory.

As illustrated in FIG. 34, the ratcheting teeth 518, 534 of the first and second latching members 514, 530 are adapted to join and lock together when engaged by squeezing the first and second finger engaging members 512, 528 together. It can be appreciated that to operate the working heads 504, 522 a right or left handed user would insert a thumb in either the first or second finger engaging member 512, 528, and insert at least one finger in the free finger engaging member opposite the one receiving the thumb. The user would then provide an engaging motion until the ratcheting teeth 518, 538 begin to flex apart and overlap one another in succession until desire tension or working head force is achieved. The engaging motion is produced by moving the first and second finger engaging members 512, 528 of the first and second elongated members 502, 520 toward each other so that the ratcheting heads 516, 532 move toward each other, thereby interlocking the ratcheting teeth 518, 534 together and locking the ambidextrous locking clamp system 500.

Referring to FIG. 37, the present technology can include a new and improved ambidextrous locking clamp system 550 for allowing the use of a hand operated device by a right or left handed user. More particularly, the ambidextrous locking clamp system 550 has a first elongated member 552 and a second elongated member 570 each having a working head 554, 572, respectively, wherein the working heads can be, but not limited to, a gripping jaw or a cutting edge. The first and second elongated members 552, 570 can be rotatably connected to each other via a hinge 556. The first and second elongated members 552, 570 each have a corresponding finger engaging member 562, 578 located opposite of their respective working heads 554, 572. When assembled, the ambidextrous locking clamp system 550 defines a longitudinal axis LX that passes through the hinge 556.

The first elongated member 552 includes a first receipt section 558 that defines a first opening or bore 560 therethrough, as best illustrated in FIG. 38. The first receipt section 558 can have a width greater than the first elongated member 552, thereby creating a widened section to accommodate the first bore 560.

The first finger engaging member 562 is located opposite the working head 554 with the hinge 556 located between the working head 554 and the first finger engaging member 562. The first finger engaging member 562 transitions from the first receipt section 558, and continue in a substantially circular or oval path having a configuration capable of receiving at least one finger or digit of a user.

Figure 39:
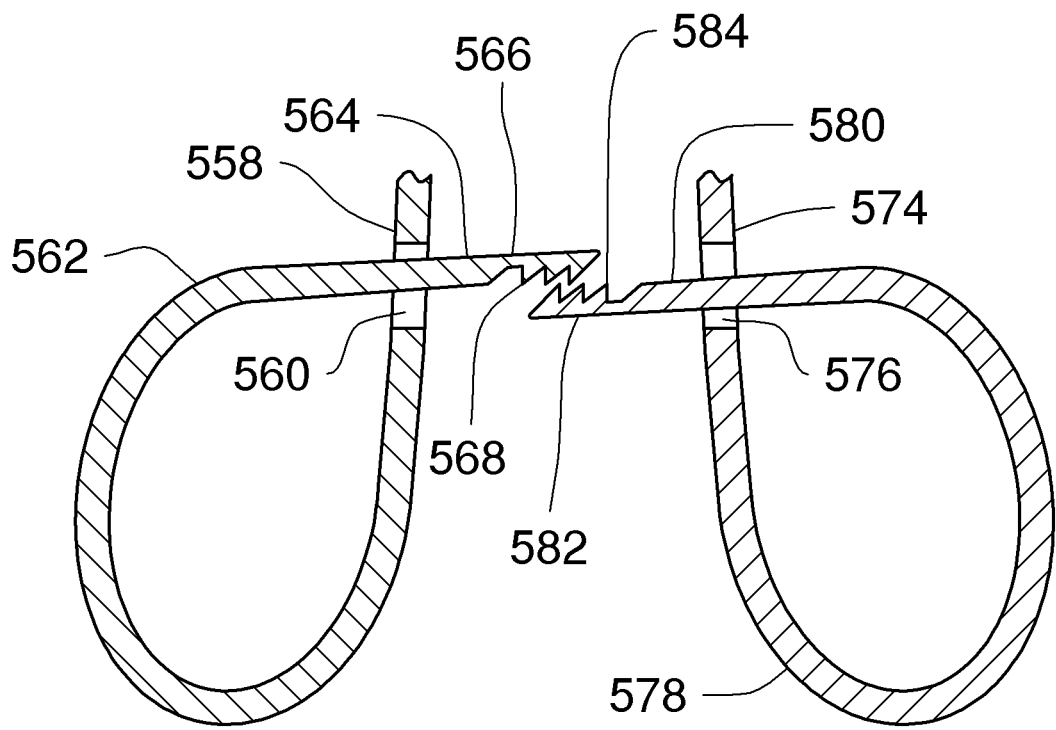
FIG. 39 is an enlarged cross-sectional view of the embodiment in FIG. 39 taken along cross-section line 39-39.

The first finger engaging member 562 includes a first latching member 564 extending or transitioning therefrom, which is received or inserted through the first bore 560, as best illustrated in FIGS. 38 and 39. The first latching member 564 extends toward the longitudinal axis LX when the locking clamp system 550 is in a closed configuration. A ratcheting head 566 is located at a free end of the first latching member 564, which includes ratcheting teeth 568. A lateral width or profile of the ratcheting teeth 568 is substantially perpendicular to the longitudinal axis LX when the locking clamp system 550 is in the closed configuration.

The second elongated member 570 is similar in structure to and a mirror of the first elongated member 552, except for an orientation of the ratcheting teeth. The second elongated member 570 includes a second receipt section 574 that defines a second opening or bore 576 therethrough, as best illustrated in FIG. 38. The second receipt section 574 can have a width greater than the second elongated member 570, thereby creating a widened section to accommodate the second bore 576.

The second finger engaging member 578 is located opposite the working head 572 with the hinge 556 located between the working head 572 and the second finger engaging member 578. The second finger engaging member 578 transitions from the second receipt section 574, and continue in a substantially circular or oval path having a configuration capable of receiving at least one finger or digit of a user.

The second finger engaging member 578 includes a second latching member 580 extending or transitioning therefrom, which is received or inserted through the second bore 576, as best illustrated in FIGS. 38 and 39. The second latching member 580 extends toward the longitudinal axis LX when the locking clamp system 550 is in a closed configuration. A ratcheting head 582 is located at a free end of the second latching member 580, which includes ratcheting teeth 584. A lateral width or profile of the ratcheting teeth 584 is substantially perpendicular to the longitudinal axis LX and facing the ratcheting teeth 568 of the first latching member 564 when the locking clamp system 550 is in the closed configuration.

The first and second finger engaging members 562, 578, and/or the first and second latching members 564, 580 can be made from any suitable material having reflex memory. It can be appreciated that the first and second finger elongated members 552, 570, the first and second finger engaging members 562, 578, and the first and second latching members 564, 580 can each be a single integral member that is bent to form the first and second finger engaging members 562, 578, and with their corresponding latching member inserted through their corresponding bore 560, 576, respectively.

Figure 40:
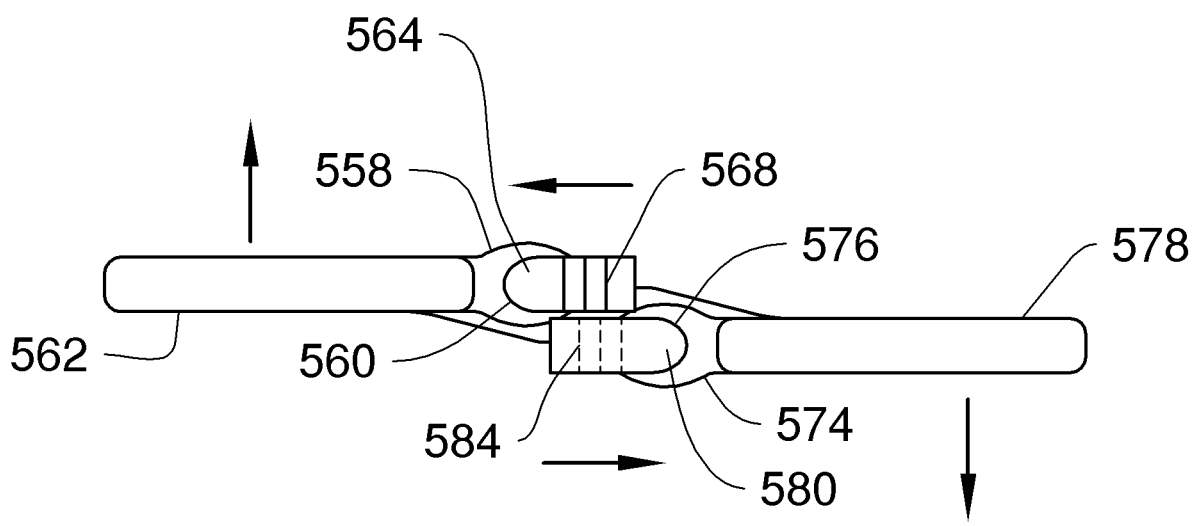
FIG. 40 is an enlarged bottom elevational view of the ratcheting teeth in a disengaging configuration of the embodiment in FIG. 37.

As illustrated in FIG. 40, the ratcheting teeth 568, 584 of the first and second latching members 564, 580 are adapted to join and lock together when engaged by squeezing the first and second finger engaging members 562, 578 together. It can be appreciated that to operate the working heads 554, 572 a right or left handed user would insert a thumb in either the first or second finger engaging member 562, 578, and insert at least one finger in the free finger engaging member opposite the one receiving the thumb. The user would then provide an engaging motion until the ratcheting teeth 568, 584 begin to flex apart and overlap one another in succession until desire tension or working head force is achieved. The engaging motion is produced by moving the first and second finger engaging members 562, 578 of the first and second elongated members 552, 570 toward each other so that the ratcheting heads 566, 582 move toward each other, thereby interlocking the ratcheting teeth 568, 584 together and locking the ambidextrous locking clamp system 550.

Figures 41, 42:
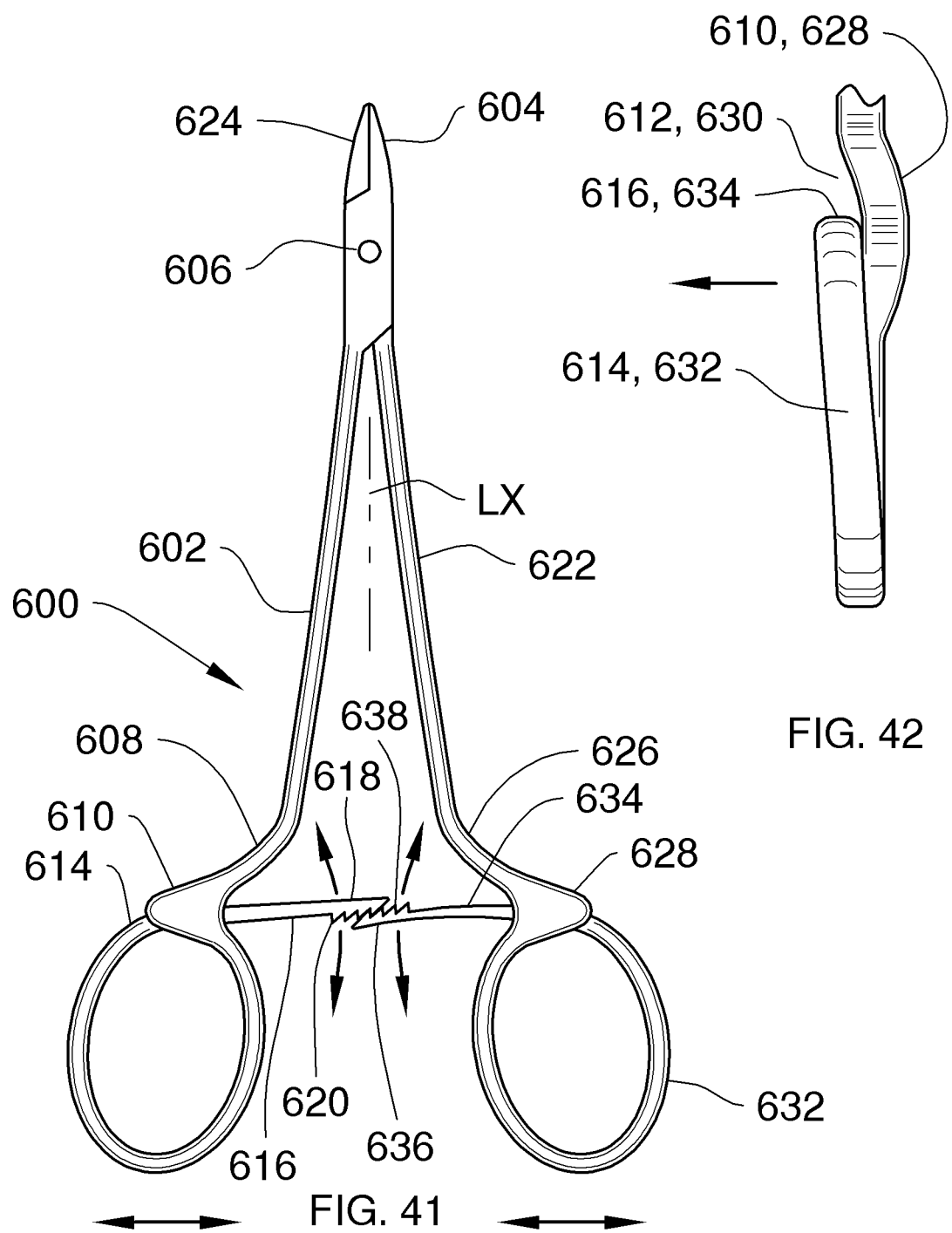
FIG. 41 is a front plane view of an alternate embodiment of the present technology.
FIG. 42 is a side plane view of the alternate embodiment in FIG. 41.

Referring to FIG. 41, the present technology can include a new and improved ambidextrous locking clamp system 600 for allowing the use of a hand operated device by a right or left handed user. More particularly, the ambidextrous locking clamp system 600 has a first elongated member 602 and a second elongated member 622 each having a working head 604, 624, respectively, wherein the working heads can be, but not limited to, a gripping jaw or a cutting edge. The first and second elongated members 602, 622 can be rotatably connected to each other via a hinge 606. The first and second elongated members 602, 622 each have a corresponding finger engaging member 614, 632 located opposite of their respective working heads 604, 624. When assembled, the ambidextrous locking clamp system 600 defines a longitudinal axis LX that passes through the hinge 606.

The first elongated member 602 includes a first transitioning section 608, a first shoulder section 610, and a first latching member 616. The first transitioning section 608 can be curve outwardly and away from the first elongated member 602. The first shoulder section 610 transitions from an end of the first transitioning section 608, and can be bent or configured to define a first open space, notch or recess 612, as best illustrated in FIG. 42. The first shoulder section 610 can have a width greater than that of the first elongated member 602 and/or the first transitioning section 608, thereby creating a widened section.

The first finger engaging member 614 is located opposite the working head 604 with the hinge 606 located between the working head 604 and the first finger engaging member 614. The first finger engaging member 614 transitions from a side of the first shoulder section 610 opposite the first transitioning section 608. The first finger engaging member 614 defines a substantially circular or oval opening having a configuration capable of receiving at least one finger or digit of a user.

The first finger engaging member 614 includes a first latching member 616 extending or transitioning therefrom, which is received in the first recess 612, as best illustrated in FIG. 42. The first latching member 616 extends toward the longitudinal axis LX when the locking clamp system 600 is in a closed configuration. A ratcheting head 618 is located at a free end of the first latching member 616, which includes ratcheting teeth 620. A lateral width or profile of the ratcheting teeth 620 is substantially perpendicular to the longitudinal axis LX when the locking clamp system 600 is in the closed configuration.

The second elongated member 622 is similar in structure to and a mirror of the first elongated member 602, except for an orientation of the ratcheting teeth. The second elongated member 622 includes a second transitioning section 626, a second shoulder section 628, and a second latching member 634. The second transitioning section 626 can be curve outwardly and away from the second elongated member 622. The second shoulder section 628 transitions from an end of the second transitioning section 626, and can be bent or configured to define a second open space, notch or recess 630, as best illustrated in FIG. 42. The second shoulder section 628 can have a width greater than that of the second elongated member 622 and/or the second transitioning section 626, thereby creating a widened section.

The second finger engaging member 632 is located opposite the working head 624 with the hinge 606 located between the working head 624 and the second finger engaging member 632. The second finger engaging member 632 transitions from a side of the second shoulder section 628 opposite the second transitioning section 626. The second finger engaging member 632 defines a substantially circular or oval opening having a configuration capable of receiving at least one finger or digit of a user.

The second finger engaging member 632 includes a second latching member 634 extending or transitioning therefrom, which is received in the second recess 630, as best illustrated in FIG. 42. The second latching member 634 extends toward the longitudinal axis LX when the locking clamp system 600 is in a closed configuration. A ratcheting head 636 is located at a free end of the second latching member 634, which includes ratcheting teeth 638. A lateral width or profile of the ratcheting teeth 638 is substantially perpendicular to the longitudinal axis LX when the locking clamp system 600 is in the closed configuration.

The first and second transitioning sections 608, 626, the first and second finger engaging members 614, 632 and/or the first and second latching members 616, 634 can be made from any suitable material having reflex memory.

The ratcheting teeth 620, 638 of the first and second latching members 616, 634 are adapted to join and lock together when engaged by squeezing the first and second finger engaging members 614, 632 together. It can be appreciated that to operate the working heads 604, 624 a right or left handed user would insert a thumb in either the first or second finger engaging member 614, 632, and insert at least one finger in the free finger engaging member opposite the one receiving the thumb. The user would then provide an engaging motion until the ratcheting teeth 620, 638 begin to flex apart and overlap one another in succession until desire tension or working head force is achieved. The engaging motion is produced by moving the first and second finger engaging members 614, 632 of the first and second elongated members 602, 622 toward each other so that the ratcheting heads 618, 636 move toward each other, thereby interlocking the ratcheting teeth 620, 638 together and locking the ambidextrous locking clamp system 600.

Referring to FIGS. 43-48, any embodiment of the present technology can include a new and improved working head and/or pivoting portion 650 for reducing or eliminating any lateral lag association with the pivoting portion including a hinge 680. One disadvantage of known types of hand operated locking devices is that the tolerance in the pivoting portion of the working head creates a lateral lag where a male portion goes through a female portion at the pivot point. This lateral lag creates unwanted wiggle or uncontrolled operation. Lateral stiffness at this pivot portion is beneficial to keep the locking fingers or latching members to stay engaged. However, it is not desirable to tighten the tolerance in the pivot portion to remove this lateral lag to the point where it does not function properly to overcome this disadvantage. In the locked position as designed, there is too much space at the pivot point with traditional manufacturing process.

The embodiments of the present technology can utilize a pivot portion 650 associated with a first elongated member 652 and a second elongated member 670 each having a working head 660, 676, respectively, wherein the working heads can be, but not limited to, a gripping jaw or a cutting edge. The first and second elongated members 652, 670 can be rotatably connected to each other via a hinge 680. The first and second elongated members 652, 670 each have a corresponding finger engaging member (not shown) located opposite of their respective working heads 660, 676.

In the exemplary, the first elongated member 652 can include a planar male portion 654 transitioning therefrom, and the working head 660 transitions from the male portion 654 from a side opposite the first elongated member 652. The hinge 680 passes through or is pivotably associated with generally central location of the male portion 654. The male portion 654 can be configured so that the first elongated member 652 and the working head 660 are offset from each other orientated on either side of the hinge 680. The male portion 654 has a thickness less than the first elongated member 652 and the working head 660. It can be appreciated that the planar male portion can be associated with the second elongated member and the female portion with the first elongated member.

A primary wedge 656 extends from the male portion 654 at a location adjacent to a juncture or transitioning portion of the first elongated member 652 and the male portion 654. The primary wedge 656 can be two wedges extending out from opposite sides of the male portion 654. Each primary wedge 656 can taper from an exterior side of the male portion 654 toward the hinge to create a primary wedge thickness.

Optionally, a second wedge 658 can extend from the male portion 654 at a location adjacent to a juncture or transitioning portion of the working head 676 and the male portion 654. The secondary wedge 658 can be two wedges extending out from opposite sides of the male portion 654. Each secondary wedge 658 can taper from an exterior side of the male portion 654 toward the hinge to create a secondary wedge thickness.

The second elongated member 670 can include a female portion 672 transitioning therefrom, which defines a slot 674. The working head 676 transitions from the female portion 672 from a side opposite the second elongated member 670. The hinge 680 passes through or is pivotably associated with generally central location of the female portion 672. The female portion 672 can be configured so that the second elongated member 670 and the working head 676 are offset from each other orientated on either side of the hinge 680.

The slot 674 of the female portion 672 is configured to receive the male portion 654 of the first elongated member 652, so that male portion 654 is pivotable therein about the hinge 680. A thickness of the male portion 654 is less than a thickness of the slot 674, thereby create a gap between both sides of the male portion 654 and the sides of the female portion 672 that defines the slot 674, as best illustrated in FIG. 45.

Figure 46:
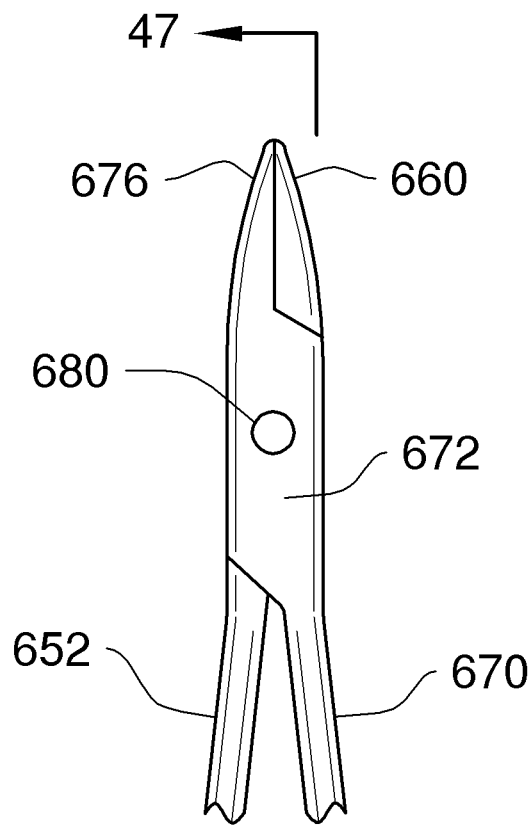
FIG. 46 is a front plane view of the alternate embodiment in FIG. 43 with the working head in a closed configuration.

The gap allows free pivotable motion of the first and second elongated members 652, 670 in relation to the hinge 680, between an open position illustrated in FIG. 44 and a closed position illustrated in FIG. 46. This pivoting movement pivots the working heads 660, 676 together.

The primary and secondary wedges 656, 658 are offset from each other orientated on either side of the hinge 680. This offset orientation allows the primary and secondary wedges 656, 658 to be removed or withdrawn from the slot 674 when the present technology is in an open position, as best illustrated in FIGS. 43 and 44.

Figure 47:
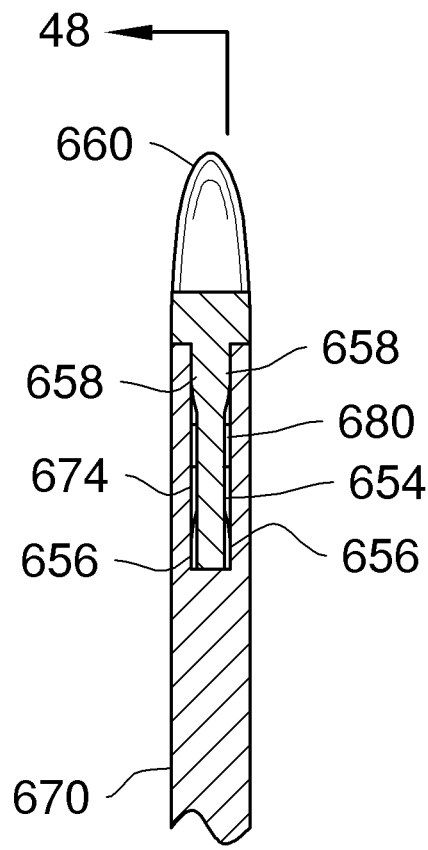
FIG. 47 is a cross-sectional view of the embodiment in FIG. 46 taken along cross-section line 47-47.
Figure 48:
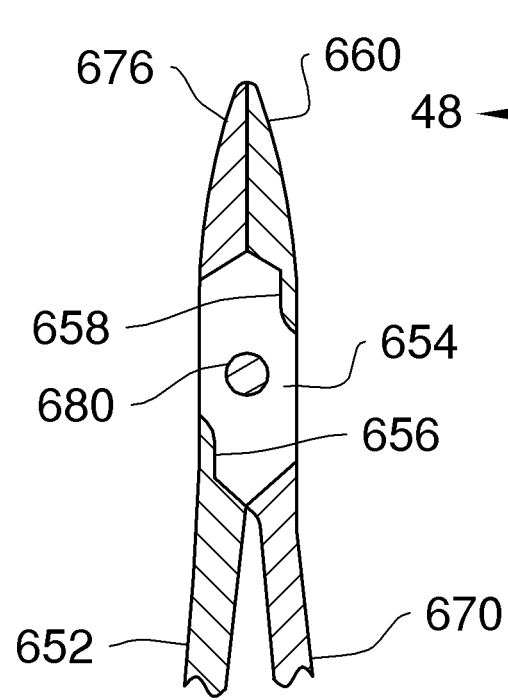
FIG. 48 is a cross-sectional view of the embodiment in FIG. 47 taken along cross-section line 48-48.

During a closing operation associated with interlocking the ratcheting teeth together and locking the ambidextrous locking clamp system, the primary and secondary wedges 656, 658 are pivoted into the slot 674 so that a free edge of each of the wedges contact the side of the female portion 672 that defines the slot 674, respectfully. The wedges 656, 658 fill the gap between the male portion 654 and the side of the female portion 672 that defines the slot 674, thereby eliminating all lateral lag or wiggle associated with operating the present technology tool, as best illustrated in FIG. 47.

It can be appreciated that the ratcheting heads of the embodiments of the present technology can feature a tapered or pointed free end.

The ratcheting heads of the present technology, respectively, can move by:

Pivoting the first and second finger engaging members about the first and second member transitioning sections;

Flexing the first and second finger engaging member arms;

Pivoting the first arm sections about the first and second member finger transitioning sections;

Flexing the first arm sections; and/or Flexing the second arm sections.

To disengage the ratcheting teeth and release tension of working head force, the user would produce a disengaging motion that is perpendicular to the engaging motion until the ratcheting teeth are slidably disengaged from each other. The disengaging motion may be produced by moving the first and second elongated members in opposite directions by applying an opposing force to the first and second finger engaging members by pushing with the thumb of the operating hand of the user on one of the finger engaging members and pulling with the inserted finger on the other finger engaging member thereby slidably separating the ratcheting teeth. The first and second finger engaging members can then be pulled apart to unlock the ambidextrous locking clamp system or re-engage the ratcheting teeth in a different position to change the tension.

It can be appreciated that the engaging and disengaging motions can be initiated by either a left or right handed user in the same manner by simply inserting the thumb of the operating hand in one of the first and second finger engaging members and the at least one finger of the same operating hand in the other finger engaging member.

The latching members can have indicators thereon and can be adapted to be universally used in many orientations.

The above described engaging and disengaging motion can be used for all embodiments of the present technology, and in use, it can now be understood that either a right hand or left hand user can operate the ambidextrous locking clamp system. As described above, the user would apply opposing force to the finger engaging members pushing with the thumb and pulling with the fingers of the operating hand thereby separating the engaged teeth of the first and second latching members.

While a preferred embodiment of the ambidextrous locking clamp system has been described in detail, it should be apparent that modifications and variations thereto are possible, all of which fall within the true spirit and scope of the technology. With respect to the above description then, it is to be realized that the optimum dimensional relationships for the parts of the technology, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present technology. For example, any suitable sturdy material may be used for the manufacture of the ambidextrous locking clamp system, such as but not limited to, steel, aluminum, plastics, and composites. And although manipulating objects with a tool having latching members have been described, it should be appreciated that the ambidextrous locking clamp system herein described is also suitable for all types of hand operated locking tools having a at least two hingedly connected arms.

Therefore, the foregoing is considered as illustrative only of the principles of the technology. Further, since numerous modifications and changes will readily occur to those skilled in the art, it is not desired to limit the technology to the exact construction and operation shown and described, and accordingly, all suitable modifications and equivalents may be resorted to, falling within the scope of the technology.

What is claimed as being new and desired to be protected by Letters Patent of the United States is as follows:

1. An ambidextrous locking clamp system for allowing a right hand or left hand user to operate said clamp, said system comprising:
    at least one first member comprising:
        at least one first elongated body including a planar portion, at least one first working head located at an end of said first elongated body, and a first pair of wedges laterally extending away from each other from opposite sides of said planar portion and perpendicular therewith;
        at least one first finger engaging member; and
        at least one first latching member including first member ratcheting teeth;
    at least one second member comprising:
        at least one second elongated body including a female portion defining a slot, and at least one second working head located at an end of said second elongated body, said slot being configured to receive said planar portion of said first member;
        at least one second finger engaging member; and
        at least one second latching member including second member ratcheting teeth;
    wherein said first and second members being in a pivotable relationship about a pivot point so that said first and second working heads move toward each other when said first and second finger engaging member are moved toward each other; and
    wherein said first and second member ratcheting teeth being orientated to be engageable with each other by an engaging motion when said first and second finger engaging members are moved toward each other;
    wherein each of said wedges being configured to contact an interior side of said female portion that defines said slot, respectively, when said first and second working heads are in a closed position.

2. The system of claim 1, wherein said slot is defined through said female portion between two side members of said female portion of equal length and parallel with a longitudinal axis of said second member.

3. The system of claim 1, wherein an exterior edge of said wedges is flush with an edge of said planar portion.

4. The system of claim 1, wherein said wedges each includes an exterior side and an interior tapered side, said wedges are configured so that said interior tapered side enters said slot prior to said exterior side during the engaging motion.

5. The system of claim 1, wherein said wedges are adjacent said first elongated body, with said pivot point being located between said wedges and said working head of said first member.

6. The system of claim 1, wherein said planar portion includes a second pair of wedges each extending from opposite sides of said planar portion away from each other and perpendicular with said planar portion, and wherein said second pair of wedges are configured to contact the interior side of said female portion that defines said slot when said first and second working heads are in a closed position.

7. The system of claim 6, wherein said second pair of wedges each includes an exterior side and an interior tapered side, said second pair of wedges are configured so that said interior tapered side of said second pair of wedges enters said slot prior to said exterior side of said second pair of wedges during the engaging motion.

8. The system of claim 6, wherein said second pair of wedges are adjacent said working head of said first member, with said pivot point being located between said first pair of wedges and said second pair of wedges.

9. The system of claim 6, wherein said first pair of wedges and said second pair of wedges are located on opposite sides of a longitudinal axis of said first member.

10. The system of claim 1, wherein said first latching member is received through a first member opening defined through said first elongated member, and said second latching member is received through a second member opening defined through said second elongated member.

11. The system of claim 10, wherein said first member opening is a recess defined by a bent portion of said first elongated body, and said second member opening is a recess defined by a bent portion of said second elongated body.

12. The system of claim 10, wherein said first member opening is a bore defined through said first elongated body, and said second member opening is a bore defined through said second elongated body.

13. The system of claim 1, wherein said first and second latching members each include a free end featuring side edges that tapered toward each other.

14. The system of claim 1, wherein said first and second member ratcheting teeth having a configuration for disengaging with each other by sliding said first and second member ratcheting teeth apart by a disengaging motion perpendicular to said engaging motion resulting in moving said first and second latching members away from each other when an opposing force is applied to said first and second finger engaging members in either of two directions that are opposite of each other thereby providing an ambidextrous feature of the ambidextrous locking clamp system.

15. A method of using an ambidextrous locking clamp system, said method comprising the steps of:
  a) operating a first finger engaging member of a first member and a second finger engaging member of a second member by a user to move said first and second finger engaging members toward each other about a pivot point in an engaging motion, said pivot point being configured to pivotably connect said first and second members to each other;
  b) rotating a planar portion of said first member and a female portion of said second member about said pivot point during the engaging motion, said planar portion being receivable in a slot defined in said female portion so that a first pair of wedges laterally extending away from each other from opposite sides of said planar portion and perpendicular therewith contacts an interior side of said female portion that defines said slot, respectively, when said first and second working heads are in a closed position;
  c) engaging ratcheting teeth of first and second members with each other by the engaging motion until said ratcheting teeth of said first and second members overlap one another in succession to a user desired tension when a working head of said first member and said second member are in the closed position; and
  d) disengaging said ratcheting teeth of said first and second members by a disengaging motion perpendicular to said engaging motion until said ratcheting teeth are slidably disengaged, the disengaging motion being produced by moving said first and second members in opposite directions when an opposing force is applied to said first and second finger engaging members by pushing on at least one of said first and second finger engaging members and pulling on the other of said first and second finger engaging members thereby slidably separating said ratcheting teeth of said first and second members out of engagement.

16. The method of claim 15 further comprising a second pair of wedges each extending from opposite sides of said planar portion away from each other and perpendicular with said planar portion, and wherein said first and second pair of wedges are each configured to contact said interior side of said female portion that defines said slot when said first and second working heads are in the closed position.

17. The method of claim 16, wherein said slot is defined through said female portion between two side members of said female portion of equal length and parallel with a longitudinal axis of said second member.

18. The system of claim 2, wherein said pivot point is a hinge passing through the two side members of the female portion and the planar portion.

* * * * *